Figure 2:
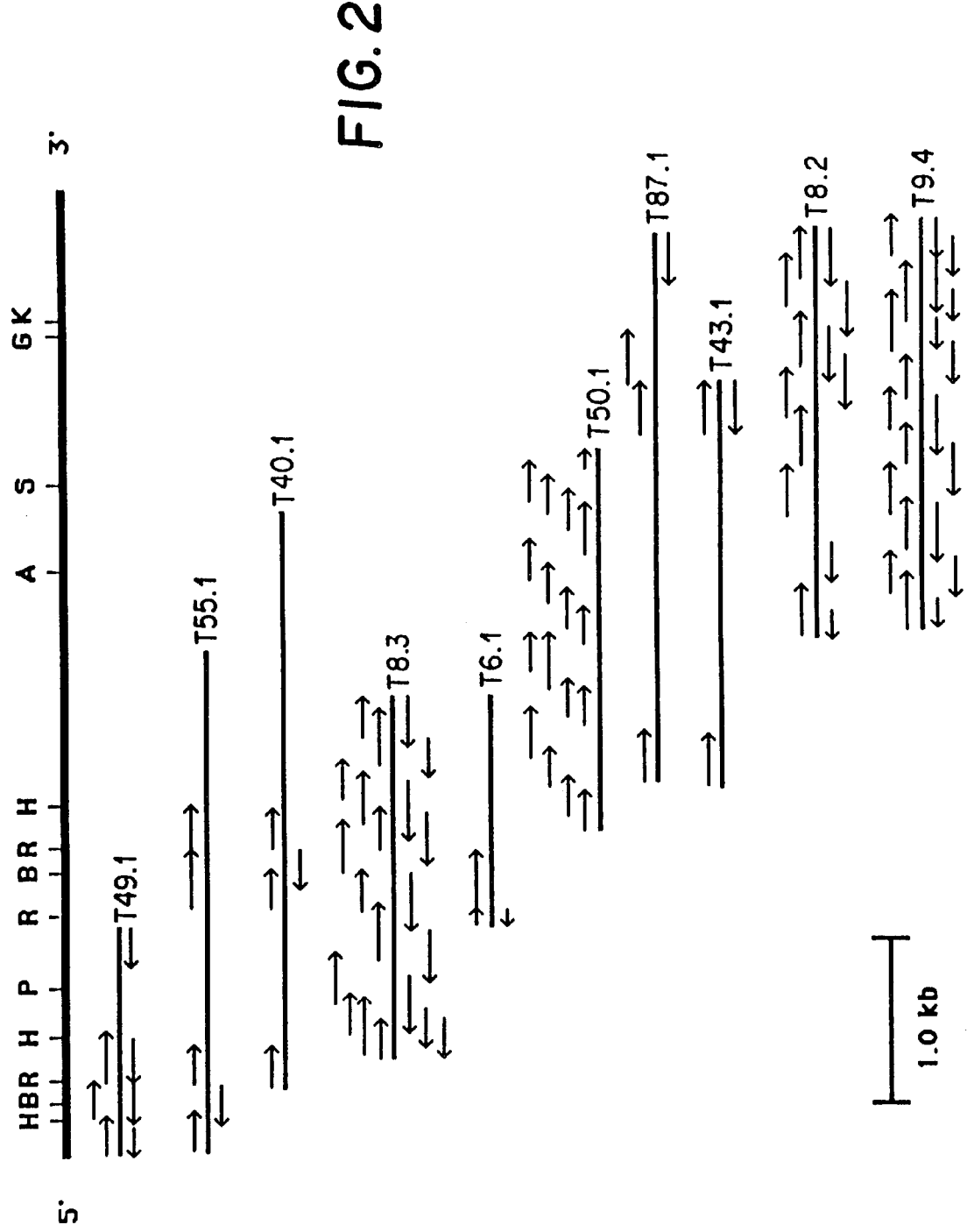

US005981481A

United States Patent [19]
Fearon et al.

[11] Patent Number: 5,981,481
[45] Date of Patent: Nov. 9, 1999

[54] HUMAN C3B/C4B RECEPTOR (CR1)

[75] Inventors: Douglas T. Fearon, Baltimore, Md.;
Lloyd B. Klickstein, Brookline, Mass.;
Winnie W. Wong, Newton, Mass.;
Gerald R. Carson, Wellesley, Mass.;
Michael F. Concino, Newton, Mass.;
Stephen H. Ip, Sudbury, Mass.; Savvas C. Makrides, Bedford, Mass.; Henry C. Marsh, Jr., Reading, Mass.

[73] Assignees: The Johns Hopkins University, Baltimore, Md.; The Brigham & Women's Hospital, Boston; Avant Immunotherapeutics, Inc., Needham, both of Mass.

[21] Appl. No.: 08/470,652

[22] Filed: Jun. 6, 1995

Related U.S. Application Data

[63] Continuation of application No. 08/350,238, Dec. 6, 1974, abandoned, which is a continuation of application No. 08/026,134, Feb. 24, 1993, abandoned, which is a division of application No. 07/332,865, Apr. 3, 1989, Pat. No. 5,212,071, which is a continuation-in-part of application No. 07/176,532, Apr. 1, 1988, abandoned.

[51] Int. Cl.$^6$ .......................... A61K 38/18; C07K 14/46; C12P 21/00
[52] U.S. Cl. .......................... 514/12; 530/350; 435/69.1; 435/172.1; 435/252.3
[58] Field of Search ................. 435/69.1, 172.1, 435/252.3; 530/350; 514/2.12

[56] References Cited

U.S. PATENT DOCUMENTS

| | | | |
|---|---|---|---|
| 4,642,284 | 2/1987 | Cooper et al. | 435/7.94 |
| 4,672,044 | 6/1987 | Schreiber | 436/501 |
| 4,761,371 | 8/1988 | Bell et al. | 435/69.1 |

OTHER PUBLICATIONS

Danielsson et al., Soluble Complement Receptor Type 1 (CD 35) is released from leukocytes by surface cleavage, Eur. J. Immunol. (1994) 24:2725–2731.

Klickstein et al., A Sequence within the COOH–Terminal Region of Human CR1 Determines Expression of a Soluble form of the Receptor. XIVth Int. Complement Workshop Abstracts (1991) pp. 174–175, abstract 135.

Watson et al. "Recombination at the Molecular Level", Chapter 14, In, Molecular Biology of the Gene, Fourth Edition, The Benjamin/Cummings Publishing Company, Inc., Menlo Park, CA. 1988.

Weis et al. 1987, J. Immunol 138:312–315.

Wong et al., 1986, J. Exp. Med. 164:1531–1546.

Sim, 1985, Biochem. J. 232:883–889.

McLean et al., 1987, Nature 330:132–137.

Fearon, 1979, "Regulation of the amplification C3 convertase of human complement by an inhibitory protein isolated from human erythrocyte membrane", Proc. Natl. Acad. Sci 76:5867–5871.

Weis et al., 1986, "Identification of a partial cDNA clone for the C3d/Epstein–Barr virus receptor of human B lymphocytes: Homology with the receptor for fragments C3b and C4b of the third and fourth components of complement", Proc. Natl. Acad. Sci. 83:5639–5642.

Young et al., 1983, "Yeast RNA polymerase II genes: Isolation with antibody probes", Science 222:778–782.

Dykman et al., 1983, "Polymorphism of human erythrocyte C3b/C4b receptor", Proc. Natl. Acad. Sci. 80:1698–1702.

Smith et al., 1987, "Blocking of HIV–1 infectivity by a soluble, secreted form of the CD4 antigen", Science 238:1704–1707.

Lida et al., 1982, "Complement receptor ($CR_1$) deficiency in erythrocytes from patients with systemic lupus erythematosus", J. Exp. Med. 155:1427–1438.

Suggs et al., 1981, "Use of synthetic oligonucleotides as hybridization probes: Isolation of cloned cDNA sequences for human $\beta_2$–microglobulin", Proc. Natl. Acad. Sci. 78:6613–6617.

Hewick et al., 1981, "A gas–liquid solid phase peptide and protein sequenator", The Journal of Biological Chemistry 256:7990–7997.

Nature 330:537–543, Dec. 10, 1987 Leung et al. Growth hormone reeptor and serum binding protein:purification, cloning and expression.

Mol. & Cell. Biol. 10:2973–2982, Jun. 1990, Petch et al., A Trencate, Secreted Form of the Epidermal Growth Factor Receptor is Encoded by an Alternatively . . .

J. of Immunol. 139:855–862, Aug. 1, 1987, Robb et al. Structure–Function Relationships for the IL 2–Receptor System.

Andreatta et al. (Chemical Abstracts vol. 94(21), p. 303, abstract 170110u; 1980, in Enzyme Inhibitors, Proc. Meet., Brodbeck, U.(ed), Verlag Chem., pp. 261–272.

Iida and Nussenzweig (1981, J. Exp. Med. 153:1138–1150).

Medof et al. (1983, Ann. N Y Acad. Sci. 421:299–306).

Atkinson and Jones (1984, J. Clin. Invest. 74:1649–1657).

Yoon and Fearon (1985, J. Immunol. 134:3332–3338).

Seya et al. (1985, J. Immunol. 135:2661–2667).

(List continued on next page.)

Primary Examiner—Elizabeth Kemmerer
Assistant Examiner—David S. Romeo
Attorney, Agent, or Firm—Leon R. Yankwich

[57] ABSTRACT

The present invention relates to the C3b/C4b receptor (CR1) gene and its encoded protein. The invention further provides for the expression of the CR1 protein and fragments thereof. The genes and proteins of the invention have uses in diagnosis and therapy of disorders involving complement activity, and various immune system or inflammatory disorders. In specific embodiments of the present invention detailed in the examples sections infra, the cloning, nucleotide sequence, and deduced amino acid sequence of a full-length CR1 cDNA and fragments thereof are described. The expression of the CR1 protein and fragments thereof is also described. Also described is the expression of a secreted CR1 molecule lacking a transmembrane region. The secreted CR1 molecule is shown to be useful in reducing damage caused by inflammation and in reducing myocardial infarct size and preventing reperfusion injury.

42 Claims, 52 Drawing Sheets

OTHER PUBLICATIONS

Fries et al. (1985, J. Immunol. 135:2673–2679).
Wong et al. (1985, J. Immunol. Meth. 82:303–313).
Holers et al. (1987, Proc. Natl. Acad. Sci. U.S.A. 84:2459–2463).
Klickstein et al. (1987a, J. Exp. Med. 165:1095–1112).
Hourcade et al. (1987a, Abstracts: XIIth Int. Complement Workshop, Arlaud et al. (eds.), pp. 171–172, Abstract 128).
Hourcade et al. (1987b, ibid, p. 172, Abstract 129).
Klickstein et al. (1987b, ibid, p. 180, Abstract 149).
Wilson et al. (Chemical Abstracts vol. 108(1), p. 421, abstract 4304y; 1987, Immunol. Res. 6:192–209).
Frank (1987, New Eng. J. Med. 316:1525–1530).
Hourcade et al. (1988, J. Exp. Med. 168:1255–1270).
Klickstein et al. (1988, J. Exp. Med. 168: 1699–1717).
Kumar et al. (1989, Biochem. 28:4040–4046).
Krych et al. (1989, F.A.S.E.B. J. 3:A368).
Dahlback et al. (1983, Proc. Natl. Acad. Sci. U.S.A. 80:3461–3465).
Chung et al. (1985, Biochem J. 230:133–141).
Chung and Reid (1985, Bioscience Reports 5:855–865).
Wong and Fearon (1985, J. Immunol. 134:4048–4056).
Matzner et al. (Chemical Abstracts vol. 106(1), abstract 3626b, 1986, J. Cell. Physiol. 129:215–220).
Kristensen et al. (1987, Biochem. 26:4668–4674).
Glover et al. (1988, Mol. Immunol. 25: 1261–1267).
Schasteen et al. (1988, Mol. Immunol. 25:1269–1275).
Stenlund et al. (1983, EMBO J. 2:669–673).
McCluskey et al. (1985, Cell 40:247–257).
Hiraki et al. (1986, J. Immunol. 136: 4291–4296).-

FIG. 1A

```
CGT GGT TTG TAG ATG TGC TTG GGG AGA         GGG GCC TCT TCT CCA AGA AGC CCG GAG CCT    60
                                             G   A   S   S   P   R   S   P   E   P

GTC GGG CCG CCG GCG CCC GGT CTC CCC TTC     ATG TGC TGC GGA GGA TCC CTG CTG GCG GTT   120
 V   G   P   P   A   P   G   L   P   F      M   C   C   G   G   S   L   L   A   V

GTG CTG CTT GCG CTG GCC CCG GTG GCC TGG     GGT CAA AAT GCC CCA CCA GAA CTT CCA TTT   180
 V   L   L   A   L   A   P   V   A   W      G   Q   N   A   P   P   E   L   P   F

GCC AGG CCT ACC AAC CTA ACT GAT GAG TTT     GAG TTT CCC ATT ATC ATC TGC CTA CTG TAT   240
 A   R   P   T   N   L   T   D   E   F      E   F   P   I   I   I   C   L   L   Y

GAA TGC CGC CCT GGT TAT TCC GGA AGA CCG     TTT TCT AAA TCA TGT CGT AAT CCT CCA GTC   300
 E   C   R   P   G   Y   S   G   R   P      F   S   K   S   C   R   N   P   P   V

TGG ACT GGT GCT AAG GAC AGG TGC AGA CGT     CCG AGA TGC AGG GAT GAT AAA TAT TCT GTG   360
 W   T   G   A   K   D   R   C   R   R      P   R   C   R   D   D   K   Y   S   V

AAT GGC ATG GTG CAT GTG ATC AAA GGC ATC     CAG TTC GGA TCC CAA ATT AAA CCT GAT CCT TGT   420
 N   G   M   V   H   V   I   K   G   I      Q   F   G   S   Q   I   K   P   D   P   C
```

FIG. 1B

```
ATG AAA GGA CCC CGC CGT GTG AAG TGC CAG GCC CTG AAC AAA TGG GAG CCG GAG CTA CCA
 M   K   G   P   R   R   V   K   C   Q   A   L   N   K   W   E   P   E   L   P   900

AAC AGA AGC TTA TTT TCC TTA AAT GAA GTT GTG GAG TTT GTA TCT TTT GTC
 N   R   S   L   F   S   L   N   E   V   V   E   F   V   S   F   V   870     840

TGC ATT ATA CCT AAC AAA TGC ACG CCT AAT GAA TTT AGG TGT CAG CCT GGC
 C   I   I   P   N   K   C   T   P   N   E   F   R   C   Q   P   G     810   780

TCC ATA TAC CGC ACC TGC AGC AAT GAC GAT CAA GTG GGC ATC TGG AGC GGC CCC GCC CCT
 S   I   Y   R   T   C   S   N   D   D   Q   V   G   I   W   S   G   P   A   P   720

ACC TAC CGC TGC AAT CCT GGA AGC ACC AGA AAG GTG TTT GAG CTT GTG GGT GAG
 T   Y   R   C   N   P   G   S   T   R   K   V   F   E   L   V   G   E     690   660

ATC ACC AAT GGA GAT TTC ATT AGC ACC AGA GAG AAT TTT CAC TAT GGA TCA GTG
 I   T   N   G   D   F   I   S   T   R   E   N   F   H   Y   G   S   V     630   600

GTC ATT TGG GAT AAT GAA ACA CCT ATT GAC AGA ATT CCT TGT GGG CTA CCC CCC ACC
 V   I   W   D   N   E   T   P   I   D   R   I   P   C   G   L   P   P   T   540

ACT AAA GGA TAC CGA CTC ATT GGT TCC TCT GCC ACA TGC ATC ATC TCA GGT GAT ACT
 T   K   G   Y   R   L   I   G   S   S   A   T   C   I   I   S   G   D   T   480
```

```
AGC TGC TCC AGG GTA TGT CAG CCA CCT CCA GAT GTC CTG CAT GCT GAG CGT ACC CAA AGG
 S   C   S   R   V   C   Q   P   P   P   D   V   L   H   A   E   R   T   Q   R
                                930                                         960

GAC AAG GAC AAC TTT TCA CCT GGG CAG GAA GTG TTC TAC AGC TGT GAG CCC GGC TAC GAC
 D   K   D   N   F   S   P   G   Q   E   V   F   Y   S   C   E   P   G   Y   D
                                990                                        1020

CTC AGA GGG GCT GCG TCT ATG CGC TGC ACA CCC CAG GGA GAC TGG AGC CCT GCA GCC CCC
 L   R   G   A   A   S   M   R   C   T   P   Q   G   D   W   S   P   A   A   P
                               1050                                        1080

ACA TGT GAA GTG AAA TCC TGT GAT GAC ATG GGC TTC CAA CTT AAT GGC CGT GTG CTA
 T   C   E   V   K   S   C   D   D   M   G   F   Q   L   N   G   R   V   L
                               1110                                        1140

TTT CCA GTA AAT CTC CAG CTT GGA GCA AAA GTG GAT TTT GTT TGT GAT GAA GGA TTT CAA
 F   P   V   N   L   Q   L   G   A   K   V   D   F   V   C   D   E   G   F   Q
                               1170                                        1200

TTA AAA GGC AGC TCT GCT AGT TAC TGT GTC TTG GCT GGA ATG GAA AGC CTT TGG AAT AGC
 L   K   G   S   S   A   S   Y   C   V   L   A   G   M   E   S   L   W   N   S
                               1230                                        1260

AGT GTT CCA GTG TGT TGT GAA CAA ATC TTT TGT CCA AGT CCT CCA GTT ATT CCT AAT GGG AGA
 S   V   P   V   C   C   E   Q   I   F   C   P   S   P   P   V   I   P   N   G   R
                               1290                                        1320

CAC ACA GGA AAA CCT CTG GAA GTC TTT CCC TTT GGA AAA GCA GTA AAT TAC ACA TGC GAC
 H   T   G   K   P   L   E   V   F   P   F   G   K   A   V   N   Y   T   C   D
                               1350                                        1380
```

FIG. 1C

```
                                                              1440
CCC CAC CCA GAC AGA GGG ACG AGC TTC GAC CTC ATT GGA GAG AGC ACC ATC CGC TGC ACA
 P   H   P   D   R   G   T   S   F   D   L   I   G   E   S   T   I   R   C   T
                                                              1500
AGT GAC CCT CAA GGG AAT GGG GTT TGG AGC AGC CCT GCC CCT CGC TGT GGA ATT CTG GGT
 S   D   P   Q   G   N   G   V   W   S   S   P   A   P   R   C   G   I   L   G
                                                              1560
CAC TGT CAA GCC CCA GAT CAT TTT CTG AAG TTG GCC AAA ACC CAA ACC AAT GCA TCT
 H   C   Q   A   P   D   H   F   L   K   L   A   K   T   Q   T   N   A   S
                                                              1620
GAC TTT CCC ATT GGG ACA TCT TTA GAT TAC GAA TGC CGT CCT GAG TAC TAC GGG AGG CCA
 D   F   P   I   G   T   S   L   D   Y   E   C   R   P   E   Y   Y   G   R   P
                                                              1680
TTC TCT ATC ACA TGT CTA GAT AAC CTG GTC TGG TCA AGT CCC AAA GAT GTC TGT AAA CGT
 F   S   I   T   C   L   D   N   L   V   W   S   S   P   K   D   V   C   K   R
                                                              1740
AAA TCA TGT AAA ACT CCT CCA GAT CCA GTG AAT GGC ATG GTG CAT GTG ATC ACA GAC ATC
 K   S   C   K   T   P   P   D   P   V   N   G   M   V   H   V   I   T   D   I
                                                              1800
CAG GTT GGA TCC AGA ATC AAC TAT TCT TGT ACT ACA GGG CAC CGA CTC ATT GGT CAC TCA
 Q   V   G   S   R   I   N   Y   S   C   T   T   G   H   R   L   I   G   H   S
```

FIG. 1D

FIG. 1E

```
                                                  1830                              1860
TCT GCT GAA TGT ATC CTC TCG GGC AAT GCT GCC CAT TGG AGC ACG AAG CCG CCA ATT TGT
 S   A   E   C   I   L   S   G   N   A   A   H   W   S   T   K   P   P   I   C
                                                  1890                              1920
CAA CGA ATT CCT TGT GGG CTA CCC ACC ATC GCC AAT GGA GAT TTC ATT AGC ACC AAC
 Q   R   I   P   C   G   L   P   T   I   A   N   G   D   F   I   S   T   N
                                                  1950                              1980
AGA GAG AAT TTT CAC TAT GGA TCA GTG GTG ACC TAC CGC TGC AAT CCT GGA AGC GGG
 R   E   N   F   H   Y   G   S   V   V   T   Y   R   C   N   P   G   S   G
                                                  2010                              2040
AGA AAG GTG TTT GAG CTT GTG GGT GAG CCC TCC ATA TAC TGC ATT ATA CCT AAT GAC GAT CAA
 R   K   V   F   E   L   V   G   E   P   S   I   Y   C   I   I   P   N   D   D   Q
                                                  2070                              2100
GTG GGC ATC TGG AGC GGC CCG GCC CCT CAG TGC ACC AGC ACC AAA TGC ACG CCT CCA
 V   G   I   W   S   G   P   A   P   Q   C   T   S   T   K   C   T   P   P
                                                  2130                              2160
AAT GTG GAA AAT GGA ATA TTG GTA TCT GAC AAC AGA AGC TTA TTT TCC TTA AAT GAA GTT
 N   V   E   N   G   I   L   V   S   D   N   R   S   L   F   S   L   N   E   V
                                                  2190                              2220
GTG GAG TTT AGG TGT CAG CCT GGC TTT GTC ATG AAA GGA CCC CGC CGT GTG AAG TGC CAG
 V   E   F   R   C   Q   P   G   F   V   M   K   G   P   R   R   V   K   C   Q
```

FIG. 1F

```
                                                        2280
GCC CTG AAC AAA TGG GAG CCG GAG CTA CCA AGC TGC TCC AGG GTA TGT CAG CCA CCT CCA
 A   L   N   K   W   E   P   E   L   P   S   C   S   R   V   C   Q   P   P   P
2250
                                                        2340
GAT GTC CTG CAT GCT GAG CGT ACC CAA AGG GAC AAG GAC AAC TTT TCA CCC GGG CAG GAA
 D   V   L   H   A   E   R   T   Q   R   D   K   D   N   F   S   P   G   Q   E
2310
                                                        2400
GTG TTC TAC AGC TGT GAG CCC GGC TAT GAC CTC AGA GGG GCT GCG TCT ATG CGC TGC ACA
 V   F   Y   S   C   E   P   G   Y   D   L   R   G   A   A   S   M   R   C   T
2370
                                                        2460
CCC CAG GGA GAC TGG AGC CCT GCA GCC CCC ACA TGT GAA AAA TCC TGT GAT GAC TTC
 P   Q   G   D   W   S   P   A   A   P   T   C   E   K   S   C   D   D   F
2430
                                                        2520
ATG GGC CAA CTT CTT AAT GGC CGT GTG CTA TTT CCA GTA AAT CTC CAG CTT GGA GCA AAA
 M   G   Q   L   L   N   G   R   V   L   F   P   V   N   L   Q   L   G   A   K
2490
                                                        2580
GTG GAT TTT GTT TGT GAT GAA GGA TTT CAA TTA AAA GGC AGT AGT GCT AGT TAT TGT GTC
 V   D   F   V   C   D   E   G   F   Q   L   K   G   S   S   A   S   Y   C   V
2550
                                                        2640
TTG GCT GGA ATG GAA AGC CTT TGG AAT AGC AGT GTT CCA GTG TGT GAA CAA ATC TTT TGT
 L   A   G   M   E   S   L   W   N   S   S   V   P   V   C   E   Q   I   F   C
2610
                                                        2700
CCA AGT CCT CCA GTT ATT CCT AAT GGG AGA CAC ACA GGA AAA CCT CTG GAA GTC TTT CCC
 P   S   P   P   V   I   P   N   G   R   H   T   G   K   P   L   E   V   F   P
2670
```

```
TTT GGA AAA GCA GTA AAT TAC ACA TGC CCC CAC CCA GAC AGA GGG ACG AGC TTC GAC
 F   G   K   A   V   N   Y   T   C   P   H   P   D   R   G   T   S   F   D
            2730                                                    2760

CTC ATT GGA GAG AGC ACC ATC CGC TGC ACA AGT GAC CCT CAA GGG AAT GGG GTT TGG AGC
 L   I   G   E   S   T   I   R   C   T   S   D   P   Q   G   N   G   V   W   S
            2790                                                    2820

AGC CCT GCC CCT CGC TGT GGA ATT CTG GGT CAC TGT CAA TTT CCC ATT GGG ACA TCT TTA
 S   P   A   P   R   C   G   I   L   G   H   C   Q   F   P   I   G   T   S   L
            2850                                                    2880

GCC AAG TTG AAA ACC CAA ACC AAT GCA TCT GAC TTT CCC ATT GGG ACA TCT TTA AAG TAC
 A   K   L   K   T   Q   T   N   A   S   D   F   P   I   G   T   S   L   K   Y
            2910                                                    2940

GAA TGC CGT CCT GAG TAC TAC GGG AGG CCA TTC TCT ATC ACA TGT CTA GAT AAC CTG GTC
 E   C   R   P   E   Y   Y   G   R   P   F   S   I   T   C   L   D   N   L   V
            2970                                                    3000

TGG TCA AGT CCC AAA GAT GTC TGT AAA CGT AAA ACT TGT AAA ACT CCT CCA GAT CCA GTG
 W   S   S   P   K   D   V   C   K   R   K   T   C   K   T   P   P   D   P   V
            3030                                                    3060

AAT GGC ATG GTG CAT GTG ATC ACA GAC ATC CAG GTT GGA TCC AGA ATC AAC TAT TCT TGT
 N   G   M   V   H   V   I   T   D   I   Q   V   G   S   R   I   N   Y   S   C
            3090                                                    3120
```

FIG. 1G

```
ACT ACA GGG CAC CGA CTC ATT GGT CAC TCA TCT GCT GAA TGT ATC CTC TCA GGC AAT ACT
 T   T   G   H   R   L   I   G   H   S   S   A   E   C   I   L   S   G   N   T
                                        3150                                3180

GCC CAT TGG AGC ACG AAG CCG CCA ATT TGT CAA CGA ATT CCT TGT GGG CTA CCC CCA ACC
 A   H   W   S   T   K   P   P   I   C   Q   R   I   P   C   G   L   P   P   T
                                        3210                                3240

ATC GCC AAT GGA GAT TTC ATT AGC ACC AAC AGA GAG AAT TTT CAC TAT GGA TCA GTG GTG
 I   A   N   G   D   F   I   S   T   N   R   E   N   F   H   Y   G   S   V   V
                                        3270                                3300

ACC TAC CGC TGC AAT CTT GGA AGC AGA GGG AGA AAG GTG TTT GAG CTT GTG GGT GAG CCC
 T   Y   R   C   N   L   G   S   R   G   R   K   V   F   E   L   V   G   E   P
                                        3330                                3360

TCC ATA TAC TGC ACC AGC AAT GAC GAT CAA GTG GGC ATC TGG GAA AAT GCC GCC CCT CAG
 S   I   Y   C   T   S   N   D   D   Q   V   G   I   W   E   N   A   A   P   Q
                                        3390                                3420

TGC ATT CCT AAC AAA TGC ACG CCT CCA AAT GTG GAG TTT AGG TGT CAG GGC ATA TTG GTA
 C   I   P   N   K   C   T   P   P   N   V   E   F   R   C   Q   G   I   L   V
                                        3450                                3480

AAC AGA AGC TTA TTT TCC TTA AAT GAA GTT GTG GAG TTT GTG GAG CCT TCT GAC TTT GTC
 N   R   S   L   F   S   L   N   E   V   V   E   F   V   E   P   S   D   F   V
                                        3510                                3540

ATG AAA GGA CCC CGC GTG AAG TGC CAG GCC CTG AAC AAA TGG GAG CCA GAG TTA CCA
 M   K   G   P   R   V   K   C   Q   A   L   N   K   W   E   P   E   L   P
                                        3570                                3600
```

FIG. 1H

```
AGC TGC TCC AGG GTG TGT CAG CCG CCT CCA GAA ATC CTG CAT GGT GAG CAT ACC CCA AGC
 S   C   S   R   V   C   Q   P   P   P   E   I   L   H   G   E   H   T   P   S
                                  3630                                      3660

CAT CAG GAC AAC TTT TCA CCT GGG CAG GAA GTG TTC TAC AGC TGT GAG CCT GGC TAT GAC
 H   Q   D   N   F   S   P   G   Q   E   V   F   Y   S   C   E   P   G   Y   D
                                  3690                                      3720

CTC AGA GGG GCT GCG TCT CTG CAC TGC ACA CCC CAG GGA GAC TGG AGC CCT GAA GCC CCG
 L   R   G   A   A   S   L   H   C   T   P   Q   G   D   W   S   P   E   A   P
                                  3750                                      3780

AGA TGT GCA GTG AAA TCC TGT GAT GAC TTC TTG GGT CAA GGC CGT GTG CTA
 R   C   A   V   K   S   C   D   D   F   L   G   Q   G   R   V   L
                                  3810                                      3840

TTT CCA CTT AAT CTC CAG CTT GGG GCA AAG GTG TCC TTT GTC TGT GAT GAA CTT TGG CGC
 F   P   L   N   L   Q   L   G   A   K   V   S   F   V   C   D   E   G   F   R
                                  3870                                      3900

TTA AAG GGC AGT TCC GTT AGT CAT TGT GTT GGA ATG AGA AGC CTT TGG AAT AAC
 L   K   G   S   S   V   S   H   C   V   G   M   R   S   L   W   N   N
                                  3930                                      3960

AGT GTT CCT GTG TGT GAA CAT ATC TTT TGT CCA AAT CCT CCA GCT ATC CTT AAT GGG AGA
 S   V   P   V   C   E   H   I   F   C   P   N   P   P   A   I   L   N   G   R
                                  3990                                      4020
```

FIG. 1I

FIG. 1J

```
        4050                                               4080
CAC ACA GGA ACT CCC TCT GGA GAT ATT CCC TAT GGA AAA GAA ATA TCT TAC ACA TGT GAC
 H   T   G   T   P   S   G   D   I   P   Y   G   K   E   I   S   Y   T   C   D 4110                                               4140
CCC CAC CCA GAC AGA GGG ATG ACC TTC AAC CTC ATT GGG GAG AGC ACC ATC CGC TGC ACA
 P   H   P   D   R   G   M   T   F   N   L   I   G   E   S   T   I   R   C   T 4170                                               4200
AGT GAC CCT CAT GGG AAT GGG GTT TGG AGC AGC CCT GCC CGC TGT GAA CTT TCT GTT
 S   D   P   H   G   N   G   V   W   S   S   P   A   R   C   E   L   S   V 4230                                               4260
CGT GCT GGT CAC TGT GAA CCT ACG ATC CCA ATT
 R   A   G   H   C   E   P   T   I   P   I 4290                                               4320
AAT GAC TTT GAG TTT CCA TTT GCC AGT CCT ACG ATC CCA ATT
 N   D   F   E   F   P   F   A   S   P   T   I   P   I 4350                                               4380
GGG AAA ATG TTC TCT ATC TCC ATC TCC ATC TGC CTA GAA CCC TTC TAT TCA AGT GTT CCT GGG TAT TTT
 G   K   M   F   S   I   S   I   C   L   E   P   F   Y   S   S   V   P   G   Y   F 4410                                               4440
TGT AGA CGA AAA TCA TGT GGA CCT CCA CCA GAA CCC TTC AAT GGA ATG GTG CAT ATA AAC
 C   R   R   K   S   C   G   P   P   P   E   P   F   N   G   M   V   H   I   N 4470                                               4500
ACA GAT ACA CAG TTT GGA TCA ACA GTT AAT TAT TCT TGT AAT GAA GGG TTT CGA CTC ATT
 T   D   T   Q   F   G   S   T   V   N   Y   S   C   N   E   G   F   R   L   I
```

FIG. 1K

```
GGT TCC CCA TCT ACT ACT TGT CTC GTC TCA GGC AAT AAT GTC ACA TGG GAT AAG AAG GCA
 G   S   P   S   T   T   C   L   V   S   G   N   N   V   T   W   D   K   K   A
                        4530                              4560
CCT ATT TGT GAG ATC ATA TCT TGT GAG CCA CCT CCA ACC ATA TCC AAT GGA GAC TTC TAC
 P   I   C   E   I   I   S   C   E   P   P   P   T   I   S   N   G   D   F   Y
                        4590                              4620
AGC AAC AAT AGA ACA TCT TTT CAC AAT GGA ACG GTG GTA ACT TAC CAG TGC CAC ACT GGA
 S   N   N   R   T   S   F   H   N   G   T   V   V   T   Y   Q   C   H   T   G
                        4650                              4680
CCA GAT GGA GAA CAG CTG TTT GAG CTT GTG GGA GAA CGG TCA ATA TAT TGC ACC AGC AAA
 P   D   G   E   Q   L   F   E   L   V   G   E   R   S   I   Y   C   T   S   K
                        4710                              4740
GAT CAA GTT GGT GTT TGG AGC AGC CCT CCC CCT CGG TGT ATT TCT ACT AAT AAA TGC
 D   Q   V   G   V   W   S   S   P   P   P   R   C   I   S   T   N   K   C
                        4770                              4800
ACA GCT CCA GAA AAT GCA ATT AGA GTA CCA GGA AAC AGG AGT TTC TTT TCC CTC
 T   A   P   E   N   A   I   R   V   P   G   N   R   S   F   F   S   L
                        4830                              4860
ACT GAG ATC ATC AGA TTT AGA TGT CAG CCC GGG TTT GTC ATG GTA GGG TCC CAC ACT GTG
 T   E   I   I   R   F   R   C   Q   P   G   F   V   M   V   G   S   H   T   V
                        4890                              4920
```

```
CAG TGC CAG ACC AAT GGC AGA TGG GGG CCC AAG CTG CCA CAC TGC TCC AGG GTG TGT CAG
 Q   C   Q   T   N   G   R   W   G   P   K   L   P   H   C   S   R   V   C   Q
                                    4950                                    4980

CCG CCT CCA GAA ATC CTG CAT GGT GAG CAT ACC CTA AGC CAC CAG GAC AAC TTT TCA CCT
 P   P   P   E   I   L   H   G   E   H   T   L   S   H   Q   D   N   F   S   P
                                    5010                                    5040

GGG CAG GAA GTG TTC TAC AGC TGT GAG CCC AGC TAT GAC CTC AGA GGG GCT GCG TCT CTG
 G   Q   E   V   F   Y   S   C   E   P   S   Y   D   L   R   G   A   A   S   L
                                    5070                                    5100

CAC TGC ACG CCC CAG GGA GAC TGG AGC CCT GAA GCC CCT AGA TGT ACA GTG AAA TCC TGT
 H   C   T   P   Q   G   D   W   S   P   E   A   P   R   C   T   V   K   S   C
                                    5130                                    5160

GAT GAC TTC CTG GGC CAA CTC CCT CAT GGC CGT GTG GGG TTC CTA CTT CCA AGA TGT CTT
 D   D   F   L   G   Q   L   P   H   G   R   V   G   F   L   L   P   R   C   L
                                    5190                                    5220

GGG GCA AAG GTG TCC TTT GTT TGC GAT GAA AAA GCC CTT TGG AAT AGC AGT GCT AGT CTT
 G   A   K   V   S   F   V   C   D   E   K   A   L   W   N   S   S   A   S   L
                                    5250                                    5280

CAT TGT GTC TTG GCT GGA ATG AAA GCC CTT ATC CTT AAT GGG AGA CAC ACA GGA ACA GTT
 H   C   V   L   A   G   M   K   A   L   I   L   N   G   R   H   T   G   T   V
                                    5310                                    5340

ATC TTT TGT CCA AAT CCT CCA GCT CTT AAT GGG AGA CAC ACA GGA ACT CCC TTT GGA
 I   F   C   P   N   P   P   A   L   N   G   R   H   T   G   T   P   F   G
                                    5370                                    5400
```

FIG. 1L

```
                                              5430                                              5460
GAT ATT CCC TAT GGA AAA GAA ATA TCT TAC GCA TGC GAC ACC CAC CCA GAC AGA GGG ATG
 D   I   P   Y   G   K   E   I   S   Y   A   C   D   T   H   P   D   R   G   M 5490                                              5520
ACC TTC AAC CTC ATT GGG GAG AGC TCC ATC CGC TGC ACA AGT GAC CCT CAA GGG AAT GGG
 T   F   N   L   I   G   E   S   S   I   R   C   T   S   D   P   Q   G   N   G 5550                                              5580
GTT TGG AGC AGC CCT GCC CGC TGT GAA CTT TCT GTT CCT GCT GAC AGT CCT CAT CCA
 V   W   S   S   P   A   R   C   E   L   S   V   P   A   D   S   P   H   P 5610                                              5640
CCC AAG ATC CAA AAC GGG CAT TAC ATT GGA CAC GTA TCT CTA TAT CTT CCT GGG ATG
 P   K   I   Q   N   G   H   Y   I   G   H   V   S   L   Y   L   P   G   M 5670                                              5700
ACA ATC AGC TAC ACT TGT GAC CCC GGC TAC CTG TTA GTG GGA AAG GGC TTC ATT TTC TGT
 T   I   S   Y   T   C   D   P   G   Y   L   L   V   G   K   G   F   I   F   C 5730                                              5760
ACA GAC CAG GGA ATC TGG AGC CAA TTG GAT CAT TAT TGC AAA GAA GTA AAT TGT AGC TTC
 T   D   Q   G   I   W   S   Q   L   D   H   Y   C   K   E   V   N   C   S   F 5790                                              5820
CCA CTG TTT ATG AAT GGA ATC TCG AAG GAG TTA GAA ATG AAA AAA GTA TAT CAC TAT GGA
 P   L   F   M   N   G   I   S   K   E   L   E   M   K   K   V   Y   H   Y   G
```

FIG. 1M

```
GAT TAT GTG ACT TTG AAG TGT GAA GAT GGG TAT ACT CTG GAA GGC AGT CCC TGG AGC CAG
 D   Y   V   T   L   K   C   E   D   G   Y   T   L   E   G   S   P   W   S   Q
                                        5850                                5880

TGC CAG GCG GAT GAC AGA TGG GAC CCT CCT CTG GCC AAA TGT ACC TCT CGT GCA CAT GAT
 C   Q   A   D   D   R   W   D   P   P   L   A   K   C   T   S   R   A   H   D
                                        5910                                5940

GCT CTC ATA GTT GGC ACT TTA TCT ACG ATC TTC TTT ATT TTA CTC ATC ATT TTC CTC
 A   L   I   V   G   T   L   S   T   I   F   F   I   L   L   I   I   F   L
                                        5970                                6000

TCT TGG ATA ATT CTA AAG CAC TCT CAA AGT ACT GGC AAT AAA AGG GAA AAC CCT AAA GAA GTG
 S   W   I   I   L   K   H   S   Q   S   T   G   N   K   R   E   N   P   K   E   V
                                        6030                                6060

GCT ATC CAT TTA CAT TCT CAA GGC AGC AGC GTT CAT CCC CGA ACT CTG CAA ACA AAT
 A   I   H   L   H   S   Q   G   S   S   V   H   P   R   T   L   Q   T   N
                                        6090                                6120

GAA GAA AAT AGC AGG GTC CTT CCT TGA CAA AGT ACT ATA CAG CTG AAG AAC ATC TCG AAT
 E   E   N   S   R   V   L   P   U   Q   S   T   I   Q   L   K   N   I   S   N
                                        6150                                6180

ACA ATT TTG GTG GGA AAG GAG CCA ATT GAT TTC AAC AGA ATC AGA TCT GAG CTT CAT AAA
 T   I   L   V   G   K   E   P   I   D   F   N   R   I   R   S   E   L   H   K
                                        6210                                6240

GTC TTT GAA GTG ACT CAG AGA CGC AGA CAT GTG CAC TTG AAG ATG CTG CCC CTT CCC
 V   F   E   V   T   Q   R   R   R   H   V   H   L   K   M   L   P   L   P
                                        6270                                6300
```

FIG. 1N

```
TGG TAC CTA GCA AAG CTC CTG CCT CTT TGT GTG CGT CAC TGT GAA ACC CCC ACC CTT CTG  6360
CCT CGT GCT AAA CGC ACA CAG TAT CTA GTC AGG GGA AAA GAC TGC ATT TAG GAG ATA GAA  6420
AAT AGT TTG GAT TAC TTA AAG GAA TAA GGT GTT GCC TGG AAT TTC TGG TTT GTA AGG TGG  6480
TCA CTG TTC TTT TTT AAA ATA TTT GTA ATA TGG AAT GGG CTC AGT AAG AAG AGC TTG GAA  6540
AAT GCA GAA AGT TAT GAA AAA TAA GTC ACT TAT AAT TAT GCT ACC TAC TGA TAA CCA CTC  6600
```

FIG. 10

```
                                                                    6660
CTA ATA TTT TGA TTC ATT TTC TGC CTA TCT TCT TTC ACA TAT GTG TTT TTT TAC ATA CGT
                                                                    6720
ACT TTT CCC CCC TTA GTT TGT TTC CTT TTA TTT TAT AGA GCA GAA CCC TAG TCT TTT AAA
                                                                    6780
CAG TTT AGA GTG AAA TAT ATG CTA TAT CAG TTT TTA CTT TCT CTA GGG AGA AAA ATT AAT
                                                                    6840
TTA CTA GAA AGG CAT GAA ATG ATC ATG GGA AGA GTG GTT AAG ACT ACT GAA GAG AAA TAT
                                                                    6900
TTG GAA AAT AAG ATT TCG ATA TCT TCT TTT TTT TTG AGA TGG AGT CTG GCT CTG TCT CCC

AGG CTG GAG TGC AGT GGC GTA ATC TCG GCT CAC TGC AAC GTC CGC CTC CCG
```

FIG. 1P

| | | |
|---:|:---|---:|
| 1 | CCAAGTTGAAAACCCAAACCAATGCATCTGACTTTCCCATTGGGACATCTTTAAAGTACG | 60 |
| 61 | AATGCCGTCCTGAGTACTACGGGAGGCCATTCTCTATCACATGTCTAGATAACCTGGTCT | 120 |
| 121 | GGTCAAGTCCCAAAGATGTCTGTAAACGTAAATCATGTAAAACTCCTCCAGATCCAGTGA | 187 |
| 181 | ATGGCATGGTGCATGTGATCACAGACATCCAGGTTGGATCCAGAATCAACTATTCTTGTA | 240 |
| 241 | CTACAGGGCACCGACTCATTGGTCACTCATCTGCTGAATGTATCCTCTCGGGCAATGCTG | 300 |
| 301 | CCCATTGGAGCACGAAGCCGCCAATTTGTCAACGAATTCCTTGTGGGCTACCCCCCACCA | 360 |
| 361 | TCGCCAATGGAGATTTCATTAGCACCAACAGAGAGAATTTTCACTATGGATCAGTGGTGA | 420 |
| 421 | CCTACCGCTGCAATCCTGGAAGCGGAGGGAGAAAGGTGTTTGAGCTTGTGGGTGAGCCCT | 480 |
| 481 | CCATATACTGCACCAGCAATGACGATCAAGTGGGCATCTGGAGCGGCCCGGCCCCTCAGT | 540 |
| 541 | GCATTATACCTAACAAATGCACGCCTCCAAATGTGGAAAATGGAATATTGGTATCTGACA | 600 |
| 601 | ACAGAAGCTTATTTTCCTTAAATGAAGTTGTGGAGTTTAGGTGTCAGCCTGGCTTTGTCA | 660 |
| 661 | TGAAAGGACCCCGCCGTGTGAAGTGCCAGGCCCTGAACAAATGGGAGCCGGAGCTACCAA | 720 |
| 721 | GCTGCTCCAGGGTATGTCAGCCACCTCCAGATGTCCTGCATGCTGAGCGTACCCAAAGGG | 780 |
| 781 | ACAAGGACAACTTTTCACCCGGGCAGGAAGTGTTCTACAGCTGTGAGCCCGGCTATGACC | 840 |
| 841 | TCAGAGGGGCTGCGTCTATGCGCTGCACACCCCAGGGAGACTGGAGCCCTGCAGCCCCCA | 900 |
| 901 | CATGTGAAGTGAAATCCTGTGATGACTTCATGGGCCAACTTCTTAATGGCCGTGTGCTAT | 960 |
| 961 | TTCCAGTAAATCTCCAGCTTGGAGCAAAAGTGGATTTTGTTTGTGATGAAGGATTTCAAT | 1020 |
| 1021 | TAAAAGGCAGCTCTGCTAGTTATTGTGTCTTGGCTGGAATGGAAAGCCTTTGGAATAGCA | 1080 |
| 1081 | GTGTTCCAGTGTGTGAACAAATCTTTTGTCCAAGTCCTCCAGTTATTCCTAATGGGAGAC | 1140 |
| 1141 | ACACAGGAAAACCTCTGGAAGTCTTTCCCTTTGGAAAAGCAGTAAATTACACATGCGACC | 1200 |
| 1201 | CCCACCCAGACAGAGGGACGAGCTTCGACCTCATTGGAGAGAGCACCATCCGCTGCACAA | 1260 |
| 1261 | GTGACCCTCAAGGGAATGGGGTTTGGAGCAGCCCTGCCCCTCGCTGTGGAATTCTGGGTC | 1320 |
| 1321 | ACTGTCAAGCCCCAGATCATTTTCTGTTTGCCAAGTTGAAAACCCAAACCAATGCATCTG | 1380 |
| 1381 | ACTTTCCCATTGGGACATCTTTAAAGTACGAATGCCGTCCTGAGTACTACGGGAGGCCAT | 1440 |
| 1441 | TCTCTATCACATGTCTAGATAACCTGGTCTGGTCAAGTCCCAAAGATGTCTGTAAACGTA | 1500 |

FIG. 3A

```
1501  AATCATGTAAAACTCCTCCAGATCCAGTGAATGGCATGGTGCATGTGATCACAGACATCC  1560
1561  AGGTTGGATCCAGAATCAACTATTCTTGTACTACAGGGCACCGACTCATTGGTCACTCAT  1620
1621  CTGCTGAATGTATCCTCTCAGGCAATACTGCCCATTGGAGCACGAAGCCGCCAATTTGTC  1680
1681  AACGAATTCCTTGTGGGCTACCCCCAACCATCGCCAATGGAGATTTCATTAGCACCAACA  1740
1741  GAGAGAATTTTCACTATGGATCAGTGGTGACCTACCGCTGCAATCTTGGAAGCAGAGGGA  1800
1801  GAAAGGTGTTTGAGCTTGTGGGTGAGCCCTCCATATACTGCACCAGCAATGACGATCAAG  1860
1861  TGGGCATCTGGAGCGGCCCCGCCCCTCAGTGCATTATACCTAACAAATGCACGCCTCCAA  1920
1921  ATGTGGAAAATGGAATATTGGTATCTGACAACAGAAGCTTATTTTCCTTAAATGAAGTTG  1980
1981  TGGAGTTTAGGTGTCAGCCTGGCTTTGTCATGAAAGGACCCCGCCGTGTGAAGTGCCAGG  2040
2041  CCCTGAACAAATGGGAGCCAGAGTTACCAAGCTGCTCCAGGGTGTGTCAGCCGCCTCCAG  2100
2101  AAATCCTGCATGGTGAGCATACCCCAAGCCATCAGGACAACTTTTCACCTGGGCAGGAAG  2160
2161  TGTTCTACAGCTGTGAGCCTGGCTATGACCTCAGAGGGGCTGCGTCTCTGCACTGCACAC  2220
2221  CCCAGGGAGACTGGAGCCCTGAAGCCCCGAGATGTGCAGTGAAATCCTGTGATGACTTCT  2280
2281  TGGGTCAACTCCCTCATGGCCGTGTGCTATTTCCACTTAATCTCCAGCTTGGGGCAAAGG  2340
2341  TGTCCTTTGTCTGTGATGAAGGGTTTCGCTTAAAGGGCAGTTCCGTTAGTCATTGTGTCT  2400
2401  TGGTTGGAATGAGAAGCCTTTGGAATAACAGTGTTCCTGTGTGTGAACATATCTTTTGTC  2460
2461  CAAATCCTCCAGCTATCCTTAATGGGAGACACACAGGAACTCCCTCTGGAGATATTCCCT  2520
2521  ATGGAAAAGAAATATCTTACACATGTGACCCCCACCCAGACAGAGGGATGACCTTCAACC  2580
2581  TCATTGGGGAGAGCACCATCCGCTGCACAAGTGACCCTCATGGGAATGGGGTTTGGAGCA  2640
2641  GCCCTGCCCCTCGCTGTGAACTTTCTGTTCGTGCTGGTCACTGTAAAACCCCAGAGCAGT  2700
2701  TTCCATTTGCCAGTCCTACGATCCCAATTAATGACTTTGAGTTTCCAGTCGGGACATCTT  2760
2761  TGAATTATGAATGCCGTCCTGGGTATTTTGGGAAAATGTTCTCTATCTCCTGCCTAGAAA  2820
2821  ACTTGGTCTGGTCAAGTGTTGAAGACAACTGTAGACGAAAATCATGTGGACCTCCACCAG  2880
```

FIG. 3B

```
2881  AACCCTTCAATGGAATGGTGCATATAAACACAGATACACAGTTTGGATCAACAGTTAATT  2940
2941  ATTCTTGTAATGAAGGGTTTCGACTCATTGGTTCCCCATCTACTACTTGTCTCGTCTCAG  3000
3001  GCAATAATGTCACATGGGATAAGAAGGCACCTATTTGTGAGATCATATCTTGTGAGCCAC  3060
3061  CTCCAACCATATCCAATGGAGACTTCTACAGCAACAATAGAACATCTTTTCACAATGGAA  3120
3121  CGGTGGTAACTTACCAGTGCCACACTGGACCAGATGGAGAACAGCTGTTTGAGCTTGTGG  3180
3181  GAGAACGGTCAATATATTGCACCAGCAAAGATGATCAAGTTGGTGTTTGGAGCAGCCCTC  3240
3241  CCCCTCGGTGTATTTCTACTAATAAATGCACAGCTCCAGAAGTTGAAAATGCAATTAGAG  3300
3301  TACCAGGAAACAGGAGTTTCTTTTCCCTCACTGAGATCATCAGATTTAGATGTCAGCCCG  3360
3361  GGTTTGTCATGGTAGGGTCCCACACTGTGCAGTGCCAGACCAATGGCAGATGGGGGCCCA  3420
3421  AGCTGCCACACTGCTCCAGGGTGTGTCAGCCGCCTCCAGAAATCCTGCATGGTGAGCATA  3480
3481  CCCTAAGCCATCAGGACAACTTTTCACCTGGGCAGGAAGTGTTCTACAGCTGTGAGCCCA  3540
3541  GCTATGACCTCAGAGGGGCTGCGTCTCTGCACTGCACGCCCCAGGGAGACTGGAGCCCTG  3600
3601  AAGCCCCTAGATGTACAGTGAAATCCTGTGATGACTTCCTGGGCCAACTCCCTCATGGCC  3660
3661  GTGTGCTACTTCCACTTAATCTCCAGCTTGGGGCAAAGGTGTCCTTTGTTTGCGATGAAG  3720
3721  GGTTCCGATTAAAAGGCAGGTCTGCTAGTCATTGTGTCTTGGCTGGAATGAAAGCCCTTT  3780
3781  GGAATAGCAGTGTTCCAGTGTGTGAACAAATCTTTTGTCCAAATCCTCCAGCTATCCTTA  3840
3841  ATGGGAGACACACAGGAACTCCCTTTGGAGATATTCCCTATGGAAAAGAAATATCTTACG  3900
3901  CATGCGACACCCACCCAGACAGAGGGATGACCTTCAACCTCATTGGGGAGAGCTCCATCC  3960
3961  GCTGCACAAGTGACCCTCAAGGGAATGGGGTTTGGAGCAGCCCTGCCCCTCGCTGTGAAC  4020
4021  TTTCTGTTCCTGCTGCCTGCCCACATCCACCCAAGATCCAAAACGGGCATTACATTGGAG  4080
4081  GACACGTATCTCTATATCTTCCTGGGATGACAATCAGCTACACTTGTGACCCCGGCTACC  4140
4141  TGTTAGTGGGAAAGGGCTTCATTTTCTGTACAGACCAGGGAATCTGGAGCCAATTGGATC  4200
4201  ATTATTGCAAAGAAGTAAATTGTAGCTTCCCACTGTTTATGAATGGAATCTCGAAGGAGT  4260
4261  TAGAAATGAAAAAAGTATATCACTATGGAGATTATGTGACTTTGAAGTGTGAAGATGGGT  4320
4321  ATACTCTGGAAGGCAGTCCCTGGAGCCAGTGCCAGGCGGATGACAGATGGGACCCTCCTC  4380
```

FIG. 3C

| | | |
|---|---|---|
| 4381 | TGGCCAAATGTACCTCTCGTGCACATGATGCTCTCATAGTTGGCACTTTATCTGGTACGA | 4440 |
| 4441 | TCTTCTTTATTTTACTCATCATTTTCCTCTCTTGGATAATTCTAAAGCACAGAAAAGGCA | 4500 |
| 4501 | ATAATGCACATGAAAACCCTAAAGAAGTGGCTATCCATTTACATTCTCAAGGAGGCAGCA | 4560 |
| 4561 | GCGTTCATCCCCGAACTCTGCAAACAAATGAAGAAAATAGCAGGGTCCTTCCT<u>TGA</u>CAAA | 4620 |
| 4621 | GTACTATACAGCTGAAGAACATCTCGAATACAATTTTGGTGGGAAAGGAGCCAATTGATT | 4680 |
| 4681 | TCAACAGAATCAGATCTGAGCTTCATAAAGTCTTTGAAGTGACTTCACAGAGACGCAGAC | 4740 |
| 4741 | ATGTGCACTTGAAGATGCTGCCCCTTCCCTGGTACCTAGCAAAGCTCCTGCCTCTTTGTG | 4800 |
| 4801 | TGCGTCACTGTGAAACCCCCACCCTTCTGCCTCGTGCTAAACGCACACAGTATCTAGTCA | 4860 |
| 4861 | GGGGAAAAGACTGCATTTAGGAGATAGAAAATAGTTTGGATTACTTAAAGGAATAAGGTG | 4920 |
| 4921 | TTGCCTGGAATTTCTGGTTTGTAAGGTGGTCACTGTTCTTTTTAAAATATTTGTAATAT | 4980 |
| 4981 | GGAATGGGCTCAGTAAGAAGAGCTTGGAAAATGCAGAAAGTTATGAAAAATAAGTCACTT | 5040 |
| 5041 | ATAATTATGCTACCTACTGATAACCACTCCTAATATTTTGATTCATTTCTGCCTATCTT | 5100 |
| 5101 | CTTTCACATATGTGTTTTTTTACATACGTACTTTTCCCCCCTTAGTTTGTTTCCTTTTAT | 5160 |
| 5161 | TTTATAGAGCAGAACCCTAGTCTTTTAAACAGTTTAGAGTGAAATATATGCTATATCAGT | 5220 |
| 5221 | TTTTACTTTCTCTAGGGAGAAAAATTAATTTACTAGAAAGGCATGAAATGATCATGGGAA | 5280 |
| 5281 | GAGTGGTTAAGACTACTGAAGAGAAATATTTGGAAATAAGATTTCGATATCTTCTTTTTT | 5340 |
| 5341 | TTTTGAGATGGAGTCTGGCTCTGTCTCCCAGGCTGGAGTGCAGTGGCGTAATCTCGGCTC | 5400 |
| 5401 | ACTGCAACGTCCGCCTCCCG 5420 | |

```
GTGCGTAAACTTGCGTTGGATCTTTCCCATGTCTGCAAAAGCTTCTTATGGAATTA
TTTCAAATGTGGGATATGAGAAACCTTTTCTGAAAAGTGTTCGGATAGATGGAT
```

FIG. 3D

```
B    1           KLKTQTNASDFPIGTSLKYECRPEYYGRPFSITCLDNLVWSSPKDVCK
C  439   GHCQAPDHFLFA
D  892   GHCKTPEQFPFASPTIPI   DFE V     N       G F KM    S  E           YE N  R

RKSCKTPPDPVNGMVHVITDIQVGSRINYSCTTGHRLIGHSSAECILSGNAAHWSTKPPI      108
                                                              T         558
            GP  E F       IN  T F   TV    NE F       SP TT LV   NVT DK  A   1011

B  109   CQRIPCGLPPTIANGDFISTNRENFHYGSVVTYRCNPGSGGRKVFELVGEPSIYCTSNDD
C  559                                  L R
D 1012   EI S EP    S      YN  TS  N  T    Q HT PD EQL       R        K

QVGIWSGPAPQCIIPNKCTPPNVENGILVSDNRSLFSLNEVVEFRCQPGFVMKGPRRVKC      228
                                                                        678
            V    SPR  ST    A E    A R PG  F     T  IIR         V SHT Q   1131

B  229   QALNKWEPELPSCSRVCQPPPDVLHAERTQRDKDNFSPGQEVFYSCEPGYDLRGAASHRC
C  879                      EI   G H PSHQ                         LH
D 1132   TNGR G K   H       EI   G H LSHQ       S                 LH

TPQGDWSPAAPTCEVKSCDDFMGQLLNGRVLFPVNLQLGAKVDFVCDEGFQLKGSSASYC      348
                 E  R A       L  PH       L       S       R    V H        798
                 E  R T       L  PH   L L         S       R  R  H        1251

B  349   VLAGMESLWNSSVPVCEQIFCPSPPVIPNGRHTGKPLEVFPFGKAVNYTCDPHPDRGTSF
C  799      V   R    N       H    N  A L       T SGDI  Y   EIS         MT
D 1252      KA                     N  A L       T FGDI  Y   EIS A   T   MT

DLIGESTIRCTSDPQGNGVWSSPAPRCGIL      438
            N                H          ELSVRA  891
            N      S                    ELS     1341

1342  VPAACPHPPKIQNGHYIGGHVSLYLPGMTISYTCDPGYLLVGKGFIFCTDQGIWSQLDHY

CKEVNCSFPLFMNGISKELEMKKVYHYGDYVTLKCEDGYTLEGSPWSQCQADDRWDPPLA    1461

1462  KCTSRAHDALIVGTLSGTIFFILLIIFLSWIILKHRKGNNAHENPKEVAIHLHSQGGSSV

HPRTLQTNEENSRVLP 1537
```

FIG.5B

| SCR NO. | | | | | | | |
|---|---|---|---|---|---|---|---|
| 1 | 1 | | KLKTQTNASDFPIGTSLKYECRPEYY | GRP F | | S ITC LD | N L VV SS PK DVC KR | 49 |
| 2 | 50 | KSCKTPPDPV NGMVHVIT | DIQVGSRINYSCTTGHRLIGH | | SSAECI LS GNA AHV STKP | PICQ R | 111 |
| 3 | 112 | IP CGLPPT IANGDFIS TNRENFHYGSVVTYRCNPGSG | GRKVFELVGEPS IYCTSNDD Q VGIV SG P APQCI | 181 |
| 4 | 182 | IPNK C TPPN YENGILVS DNRSLFSLNEVEFRCQPGFVMKGPRR | YKC | QALNKVE | PELPSCS R | 244 |
| 5 | 245 | V CQPPPD VLHA ERTQRDKDNFSPGGEV YSCEPGYDLRGAA | | S MRC T | PQ GDV S | PAAPTC E | 303 |
| 6 | 304 | V KSCDDFMGQLLNGRVLFPVNL | QLGAKYDFVCDEGFQLKGS | | SASYCV LA GME SLVNSS | YPVC EQ | 366 |
| 7 | 367 | IF CPSPPV IPNGRH TGKPLEVFPFGKAVNYTCDPHPD RGTS FDLIGE | STIRCTS D PQGNGVV SS P APRCG | 436 |
| 8 | 437 | ILGH CQAPDHFLF AKLKTQTNASDFPIGTSLKYECRPEYY GRP F | | S ITC LD | N L VV SS PK DVC KR | 499 |
| 9 | 500 | KSCKTPPDPV NGMVHVIT | DIQVGSRINYSCTTGHRLIGH | | SSAECI LS GNT AHV STKP | PICQ R | 561 |
| 10 | 562 | IP CGLPPT IANGDFIS TNRENFHYGSVVTYRCNLGS RGRKVFELVGEPS IYCTSNDD Q VGIV SG P APQCI | 631 |
| 11 | 632 | IPNK C TPPN VENGILVS DNRSLFSLNEVEFRCQPGFVMKGPRR | YKC | QALNKVE | PELPSCS R | 693 |
| 12 | 694 | V CQPPPE ILHGEH TPSHQDNFSPGQEVFYSCEPGYDLRGAA | | S LHC T | PQ GDV S | PEAPRCA | 752 |
| 13 | 753 | V KSCDDFLGQLPHGRVLPLNL | QLGAKVSFVCDEGFRLKGS | | SVSHCV LV GMR SLVNNS | VPVC EH | 816 |
| 14 | 817 | IF CPNPPA ILNGRH IGTPSGDIPYGKEISYTCDPHPD RGMT FNLIGE | STIRCTSDPHGN GVV SS P APRC ELSVRAG | 892 |
| 15 | 893 | HCKTPEQFPF ASPTIPINDFEFPYGTSLNYECRPGYF GKM F | | S ISC LE | N L VV SS VE DNCR R | 952 |
| 16 | 953 | KSCGPPPE PFNGMVHI NTDTQF GSTVNYSCNEGFRLIGSP | | STT C | LVSGNNV TV DKK APIC EI | 1014 |
| 17 | 1015 | I SCEPPPT ISNGDFYS NNRTSFHNGTVVTYQCHTGP DGEQLFELVGERS IYCTSKDD Q YGVV SS P PPRC | 1083 |
| 18 | 1084 | ISTNKCTAPE VENA IRVPGNRSFFSLTEIIRFRCQPGFVWGSH | | T VQC | QTNGRV G PKLPHCS R | 1146 |
| 19 | 1147 | V CQPPPE ILHGEH TLSHQDNFSPGGEVFYSCEPSYDLRGAA | | S LHC T | PQ GDV S | PEAPRCT | 1206 |
| 20 | 1207 | V KSCDDFLGQLPHGRVLPLNL | QLGAKVSFVCDEGFRLKGR | | SASHCV LA GMK ALVNSS | VPVC EQ | 1269 |
| 21 | 1270 | IF CPNPPA ILNGRH IGTPFGDIPYGKEISYACDTHPD RGMT FNLIGE | SSIRCTS D PQGNGVV SS P APRC ELS | 1341 |
| 22 | 1342 | VP AACPHPPK IQNG HYIGGHVSLYLPGMTISYTCDPGYLLYKG | FIFC T D | Q GIV SQLD HYCKE | 1404 |
| 23 | 1405 | VN CSFPLFM NGISKELEMKKVYHYGDYVTLKCEDGYTLEGSPV | | SQ C | QADDRVDP P LAKCTSR | 1466 |

FIG. 6A

```
AA #                                                                                                          LHR

1   MCLGRMGASSPRSPEPVGPPAPGLPFCCGGSLLAVVVLLALPVAWG                                                          SIGNAL

47   QCNAPEWLPFARPTNLTDEFEFPIGTYLNYECRPGYSGRPFSIICLKNSVWTGAKDRCRR                                             A
497   H Q  DHFL   KLKTQ NASD      S K      E Y        T  D L   SSP  V K                                      B
947   H Q  DHFL   KLKTQ NASD      S K      E Y        T  D L   SSP  V K                                      C
1400  H KT  QF     S   IPIND      V S            F KM      S  E L   SSVE N                                   D

107   KSCRNPPDPVNGMVHVIKGIQFGSQIKYSCTKGYRLIGSSSATCIISGDTVIVDNETPICDR                                          A
557        KT          TD   V  R N    T H      H    E L   NAAH STKP    Q                                    B
1007       KT          TD   V  R N    T H      H    E L   N AH STKP    Q                                    C
1460       GP  E F     INTDT    TVN   NE F       P  T LV  NN T  KKA   EI                                    D

169   IPCGLPPTITNGDFISTNRENFHYGSVVTYRCNPGSGGRKVFELVGEPSIYCTSNDDQVGIVSGPAPQCI                                  A
619                   A                                                                                     B
1069                  A                         L  R                                                        C
1522  S EP     S      Y N  TS  N T    Q HT PD EQL        R          K     V   S P R                         D

239   IPNKCTPPNVENGILVSDNRSLFSLNEVVEFRCQPGFVMKGPRRVKCQALNKWEPELPSCSR                                          A
689                                                                                                         B
1139                                                                                                        C
1592  ST    AE     A R PG    F    T IIR           V  SHT Q   TNGR G K   H                                   D

301   VCQPPPDVLHAERTQRDKDNFSPGQEVFYSCEPGYDLRGAASMRCTPQGDWSPAAPTCEV                                            A
751                                                                                                         B
1201        EI   G H PSHQ                         LH         E R A                                          C
1654        EI   G H LSHQ              S         ·LH         E R T                                          D

361   KSCDDFMGQQLLNGRVLFPVNLQLGAKVDFVCDEGFQLKGSSASYCVLAGMESLWNSSVPVCEQ                                        A
811                                                                                                         B
1261         L    PH   L         S        R      V H  V R    N      H                                       C
1714         L    PH   L L       S        R      R H     KA                                                 D

424   IFCPSPPVIPNGRHTGKPLEVFPFGKAVNYTCDPHPDRGTSFDLIGESTIRCTSDPQGNGVWSSPAPRCGI                                 A
874                                                                                                         B
1324       N  A L     T SGDI Y  EIS           MT N               H               EL                         C
1777       N  A L     T FGDI Y  EIS A  T      MT N       S                       EL                         D
```

FIG.10

FIG. 31A
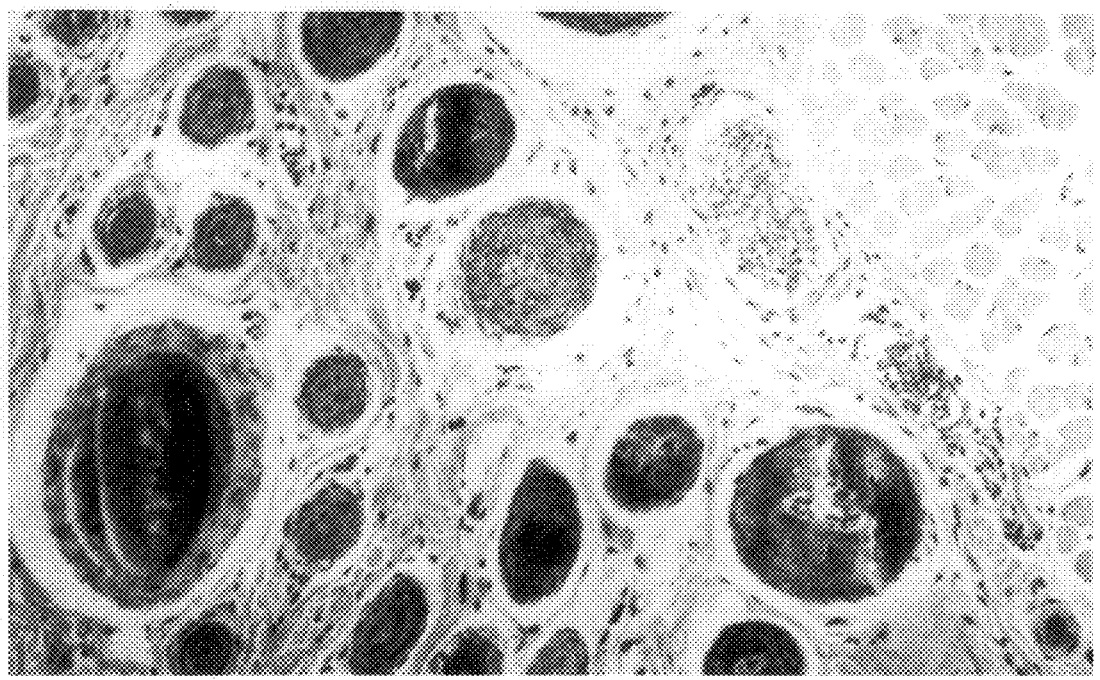
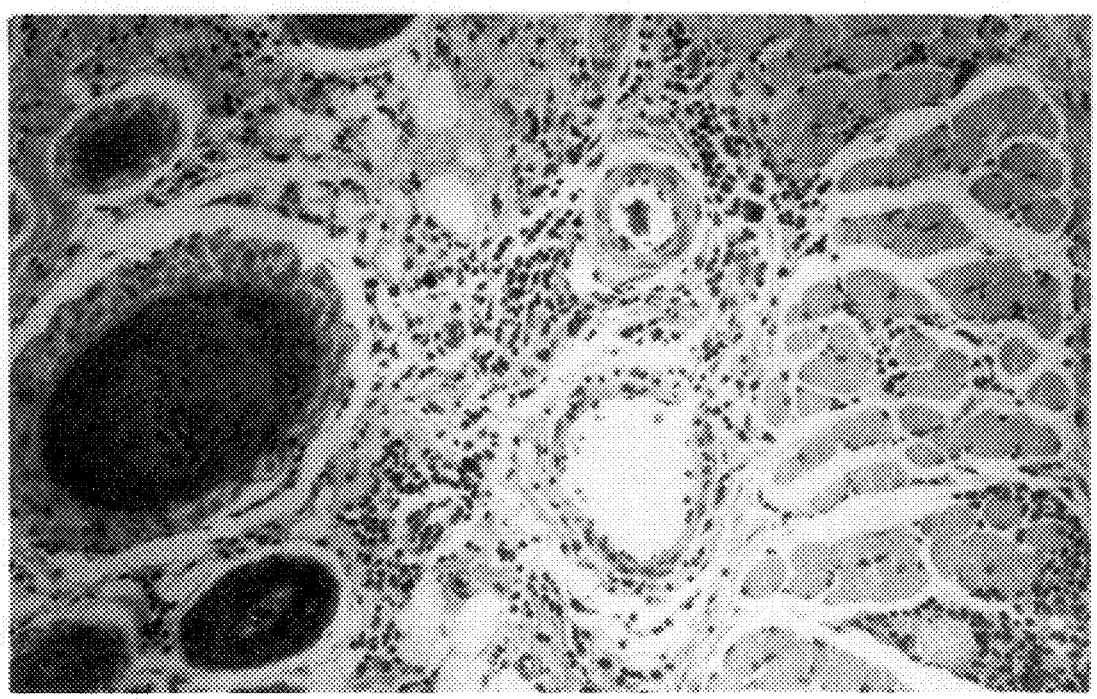
FIG. 31B

HUMAN C3B/C4B RECEPTOR (CR1)

This application is a continuation of Ser. No. 08/350,238, abandoned, filed Dec. 6, 1994, which is a continuation of Ser. No. 08/026,134, abandoned, filed Feb. 24, 1993, which is a division of Ser. No. 07/332,865, U.S. Pat. No. 5,212,071, filed Apr. 3, 1989, which is a continuation-in-part of Ser. No. 07/176,532, abandoned, filed Apr. 1, 1988, now abandoned.

TABLE OF CONTENTS

1. Introduction
2. Background of the Invention
   2.1. The Complement System
   2.2. The C3b/C4b Complement Receptor (CR.)
   2.3. Abnormalities of CR1 in Human Disease
3. Summary of the Invention
   3.1. Definitions
4. Description of the Figures
5. Detailed Description of the Invention
   5.1. Isolation of the CR1 Gene
   5.2. Expression of the Cloned CR1 Gene
   5.3. Identification and Purification of the Expressed Gene Product
   5.4. Structure of the CR1 Gene and Protein
      5.4.1. Genetic Analysis
      5.4.2. Protein Analysis
   5.5. CR1-Related Derivatives, Analogues, and Peptides
   5.6. Use of CR1
      5.6.1. Assays and Diagnosis
      5.6.2. Therapy
6. Example: The Cloning and Sequencing of the Human C3b/C4b Receptor (CR1)
   6.1. Materials and Methods
      6.1.1. Isolation and Sequence of CR1 Tryptic Peptides
      6.1.2. Isolation of cDNA Clones and Genomic Clones
      6.1.3. DNA Sequence Analysis
   6.2. Results
      6.2.1. Nucleotide Sequence of the CR1 Gene
      6.2.2. Analysis of the Nucleotide and Amino Acid Sequence of CR1
   6.3. Discussion
7. Example: CR1 5' cDNA Sequences Contain a Fourth Long Homologous Repeat
   7.1. Materials and Methods
      7.1.1. Construction of a cDNA Library
      7.1.2. Isolation of Clones, Probe, and DNA Sequence Analysis
   7.2. Results
   7.3. Discussion
8. Example: Expression of Recombinant Human CR1
   8.1. Construction of pBSABCD Containing the Entire CR1 Coding Sequence
   8.2. Construction and Assay of Plasmid piABCD, a Mammalian Expression Vector Containing the Entire CR1 Coding Sequence
   8.3. Expression of CR1 Fragments
      8.3.1. Construction of Deletion Mutants piBCD, piABD, piACD, piAD, pi8D, piCD and piD
      8.3.2. Contraction of Deletion Mutants piPl, piE1, piE2, piE-2, piU1, piU-2 and piA/D
9. Example: Identification of C3b and C4b Binding Domains
   9.1. Assays and Results
   9.2. Discussion
10. Example: Demonstration of Factor I Cofactor Activity
11. Example: Expression of Recombinant Soluble CR1
    11.1. Material and Methods
       11.1.1. Enzyme Digestions
       11.1.2. DNA Fragment Isolations
       11.1.3. Transfection into Mammalian Cells
       11.1.4. CHO Transfectant Cell Culture
       11.1.5. ELISA for the Detection of CR1 Levels

TABLE OF CONTENTS-continued 11.1.5.1. CR1 Standards
          11.1.5.2. CR1 ELISA
    11.2. Genetic Modifications of CR1 Coding Sequences
       11.2.1. Construction of pBSCR1c
       11.2.2. Construction of pBSCR1s
       11.2.3. Construction of pBM-CR1c
       11.2.4. Construction of Deletion Mutants pT-CR1c1, pT-CR1c2, pT-CR1c3, pT-CR1c4, and pT-CR1c5
          11.2.4.1. pT-CR1c1
          11.2.4.2. pT-CR1c2
          11.2.4.3. pT-CR1c3
          11.2.4.4. pT-CR1c4
          11.2.4.5. pT-CR1c5
    11.3. Expression of Soluble CR1
       11.3.1. Construction of pTCS Series of Expression Vectors
          11.3.1.1. Construction of pEAXgpt
          11.3.1.2. Construction of pMLEgpt
          11.3.1.3. Construction of pTCSgpt
          11.3.1.4. Construction of pTCSdhfr
          11.3.1.S. Construction of pTCSneo
       11.3.2. Expression and Assay of Plasmids pBSCR1c, pBSCR1s and pBM-CR1c, Mammalian Expression Vectors Containing Soluble CR1 Coding Sequences
          11.3.2.1. Expression of CR1 Construct Truncated at Different Positions Within the CR1 cDNA
          11.3.2.2. Expression of sCR1c in Two Different Expression Systems
       11.3.3. Expression and Assay of Plasmids pT-CR1cl, pT-CR1c2, pT-CR1c3, pT-CR1c4, and pT-CR1c5, Mammalian Expression Vectors Containing Soluble CR1 Coding Sequences
12. Example: Production and Purification of Soluble CR1
    12.1. Large Scale Production of Soluble CR1
       12.1.1. Production of sCR1 in Serum-Free Media
       12.1.2. Conclusions
    12.2. Purification of Soluble CR1
       12.2.1. Antibody Affinity-Column Purification
          12.2.1.1. Methods
          12.2.1.2. Results
       12.2.2. CR1 Purification by HPLC
          12.2.2.1. Methods
             12.2.2.1.1. Starting Material
             12.2.2.1.2. Cation Exchange HPLC Procedure
             12.2.2.1.3. Anion Exchange HPLC Procedure
             12.2.2.1.4. Western Blot Analysis.
          12.2.2.2. Results
          12.2.2.3. Characterization of Purified Soluble CR1
          12.2.2.4. Conclusions
13. Example: Demonstration of In Vitro Activity of Soluble CR1
    13.1. Inhibition of the Neutrophil Oxidative Burst
       13.1.1. Materials and Methods
          13.1.1.1. Materials
          13.1.1.2. Preparation of Neutrophils
          13.1.1.3. Preparation of Yeast Particles
          13.1.1.4. Activation of Neutrophils by Purified C5a
          13.1.1.5. Activation of Neutrophils by Purified C5a in Human Serum or Plasma
          13.1.1.6. Activation of Neutrophil by Yeast Particle-Activated Human Serum or Plama

TABLE OF CONTENTS-continued 13.1.2. Results
    13.1.2.1. C5a Induces an Oxygen Burst in Human Neutrophils Which Can be Measured Using DCFDA
    13.1.2.2. Human Serum Blocks the Oxygen Burst Effects of Purified C5a on Neutrophils
    13.1.2.3. Heparinized Plasma does not Block the Effects of C5a on Neutrophils
    13.1.2.4. sCR1 Present During Complement Activation Block C5a Generation
13.2. Inhibition of Complement Mediated Hemolysis
    13.2.1. Methods
    13.2.2. Results
13.3. Inhibition of C3a and C5a Production
    13.3.1. Methods
    13.3.2. Results
14. Example: Demonstration of Functional In Vivo Therapeutic Activity of Soluble CR1
    14.1. Soluble CR1 Demontrate In Vivo Function in a Reversed Passive Arthus Reaction
        14.1.1. Materials and Methods
        14.1.2. Results
        14.1.3. Effect of Intradermal Administration of Soluble CR1
    14.2. Pharmacokinetics of In Vivo Administered sCR1
    14.3. sCR1 Reduces Infarct Size in Rats with Reperfused Infarcted Myocardium
        14.3.1. Methods
            14.3.1.1. Induction of Rat Myocardial Infarct
            14.3.1.2. Morphological Analysis of Experimental Infarcts: Preparation of Heart for Study
        14.3.2. Results
        14.3.3. Conclusions
15. Deposit of Microorganisms

1. INTRODUCTION

The present invention relates to the C3b/C4b receptor (CR1) gene and its encoded protein. The invention also relates to CR1 nucleic acid sequences and fragments thereof comprising 70 nucleotides, and their encoded peptides or proteins comprising 24 amino acids. The invention also provides for the expression of the CR1 protein and fragments thereof. The CR1 nucleic acids and proteins have use in the diagnosis or therapy of disorders involving complement activity, and various inflammatory and immune disorders.

2. BACKGROUND OF THE INVENTION

2.1. The Complement System

The complement system is a group of proteins that constitutes about 10 percent of the globulins in the normal serum of humans (Hood, L. E., et al., 1984, Immunology, 2d Ed., The Benjamin/cummings Publishing Co., Menlo Park, Calif., p. 339). Complement (C) plays an important role in the mediation of immune and allergic reactions (Rapp, H. J. and Borsos, T, 1970, Molecular Basis of Complement Action, Appleton-Century-Crofts (Meredith), New York). The activation of complement components leads to the generation of a group of factors, including chemotactic peptides that mediate the inflammation associated with complement-dependent diseases. The sequential activation of the complement cascade may occur via the classical pathway involving antigen-antibody complexes, or by an alternative pathway which involves the recognition of certain cell wall polysaccharides. The activities mediated by activated complement proteins include lysis of target cells, chemotaxis, opsonization, stimulation of vascular and other smooth muscle cells, and functional aberrations such as degranulation of mast cells, increased permeability of small blood vessels, directed migration of leukocytes, and activation of B lymphocytes and macrophages (Eisen, H. N., 1974, Immunology, Harper & Row Publishers, Inc. Hagerstown, Maryland, p. 512).

During proteolytic cascade steps, biologically active peptide fragments, the anaphylatoxins C3a, C4a, and C5a (See WHO Scientific Group, 1977, WHO Tech. Rep. Ser. 606: 5 and references cited therein), are released from the third (C3), fourth (C4), and fifth (C5) native complement components (Hugli, T. E., 1981, CRC Crit. Rev. Immunol. 1: 321; Bult, H. and Herman, A. G., 1983, Agents Actions 13: 405).

2.2. The C3b/C4b Complement Receptor (CR1)

The human C3b/C4b receptor, termed CR1, is present on erythrocytes, monocytes/macrophages, granulocytes, B cells, some T cells, splenic follicular dendritic cells, and glomerular podocytes (Fearon, D. T., 1980, J. Exp. Med. 152: 20, Wilson, J. G., et al., 1983, J. Immunol. 131: 684; Reynes, M., et al., 1985, J. Immunol. 135: 2687; Gelfand, M. C., et al., 1976, N. Engl. J. Med. 295: 10; Kazatchkine, M. D., et al., 1982, Clin. Immunol. Immunopathol. 27: 170). CR1 specifically binds C3b, C4b, and iC3b. A soluble form of the receptor has been found in plasma that has ligand binding activity and the same molecular weight as membrane-associated CR1 (Yoon, S. H. and Fearon, D. T. 1985, J. Immunol. 134: 3332). CR1 binds C3b and C4b that have covalently attached to immune complexes and other complement activators, and the consequences of these interactions depend upon the cell type bearing the receptor (Fearon, D. T. and Wong, W. W., 1983, Ann. Rev. Immunol. 1: 243). Erythrocyte CR1 binds immune complexes for transport to the liver (Cornacoff, J. B., et al., 1983, J. Clin. Invest. 71: 236; Medof, M. E., et al., 1982, J. Exp. Med. 156: 1739) CR1 on neutrophils and monocytes internalizes bound complexes, either by adsorptive endocytosis through coated pits (Fearon, D. T., et al., 1981, J. Exp. Med. 153: 1615; Abrahamson, D. R. and Fearon, D. T., 1983, Lab. Invest. 48: 162) or by phagocytosis after activation of the receptor by phorbol esters, chemotactic peptides, or proteins that are present in the extracellular matrix, such as fibronectin and laminin (Newman, S.L., et al., 1980, J. Immunol. 125: 2236; Wright, S. D. and Silverstein, S. C., 1982, J. Exp. Med. 156: 1149; Wright, S. D., et al., 1983, J. Exp. Med. 158: 1338). Phosphorylation of CR1 may have a role in the acquisition of phagocytic activity (Changelian, P. S. and Fearon, D. T., 1986, J. Exp. Med. 163: 101). The function of CR1 on B lymphocytes is less defined, although treatment of these cells with antibody to CR1 enhanced their response to suboptimal doses of pokeweed mitogen (Daha, M. R., et al., 1983, Immunobiol. 164: 227 (Abstr.)). CR1 on follicular dendritic cells may subserve an antigen presentation role (Klaus, G. G. B., et al., 1980, Immunol. Rev. 53: 3).

CR1 can also inhibit the classical and alternative pathway C3/C5 convertases and act as a cofactor for the cleavage of C3b and C4b by factor I, indicating that CR1 also has complement regulatory functions in addition to serving as a receptor (Fearon, D. T., 1979, Proc. Natl. Acad. Sci. U.S.A. 76: 5867; Iida, K. and Nussenzweig, V., 1981, J. Exp. Med. 153: 1138). In the alternative pathway of complement activation, the bimolecular complex C3b,Bb is a C3 activating enzyme (convertase). CR1 (and factor H, at higher concentrations) can bind to C3b and can also promote the dissociation of C3b,Bb. Furthermore, formation of C3b,CR1

(and C3b,H) renders C3b susceptible to irreversible proteolytic inactivation by factor I, resulting in the formation of inactivated C3b (iC3b). In the classical pathway of complement activation, the complex C4b,2a is the C3 convertase. CR1 (and C4 binding protein, C4bp, at higher concentrations) can bind to C4b, and can also promote the dissociation of C4b,2a. The binding renders C4b susceptible to irreversible proteolytic inactivation by factor I through cleavage to C4c and C4d (inactivated complement proteins.)

CR1 is a glycoprotein composed of a single polypeptide chain. Four allotypic forms of CR1 have been found, differing by increments of ~40,000–50,000 daltons molecular weight. The two most common forms, the F and S allotypes, also termed the A and B allotypes, have molecular weights of 250,000 and 290,000 daltons (Dykman, T. R., et al., 1983, Proc. Natl. Acad. Sci. U.S.A. 80: 1698; Wong, W. W., et al., 1983, J. Clin. Invest. 72: 685), respectively, and two rarer forms have molecular weights of 210,000 and >290,000 daltons (Dykman, T. R., et al., 1984, J. Exp. Med. 159: 691; Dykman, T. R., et al., 1985, J. Immunol. 134: 1787). These differences apparently represent variations in the polypeptide chain of CR1, rather than glycosylation state, because they were not abolished by treatment of purified receptor protein with endoglycosidase F (Wong, W. W., et al., 1983, J. Clin. Invest. 72: 685), and they were observed when receptor allotypes were biosynthesized in the presence of tunicamycin (Lublin, D. M., et al., 1986, J. Biol. Chem. 261: 5736). All four CR1 allotypes have C3b-binding activity (Dykman, T. R., et al., 1983, Proc. Natl. Acad. Sci. U.S.A. 80: 1698; Wong, W. W., et al., 1983, J. Clin. Invest. 72: 685; Dykman, T. R., et al., 1984, J. Exp. Med. 159: 691; Dykman T. R., et al., 1985, J. Immunol. 134: 1787).

Two nonoverlapping restriction fragments of a CR1 cDNA were shown to crosshybridize under conditions of high stringency (Wong, W. W., et al., 1985, Proc. Natl. Acad. Sci. U.S.A. 82: 7711). Both cDNA probes also hybridized to multiple restriction fragments of genomic DNA, most of which were common to both probes (id.). The existence of repetitive coding sequences within CR1 was confirmed by sequence comparisons (Klickstein, L. B., et al., 1985, Complement 2: 44 (Abstr.)). In addition, the CR1 gene has been shown to have repetitive intervening sequences by the demonstration of crosshybridization of a genomic probe lacking coding sequences to several genomic restriction fragments (Wong, W. W., et al., 1986, J. Exp. Med. 164: 1531). Further, DNA from an individual having the larger S allotype had an additional restriction fragment hybridizing to this genomic probe when compared with DNA from an individual having the F allotype, suggesting that duplication of genomic sequences occurred in association with the higher molecular weight CR1 allele (id.).

CR1 has been shown to have homology to complement receptor type 2 (CR2) (Weis, J. J., et al., 1986, Proc. Natl. Acad. Sci. U.S.A. 83: 5639–5643).

2.3. Abnormalities of CR1 in Human Disease

Diminished expression of CR1 on erythrocytes of patients with systemic lupus erythematosus (SLE) has been reported by investigators from several geographic regions, including Japan (Miyakawa et al., 1981, Lancet 2: 493–497; Minota et al., 1984, Arthr. Rheum. 27: 1329–1335), the United States (Iida et al., 1982, J. Exp. Med. 155: 1427–1438; Wilson et al., 1982, N. Engl. J. Med. 307: 981–986) and Europe (Walport et al., 1985, Clin. Exp. Immunol. 59: 547; Jouvin et al., 1986, Complement 3: 88–96; Holme et al., 1986, Clin. Exp. Immunol. 63: 41–48). Taken as a group, patients have an average number of receptors per cell that is 50–60% that of normal populations. An early report noted that CR1 number on erythrocytes varied inversely with disease activity, with lowest numbers occurring during periods of most severe manifestations of SLE, and higher numbers being observed during periods of remission in the same patient (Iida et al., 1982, J. Exp. Med. 155: 1427–1438). CR1 number has also been found to correlate inversely with serum levels of immune complexes, with serum levels of C3d, and with the amounts of erythrocyte-bound C3dg, perhaps reflecting uptake of complement-activating immune complexes and deposition on the erythrocyte as an "innocent bystander" (Ross et al., 1985, J. Immunol. 135: 2005–2014; Holme et al., 1986, Clin. Exp. Immunol. 63: 41–48; Walport et al., 1985, Clin. Exp. Immunol. 59: 547). A patient with SLE lacking CR1 on erythrocytes was found to have an auto-antibody to CR1 (Wilson et al., 1985, J. Clin. Invest. 76: 182–190). Decreased titers of the anti-CR1 antibody coincided with improvement of the patient's clinical condition and with partial reversal of the receptor abnormality. Anti-CR1 antibody has been detected in two other SLE patients (Cook et al., 1986, Clin. Immunol. Immunopathol. 38: 135–138). Recently, acquired loss of erythrocyte CR1 in the setting of active SLE and hemolytic anemia was demonstrated by observing the rapid loss of the receptor from transfused erythrocytes (Walport et al., 1987, Clin. Exp. Immunol. 69: 501–507).

The relative loss of CR1 from erythrocytes has also been observed in patients with Human Immunodeficiency Virus (HIV) infections (Tausk, F.A., et al., 1986, J. Clin. Invest. 78: 977–982) and with lepromatus leprosy (Tausk, F. A., et al., 1985, J. Invest. Dermat. 85: 58s–61s).

Abnormalities of complement receptor expression in SLE are not limited to erythrocyte CR1. Relative deficiencies of total cellular CR1 of neutrophils and plasma membrane CR1 of B lymphocytes of the SLE patients have been shown to occur (Wilson et al., 1986, Arthr. Rheum. 29: 739747).

In patients with Type IV SLE nephritis, all detectable CR1 antigen is lost from podocytes, whereas in less severe forms of SLE nephritis and in non-SLE types of proliferative nephritis, including membranoproliferative glomerulonephritis Types I and II, CR1 expression on glomerular podocytes does not differ from normal (Kazatchkine et al., 1982, J. Clin. Invest. 69: 900–912; Emancipator et al., 1983, Clin. Immunol. Immunopathol. 27: 27: 170–175). However, patients having Type IV SLE nephritis do not have fewer numbers of erythrocyte CR1 than do SLE patients having other types of renal lupus or no nephritis (Jouvin et al., 1986, Complement 3: 88–96).

In vivo complement activation up-regulates CR1 expression at the plasma membrane of neutrophils (Lee, J., et al., 1984, Clin. Exp. Immunol. 56: 205–214; Moore, F. D., Jr., et al., 1986, N. Engl. J. Med. 314: 948–953).

3. SUMMARY OF THE INVENTION

The present invention relates to the C3b/C4b receptor (CR1) gene and its encoded protein. The invention also relates to CR1 nucleic acid sequences and fragments thereof comprising 70 nucleotides and their encoded peptides or proteins comprising 24 amino acids. The invention further provides for the expression of the CR1 protein and fragments thereof. The genes and proteins of the invention have uses in diagnosis and therapy of disorders involving complement activity, and various immune system or inflammatory disorders.

In specific embodiments of the present invention detailed in the examples sections infra, the cloning, nucleotide sequence, and deduced amino acid sequence of a full-length CR1 cDNA and fragments thereof are described. The expression of the CR1 protein and fragments thereof is also described. Expression of the CR1 protein and its fragments which contain binding sites for C3b and/or C4b, and which exhibit factor I cofactor activity, is obtained.

Also described in the examples infra are the production and purification of soluble CR1 molecules, which molecules are shown to be therapeutically useful for the treatment of inflammatory reactions and in the reduction of myocardial infarct size and prevention of reperfusion injury.

3.1. DEFINITIONS

| | |
|---|---|
| Ad2 MLP = | adenovirus 2 major late promoter |
| C = | complement |
| C3(ma) = | methylamine-treated C3 |
| C4bp = | C4 binding protein |
| CMV = | cytomegalovirus |
| CR1 = | complement receptor type 1, the C3b/C4b receptor |
| CR2 = | complement receptor, type 2 |
| DCFDA = | dichlorofluorescin diacetate |
| HPLC = | high performance liquid chromatography |
| ic3b = | inactivated C3b |
| LHR = | long homologous repeat |
| mAb = | monoclonal antibody |
| PAGE = | polyacrylamide gel electrophoresis |
| RPAR = | reverse passive Arthrus reaction |
| SCR = | short consensus repeat |
| sCR1 = | qsoluble CR1 molecule |

Pursuant to the provisions of 35 U.S.C. §202(c), it is hereby acknowledged that the Government has certain rights in this invention, which was made in part with funds from the National Institutes of Health.

4. DESCRIPTION OF THE FIGURES

FIG. 1(A through P). Nucleotide and amino acid sequence of the entire CR1 coding region. The sequence begins with the first nucleotide following the octamer EcoRI linker in clone λT109.1. Nucleotide number 1531 of this sequence is the first nucleotide 5' of nucleotide number 1 of the sequence depicted in FIGS. 3A–3D. The strand corresponding to the mRNA is shown, with the deduced amino acid sequence presented below. The putative signal sequence encoded by nucleotide numbers 28–147 is bracketed.

FIG. 2. Restriction map of 5.5 kb of human CR1 cDNA. The black bar indicates the cDNA, restriction sites are H, HindIII; B, BamHI; R, EcoRI; P, PstI; A, ApaI; S, SacI; G, BglII; K, KpnI. The cDNA clones from which the sequence was derived are shown below the map. The arrows indicate the direction and extent of sequence analysis by the dideoxy-nucleotide chain termination method. cDNA clones were oriented on the basis of restriction maps and overlapping sequence identity.

FIG. 3(A through D). Nucleotide sequence of 5.5 kb of human CR1 cDNA. The strand corresponding to the mRNA is shown and base number 1 (corresponding to base number 1532 of FIG. 1D is the first base after the EcoRI linker in the most 5' clone. The stop codon is underlined. The 110-bp sequence in the box was found between nucleotides 147 and 148 (arrow) and is believed to represent a portion of an intervening sequence.

Figure 4:
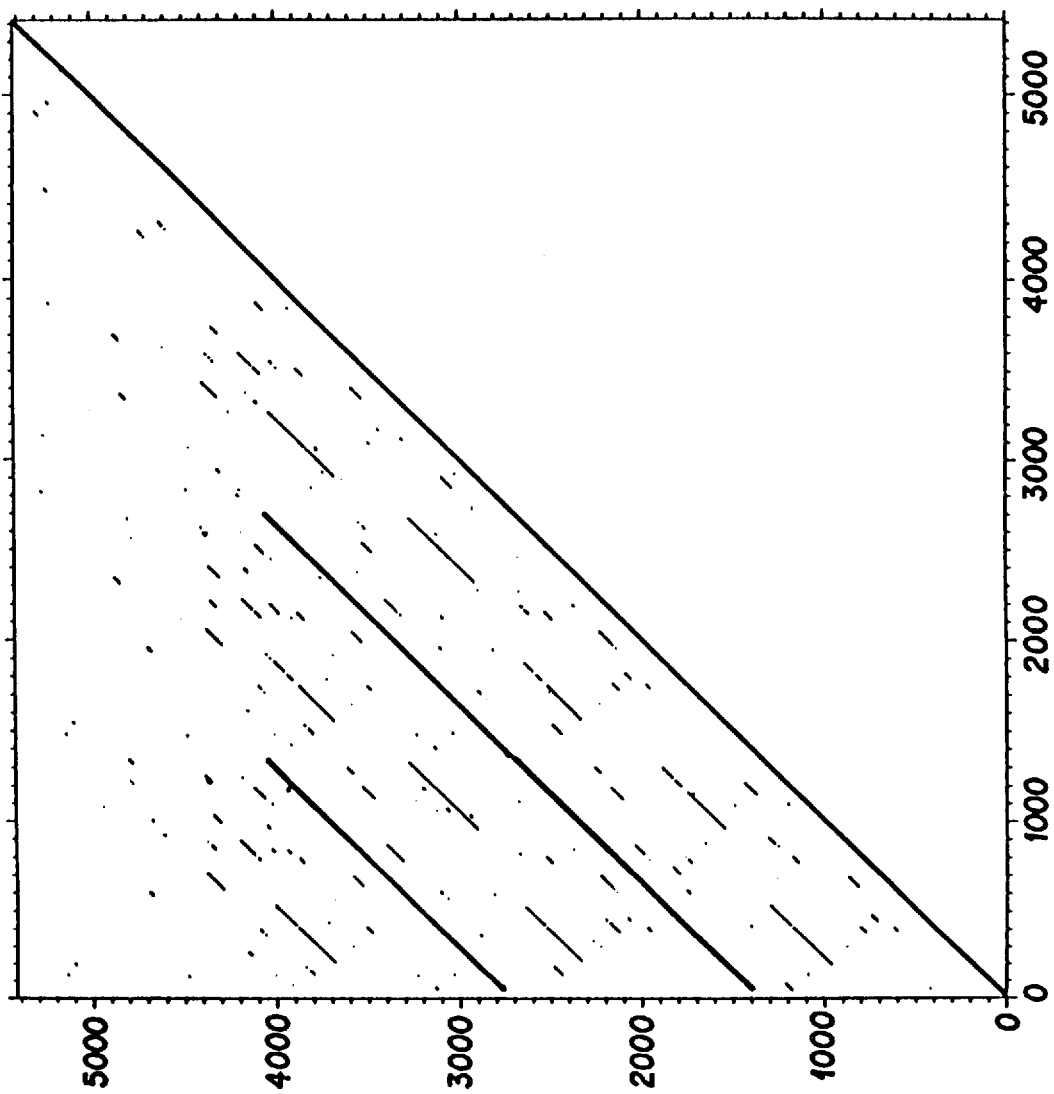

FIG. 4. Dot matrix analysis of the nucleotide sequence of 5.5 kb of human CR1 cDNA. A dot was plotted if there was at least a 40 bp of 90 bp match. The dark line bisecting the square diagonally indicates the identity of the sequence with itself. The two additional parallel dark lines 1.35 and 2.7 kb from the line of identity represent two tandem, direct long homologous repeats (LHRs) of 1.35 kb each. The six lighter, dashed lines between two LHRs correspond to short consensus repeats of ~0.2 kb. The short consensus repeats (SCRs) extend 0.4 kb beyond the long homologous repeats.

Figure 5A:
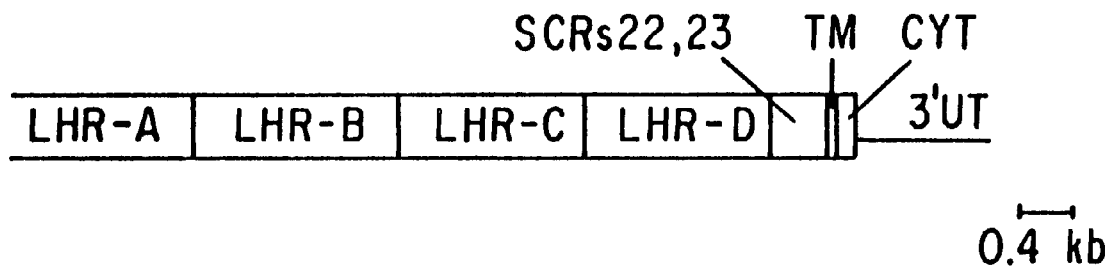

FIG. 5(A through C). (A) A schematic diagram of the CR1 protein. (TM) transmembrane region, (CYT) cytoplasmic region, (3'UT)3' untranslated sequence. Deduced amino acid sequence of human CR1. Each residue is shown in the one letter code (Lehninger, A. L., 1975, Biochemistry, 2d Ed., Worth Publishers, Inc., New York, p. 72). The residues in the long homologous repeats have been aligned to illustrate their homology. All the residues in LHR-B are shown, and a residue is given for LHR-C and LHR-D only where it is different from that in LHR-B. A hydropathy profile is aligned under the COOH-terminus of the protein to illustrate the presumptive transmembrane region. A stretch of four positively charged residues immediately after the hydrophobic sequence is overlined. The six amino acid sequence with 67% homology to the site of protein kinase C phosphorylation in the epidermal growth factor receptor is underlined.

FIG. 6(A through B). (A) Alignment of the SCRs of CR1. The repeats are numbered 1–23 from $NH_2$-terminal to COOH-termnal. Spaces have been introduced to maximize the alignment. The boxes represent invariant residues and the vertical arrows indicate positions of amino acid conservation. A residue is deemed conserved if it, or a conservative substitution, is present in at least half of the SCRs. The horizontal arrow indicates an SCR that was also sequenced from CR1 genomic clone 2.38 and is encoded by a single exon. (B) Restriction map, sequencing strategy, and partial sequence of genomic clone λ2.38. The restriction sites are: (B) BamHI, (S) SacI, (E) EcoRV, (K) KpnI, (P) PstI. The horizontal arrow indicates direction and extent of sequencing and the vertical arrows indicate the exon-intron boundaries.

Figure 7:
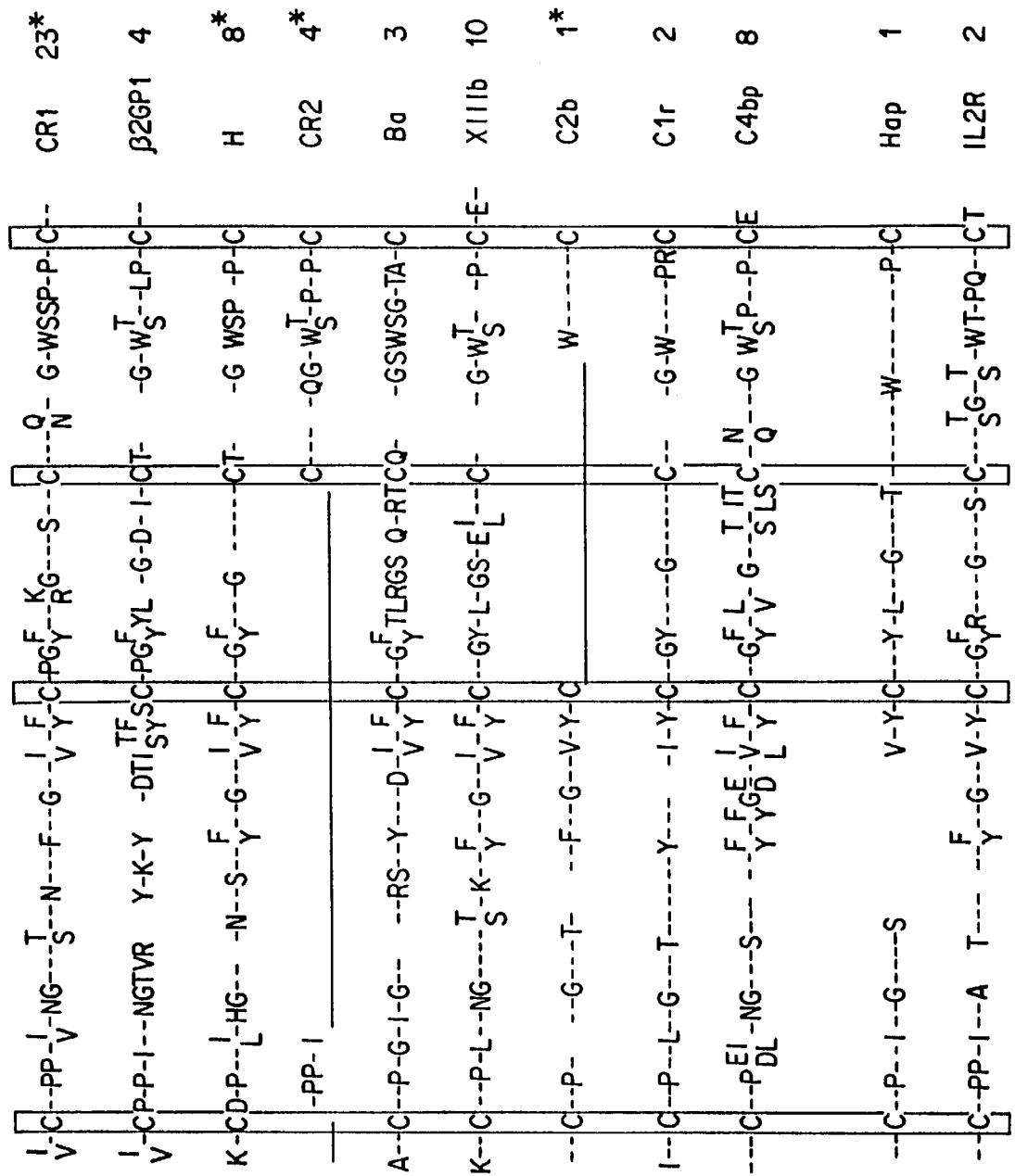

FIG. 7. Alignment of the consensus sequence of the SCRs of proteins known to have this structure. Spaces were introduced to maximize the alignment. A residue is deemed conserved as in FIG. 5, except for those proteins having only one or two SCRs, in which a residue is conserved if it is present in at least half of the other proteins. The dashes correspond to nonconserved positions. The underlined portions of CR2 and C2b indicate that no sequence information has been published in this region for these proteins. The boxes indicate the invariant half-cystines. The number to the right of the sequence represents the number of SCRs used to generate the consensus sequence. The protein abbreviations and references for the sequence data used to determine the consensus sequences are: (CR1) complement receptor type 1, (H) factor H (Kristensen, T., et al., 1986, J. Immunol. 136: 3407), (C4bp) C4 binding protein (Chung, L. P., et al., 1985, Biochem. J. 230: 133), (CR2) complement receptor type 2 (Weis, J. J., et al., 1986, Proc. Natl. Acad. Sci. U.S.A. 83: 5639), (Ba) proteolytic fragment of factor B (Morley, B. J. and Campbell, R. D., 1984, EMBO J. 3: 153), (C2b) proteolytic fragment of C2 (Gagnon, J., 1984, Philos. Trans. R. Soc. Lond. B Biol. Sci. 306: 301), (Clr) r subunit of C1 (Leytus, S. P., et al., 1986, Biochemistry 25: 4855), (XIIIb) b subunit of factor XIII (Ichinose, A., et al., 1986, Biochemistry 25: 4633), (β2GP1) β2 glycoprotein I (Lozier, J., et al., 1984, Proc. Natl., Acad. Sci. U.S.A. 81: 3640), (Hap) haptoglobin (Kurosky, A., et al., 1980, Proc. Natl. Acad. Sci. U.S.A. 77: 3388), (IL-2-R) the interleukin-2 receptor (Leonard, W. J., et al., 1985, Science 230: 633). Asterisk indicates that incomplete sequence is available.

Figure 8A:

FIG. 8(A through B). (A) Schematic diagram of the proposed structure of human CR1. The COOH-terminal cytoplasmic region is on the right side of the lipid bilayer. 30 SCRs are arrayed linearly on the extracellular side of the plasma membrane. The brackets indicate the LHRs. (B) The inset is an enlargement of a single SCR to illustrate the triple loop structure.

Figure 9:
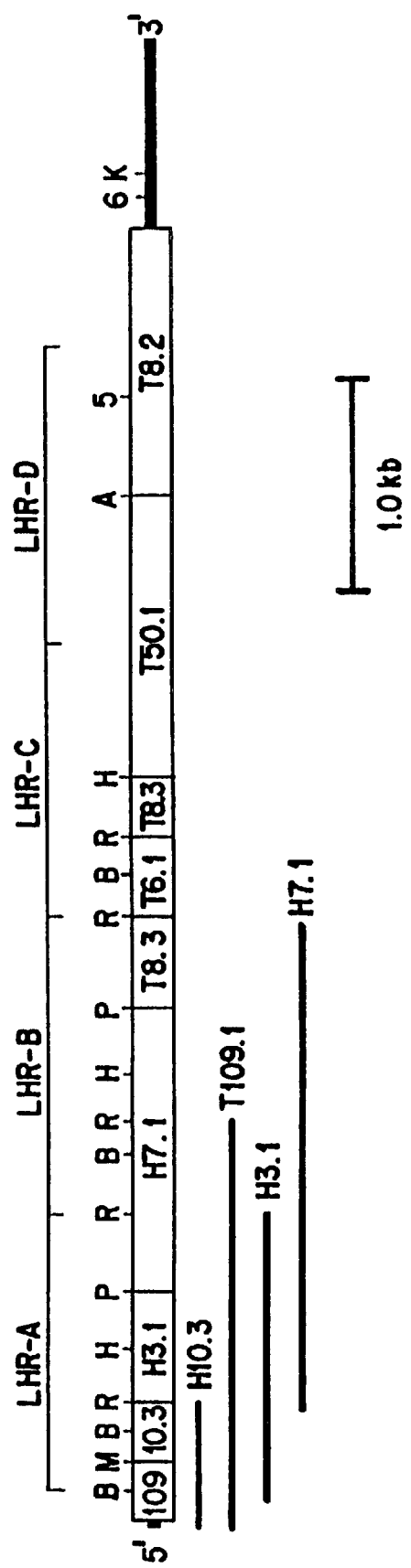

FIG. 9. Restriction map of the insert of the plasmid, pBSABCD, encoding human CR1. Indicated within the box delineating the region containing the coding sequence are the nine fragments of eight cDNA clones that were ligated to form the CR1 construct. The brackets designate the positions of LHR-A, -B, -C, and -D, respectively. The lines below the box represent the positions of the newly isolated 5' cDNA clones. The restriction sites are: A, ApaI; B, BamHI; G, BglII; H, HindIII; K, KpnI; M, BspMII; P, PstI; R, EcoRI; and S, SacI.

FIG. 10. The deduced amino acid sequence of the 5' cDNA clones encoding the seven SCRs of LHR-A, and alignment of this sequence with the corresponding SCRs of LHR-B, -C, and -D. The four cysteines that are conserved in each SCR are underlined. A residue is shown for LHR-B, -C and -D only where it is different from that in LHR-A.

FIG. 11(A through B). (A) Restriction maps of the expression plasmids, (B) piABCD and pMTABCD. $Pm_{MT}$ and $p_{CMV}$ represent the murine metallothionein and cytomegalovirus immediate early promoters, respectively.

FIG. 12(a through d). Analysis by phase contrast (panels a and c) and immunofluorescent (panels b and d) microscopy of COS cells transfected with piABCD (panels a and b) and CDM8 vector alone (panels c and d), respectively, and indirectly stained with YZ1 monoclonal anti-CR1 antibody and fluorescein-labelled goat anti-mouse F(ab')$_2$.

FIG. 13(a through d). Analysis of C3b- and C4b-binding by COS cells expressing recombinant CR1. COS cells transfected with piABCD (panels a and c) or with the CDM8 vector alone (panels b and d) were incubated with EAC4b (lim),3b (panels a and b) or with EAC4b (panels c and d) and examined for formation of rosettes by phase contrast microscopy.

Figure 14:
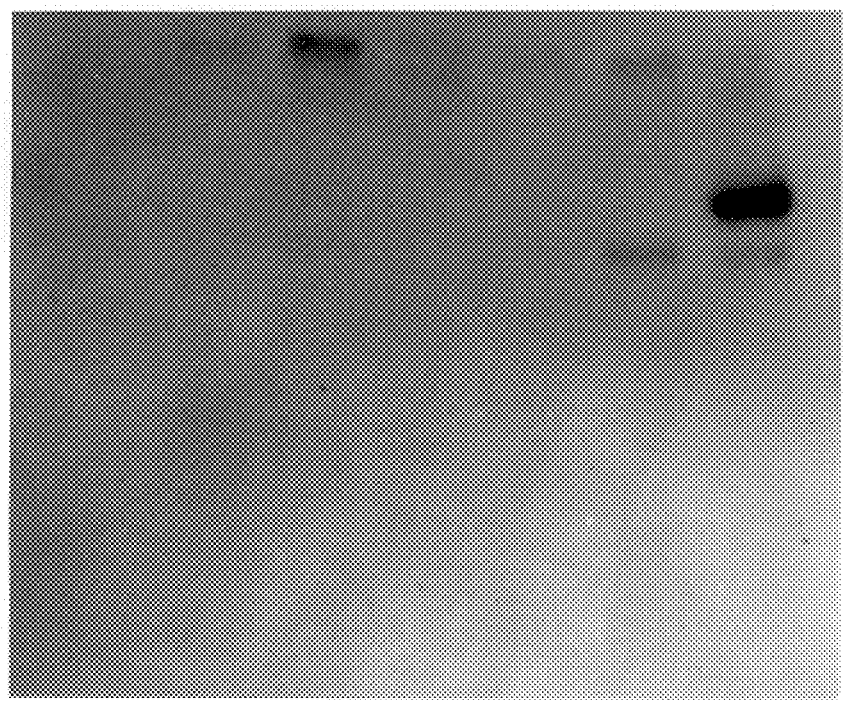

FIG. 14. Analysis of recombinant CR1 expressed by transfected COS cells by SDS-PAGE. COS cells transfected with the CDM8 vector alone (lanes 1 and 4) and with piABCD (lanes 2 and 5), respectively, and erythrocytes from an individual having the F and S allotypes of CR1 (lanes 3 and 6) were surface labelled with $^{125}$I. Detergent lysates of the cells were sequentially immunoadsorbed with Sepharose-UPC10 (lanes 1–3) and Sepharose-YZ1 (lanes 4–6) and the eluates analyzed by SDS-PAGE under non-reducing conditions and autoradiography.

Figure 15:
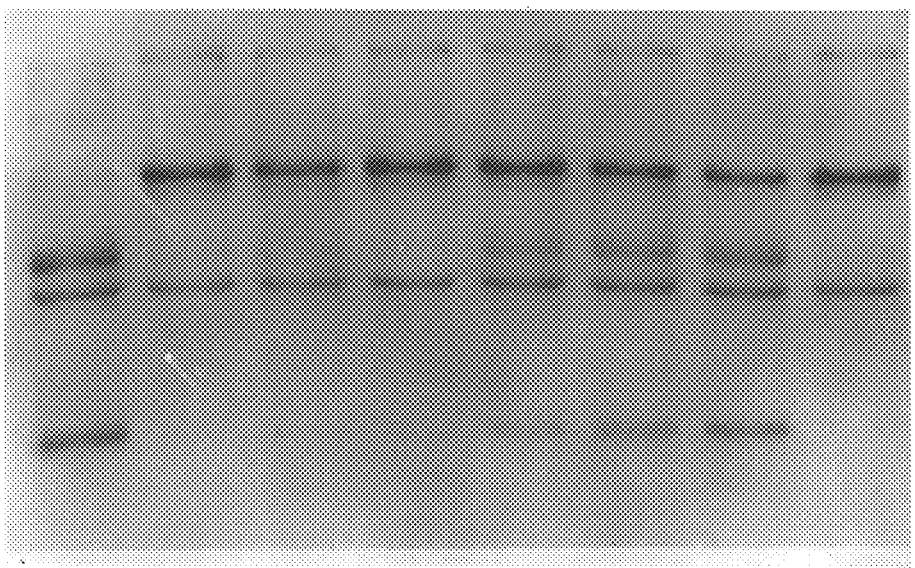

FIG. 15. Cleavage of $^{125}$I-C3 (ma) by factor I in the presence of immunoimmobilized recombinant CR1. Replicate samples of $^{125}$I-C3 (ma) were treated with factor I in the presence of factor H (lane 1), Sepharose-UPC10 preincubated with the lysate of COS cells transfected with the CDM8 vector alone (lane 2), Sepharose-UPC10 preincubated with the lysate of piABCD-transfected COS cells (lane 3), Sepharose-YZ1 preincubated with the lysate of CDM8-transfected COS cells (lane 4), and 6 μl (lane 5), 12 μl (lane 6) and 25 μl (lane 7) of Sepharose-YZ1 that had been preincubated with the lysate of piABCD-transfected COS cells. Samples of $^{125}$I-labelled C3 (ma) were also treated in the absence of factor I with 25 μl of Sepharose-YZ1 that had been preincubated with the lysate of piABCD-transfected COS cells (lane 8). After reduction, the $^{125}$I-C3 (ma) was analyzed by SDS-PAGE and autoradiography.

Figure 16:
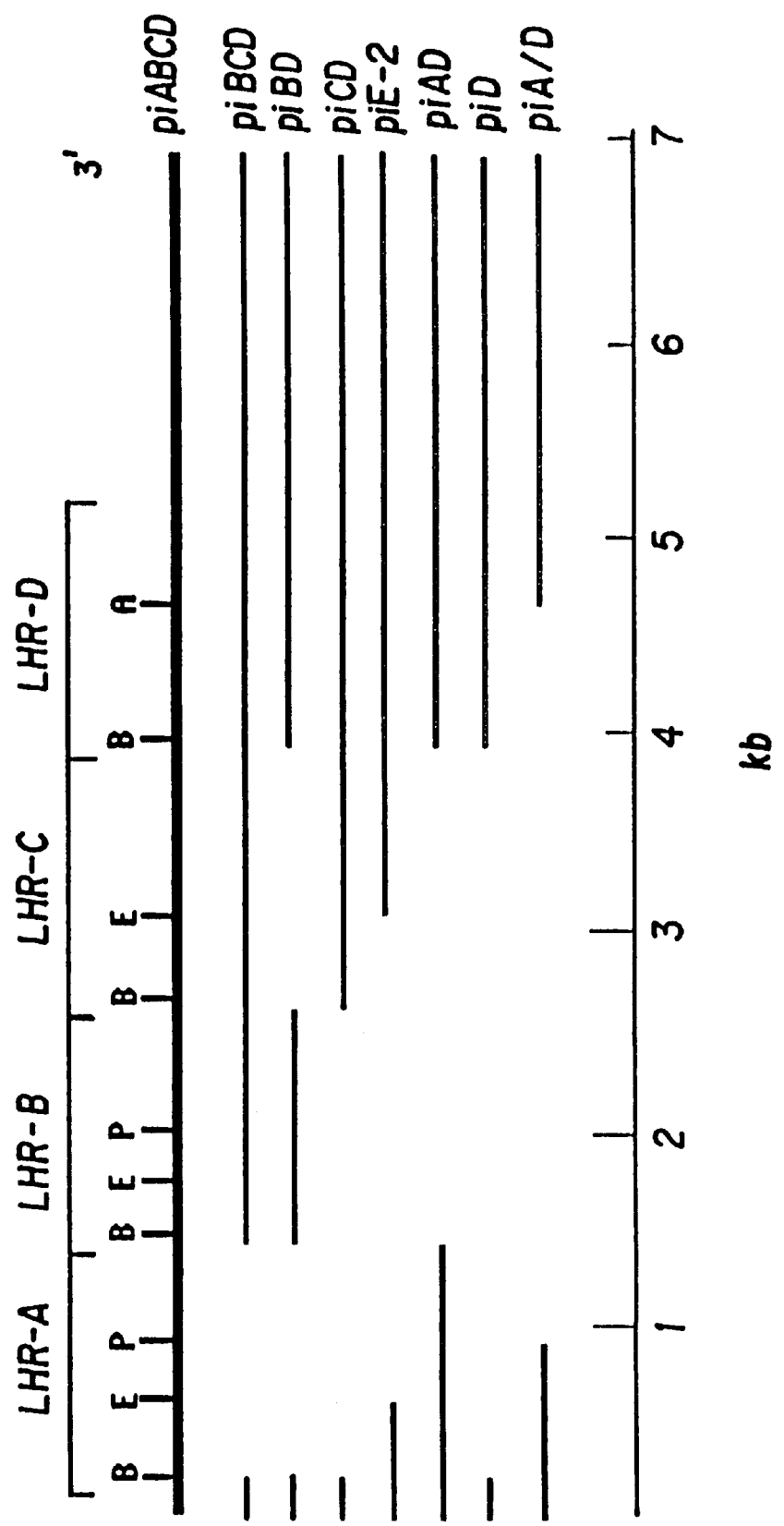

FIG. 16. The cDNA constructs encoding the CR1 deletion mutants. The positions of the cDNA segments encoding the four LHRs are indicated by the brackets above the full length piABCD construct on which are shown the restriction sites used for preparation of the deletion mutants. The cDNA restriction fragments remaining in each of the mutants are indicated by the solid lines. The restriction sites are: A, ApaI; B, BsmI; E, BstEII; and P, PstI.

Figure 17:
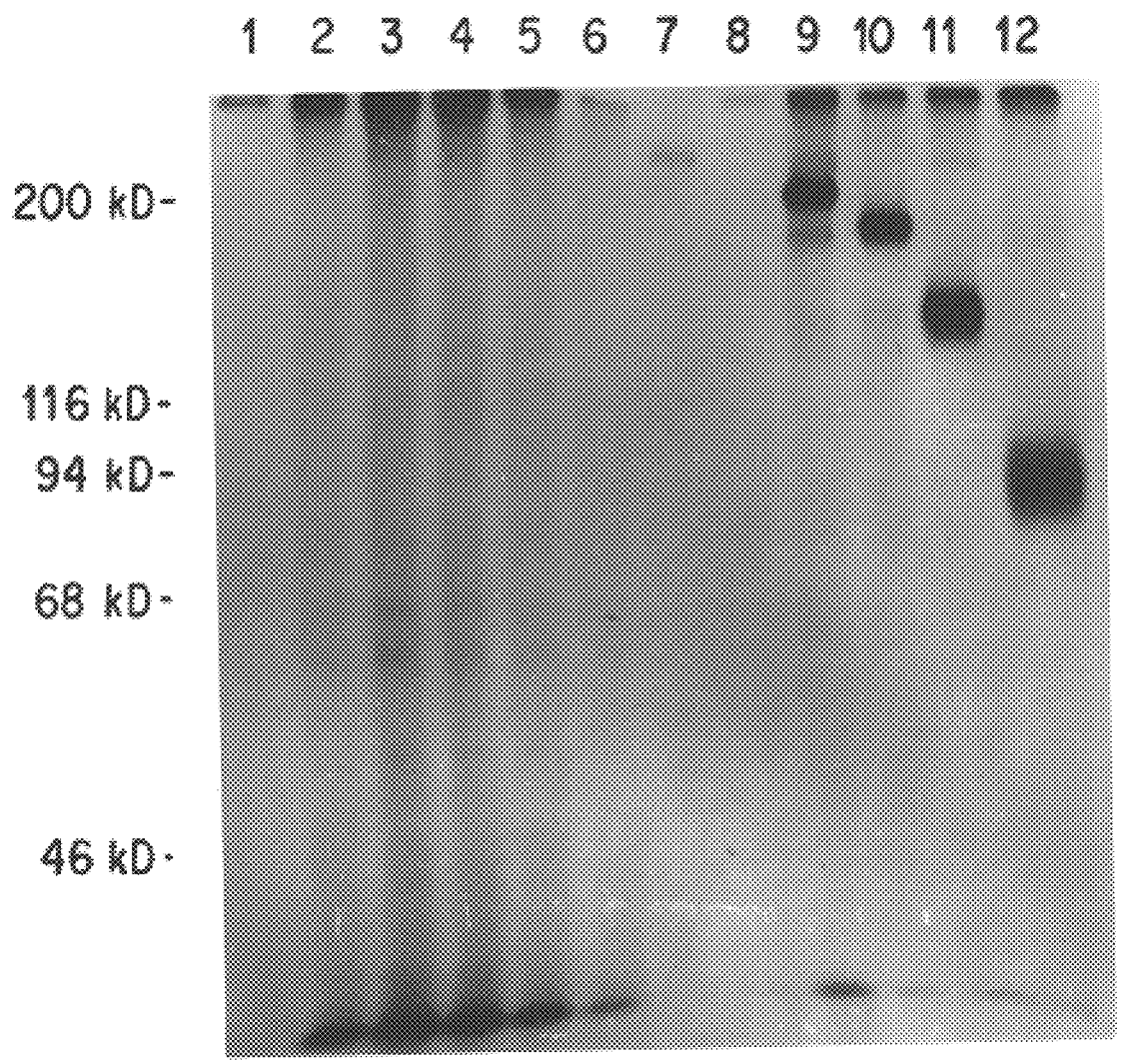

FIG. 17. Comparison of recombinant deletion mutants of CR1 with the wild type F and S allotypes of CR1. Detergent lysates of $^{125}$I-surface labelled erythrocytes (lanes 1 and 7) alone S cells transfected with CDM8 vector alone (lanes 2 and 8), piABCD (lanes 3 and 9), piBCD (lanes 4 and 10), piCD (lanes 5 and 11) and piD (lanes 6 and 12), respectively, were immunoprecipitated with Sepharose-UPC10 anti-levan antibody (lanes 1–6), Sepharose-YZ-1 anti-CR1 monoclonal antibody (lanes 7–11) and rabbit anti-CR1 antibody and Sepharose-protein A (lane 12), respectively. The eluates were subjected to SDS-PAGE under reducing conditions and autoradiography.

Figure 18:
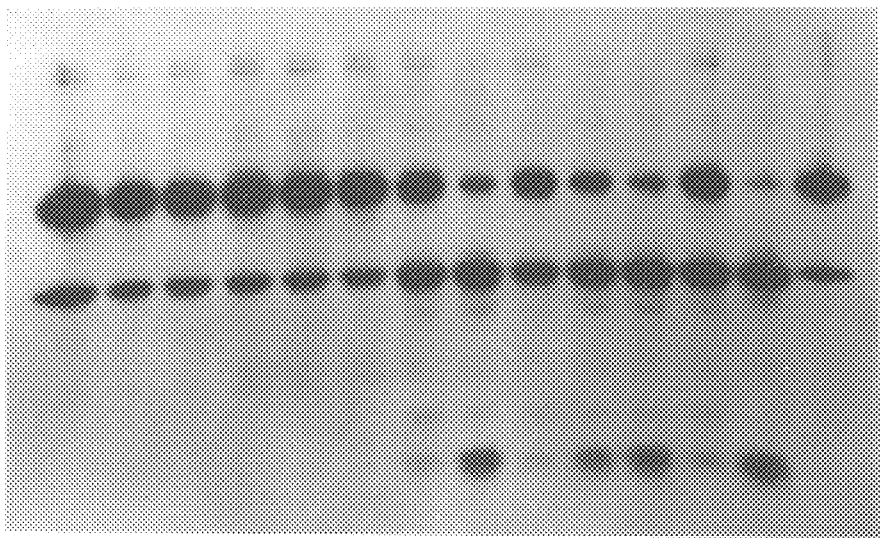

FIG. 18. Cleavage of $^{125}$I-C3 (ma) by factor I in the presence of COS cells expressing full length and deletion mutants of CR1. Replicate samples of $^{125}$I-C3 (ma) were incubated with COS cells transfected with the CDM8 vector alone (lanes 1 and 7), piABCD (lanes 2 and 8), piAD (lanes 3 and 9), piBD (lanes 4 and 10), piCD (lanes 5 and 11), and piD (lanes 6 and 12), respectively, in the absence (lanes 1–6) or presence (lanes 7–12) of factor I. Samples of $^{125}$I-C3(ma) also were incubated with factor H and factor I (lane 13) and with factor I alone (lane 14), respectively. After reduction, the $^{125}$I-C3(ma) was analyzed by SDS-PAGE and autoradiography.

Figure 19:
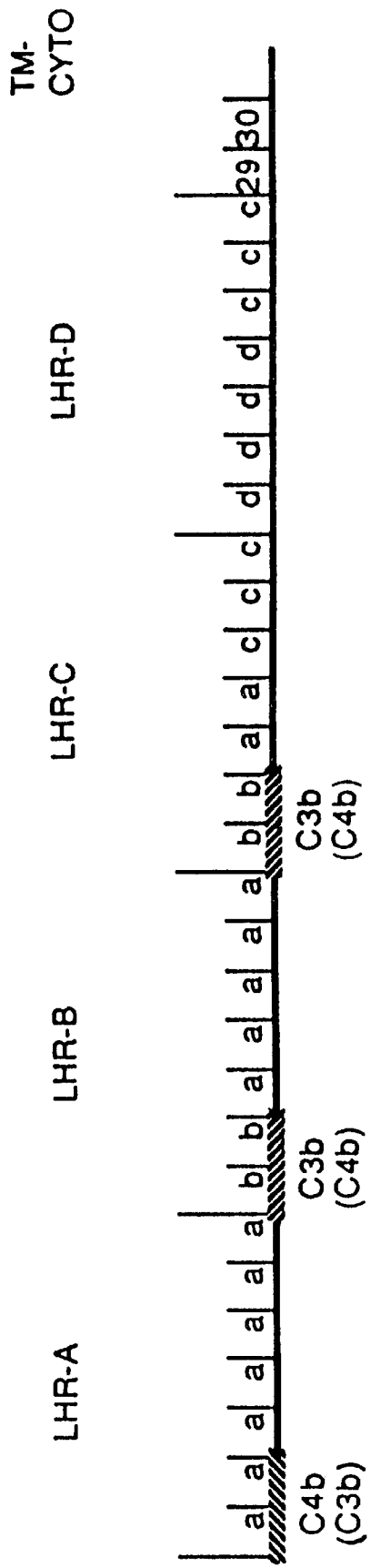

FIG. 19. Schematic model depicting the types of SCRs comprising each LHR of CR1, and the predicted sites determining the specificities of the receptor for C3b and C4b. The secondary binding specificities of these are indicated by the parentheses.

Figure 20:
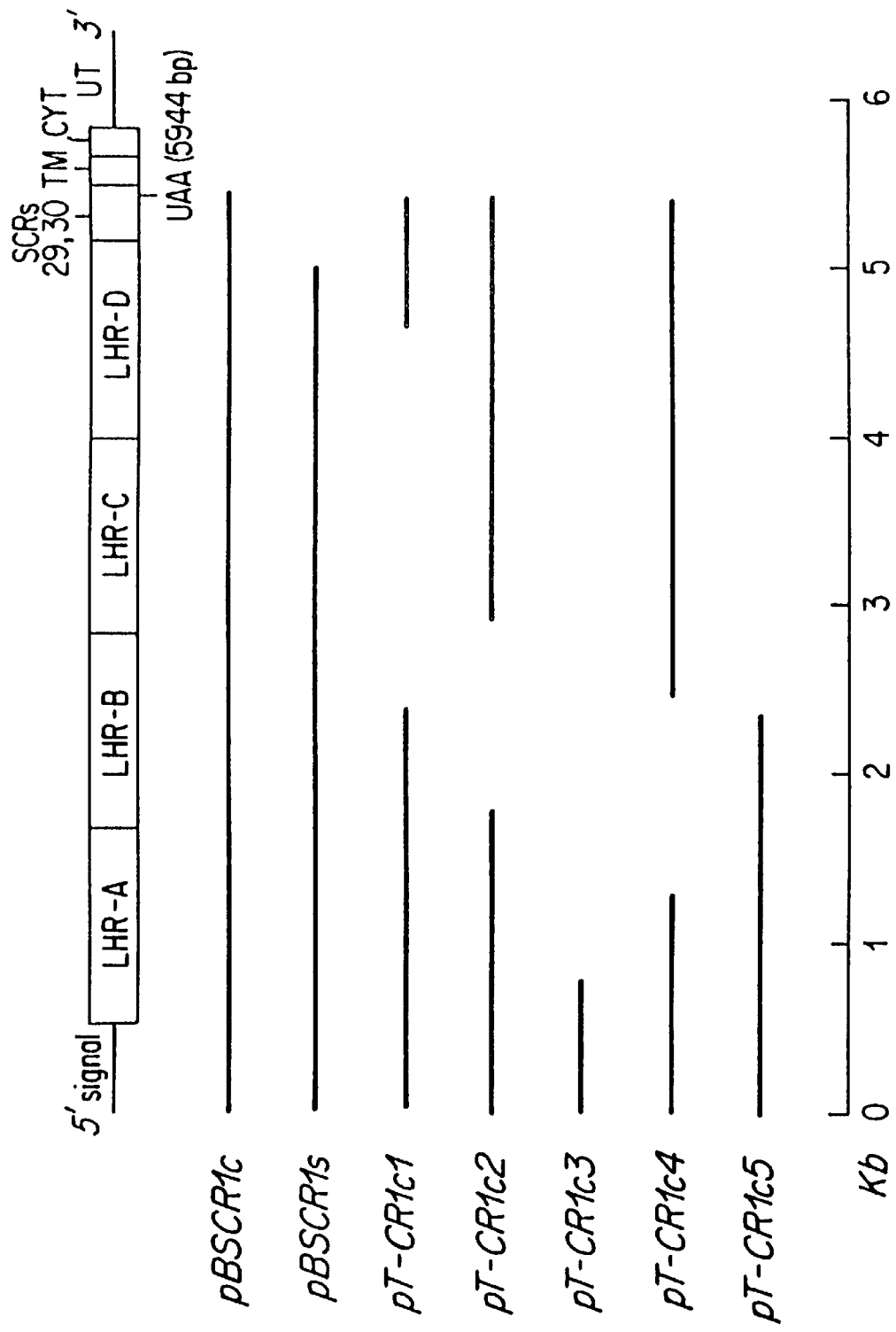

FIG. 20. A schematic diagram illustrating the DNA regions remaining in the soluble CR1 DNA constructs. The regions of the full length CR1 cDNA are indicated by the boxes along the top of the figure.

Figure 21:
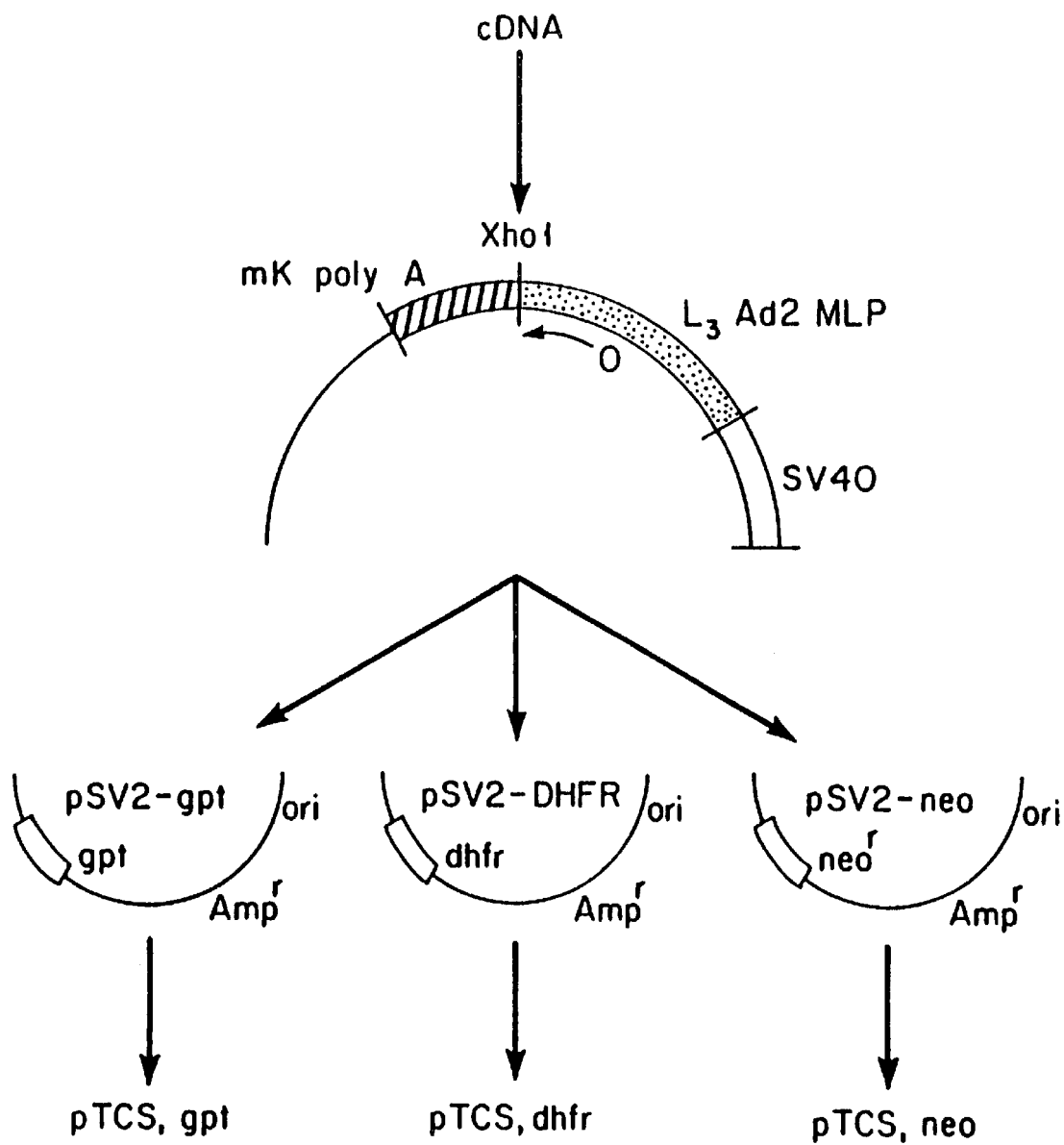

FIG. 21. A schematic diagram illustrating the major elements in the pTCS series of expression vectors.

Figure 22:
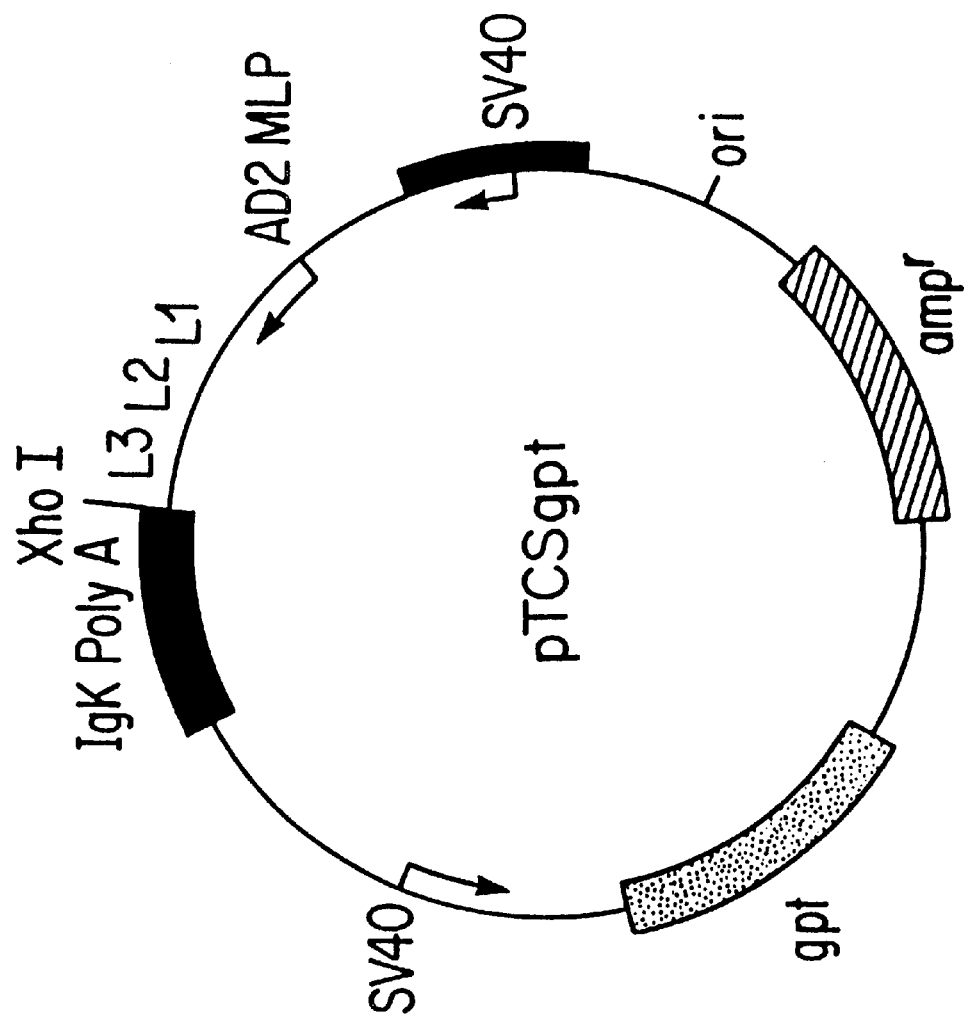

FIG. 22. A diagram of the expression vector pTCSgpt. The polyadenylation site is from the murine Ig kappa sequences (NBRF Nucleic database accession #Kcms, bp 1306–1714); the Ad2 MLP and tripartite regions are from the Ad2 sequence (NBRF Nucleic database accession #Gdad2, bp 5791–6069); the SV40 early promoter is from the SV40 genome (NBRF Nucleic Database accession #GSV40W). The gpt gene, ampicillin gene and bacterial origin of replication are from the vector pSV2gpt (ATCC Accession No. 37145).

Figure 23:
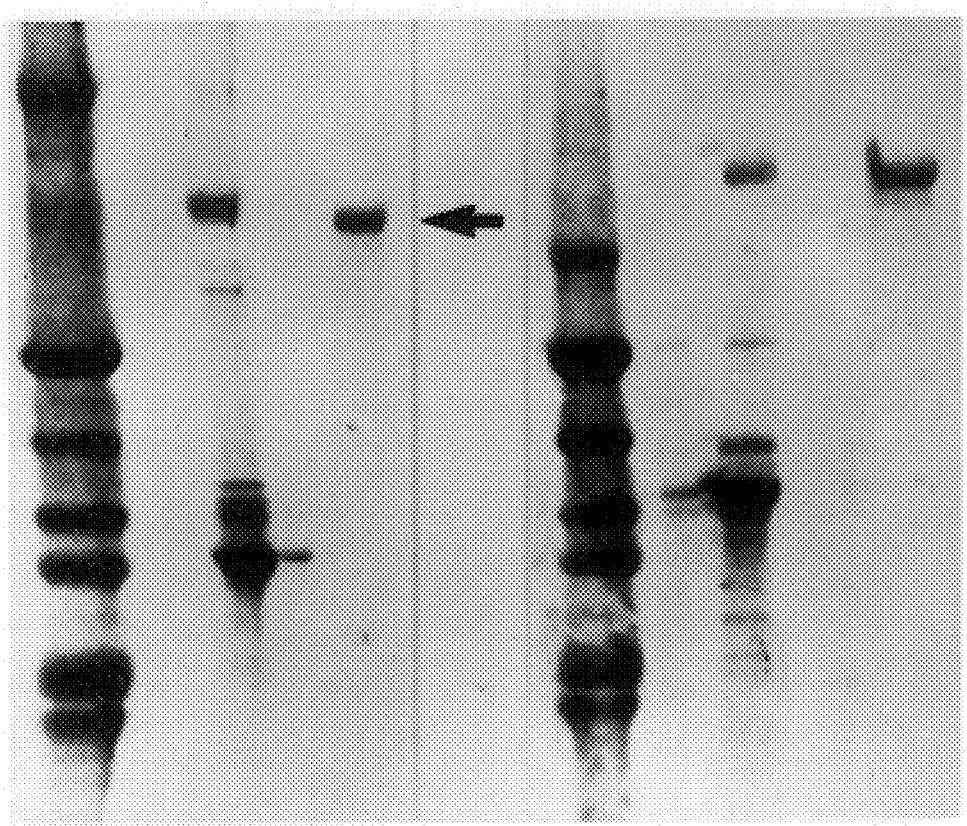

FIG. 23. 4–20% SDS-PAGE of antibody affinity purified sCR1. Non-reducing (lanes 1, 2, 3) and reducing (lanes 4, 5, 6) conditions. Lanes 1, 3: molecular weight markers; lanes 3, 5: cell culture supernatant starting material; lanes 4, 6: sCR1 purified by antibody affinity chromatography.

Figure 24:
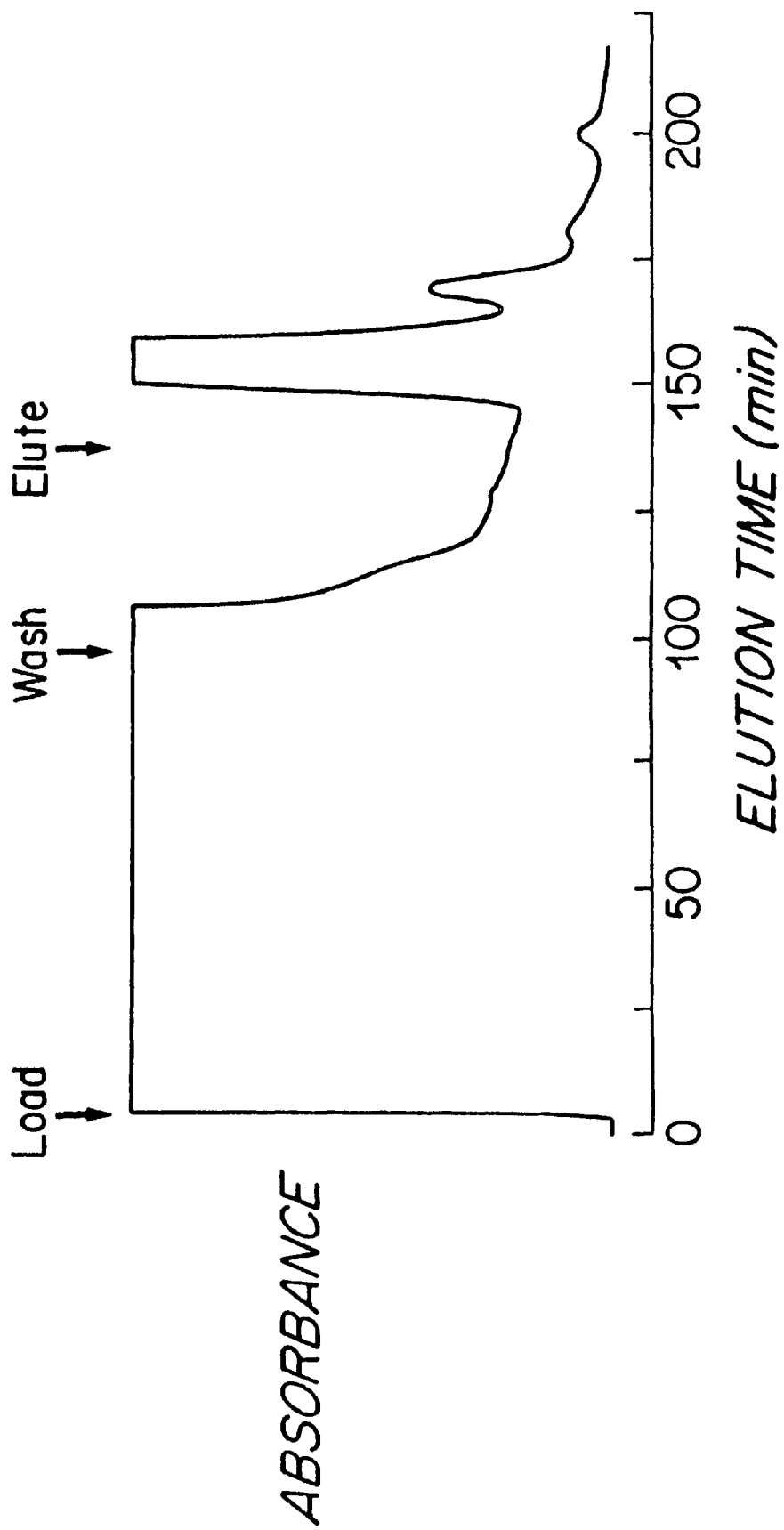

FIG. 24. Cation exchange HPLC elution profile. Eluted protein was monitored by absorbance at 280 nm (y-axis). The absorbance of both the flow-through (0–100 minutes) and the eluted sCR1 (150–165 minutes) were both offscale. The x-axis represents the elution time in minutes.

Figure 25:
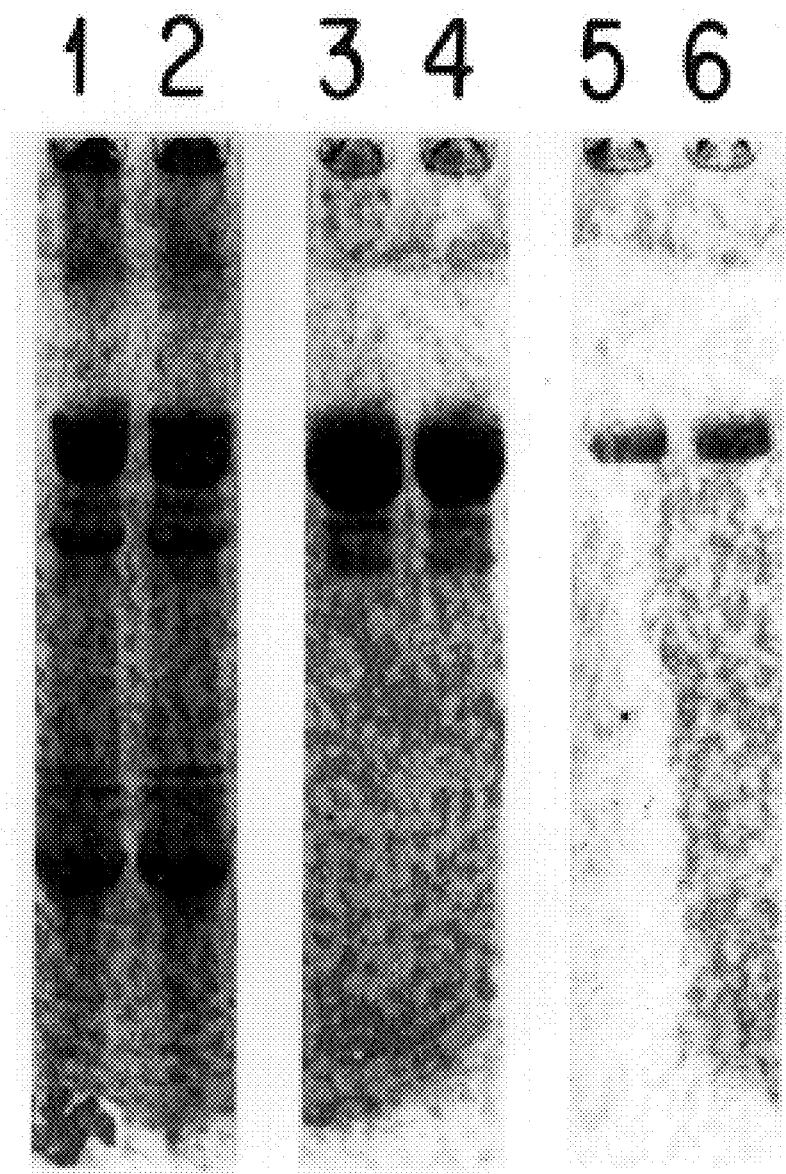
Figure 26A:
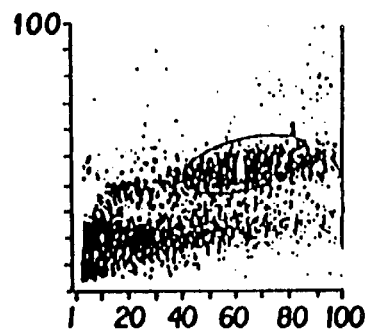
Figure 26B:
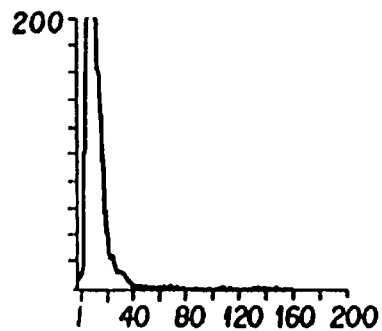
Figure 26C:
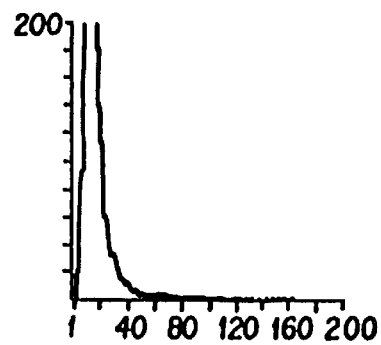
Figure 26D:
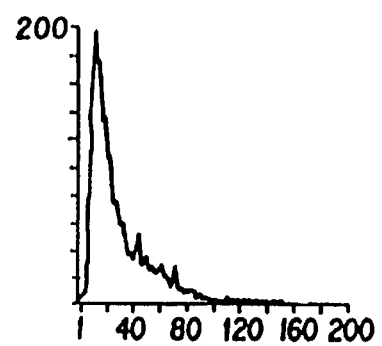
Figure 26E:
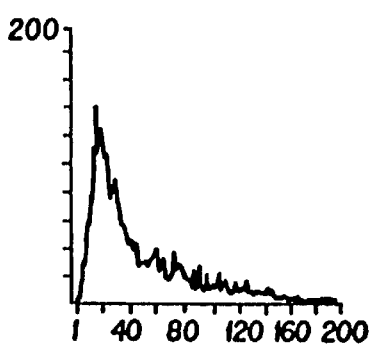
Figure 26F:
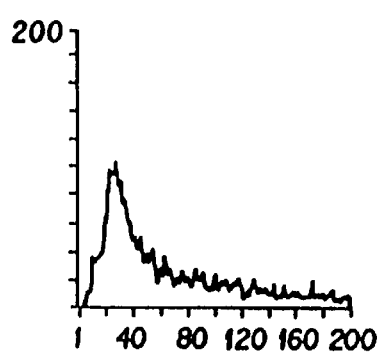
Figure 26G:
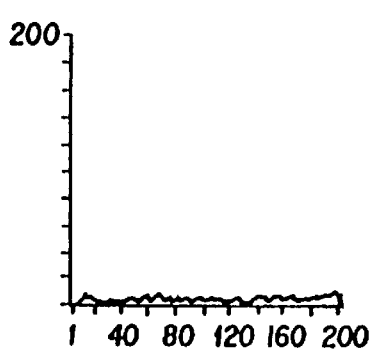

FIG. 25. 4–20% gradient SDS-PAGE of cation and anion exchange HPLC purified sCR1. SDS-polyacryamide gels were run under non-reducing conditions. Lane 1, an aliquot of bioreactor supernatant; lane 2, an aliquot of bioreactor supernatant dialyzed against cation HPLC starting buffer; lane 3, an aliquot of the eluted sCR1 peak from a cation exchange HPLC column; lane 4, an aliquot of the sCR1 peak from the cation exchange HPLC column dialyzed into starting buffer for anion HPLC; lanes 5 and 6, aliquots of two different fractions of eluted sCR1 from anion HPLC.

FIG. 26(a through g). C5a induction of an oxygen burst in human neutrophils. Following a C5a induced oxygen burst, DCFDA became oxidized and brightly fluoresced. Fluorescent intensity, as determined by flow cytometry, is measured on the x-axis and number of cells on the y-axis. Panel a, profile and gate for the cells; panel b, 0 minutes after C5a addition; panel c, 1 minute; panel d, 2 minutes; panel e, 3 minutes; panel f, 4 minutes; panel g, 20 minutes. This DCFDA assay gives a sensitive indication of C5a.

FIG. 27(a through c). Activation of human complement in the presence of sCR1 shows reduced C5a activity in the DCFDA assay. Panel a, unstimulated cells; panel b, control without sCR1 showing a high degree of fluorescence; panel c, DCFDA assay in the presence of sCR1 showing a reduction of 75% in fluorescent intensity. y-axis is number of cells and x-axis is fluorescent intensity.

Figure 28:
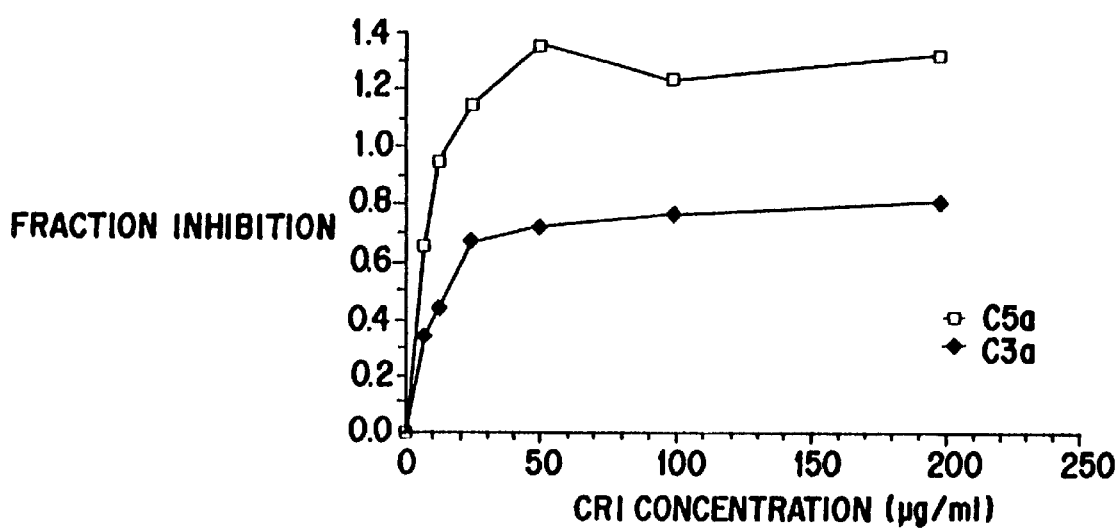

FIG. 28. Inhibition of classical pathway C5a and C3a production in human serum by sCR1. Similar profiles were observed for either antibody affinity purified or HPLC purified sCR1.

Figure 29:
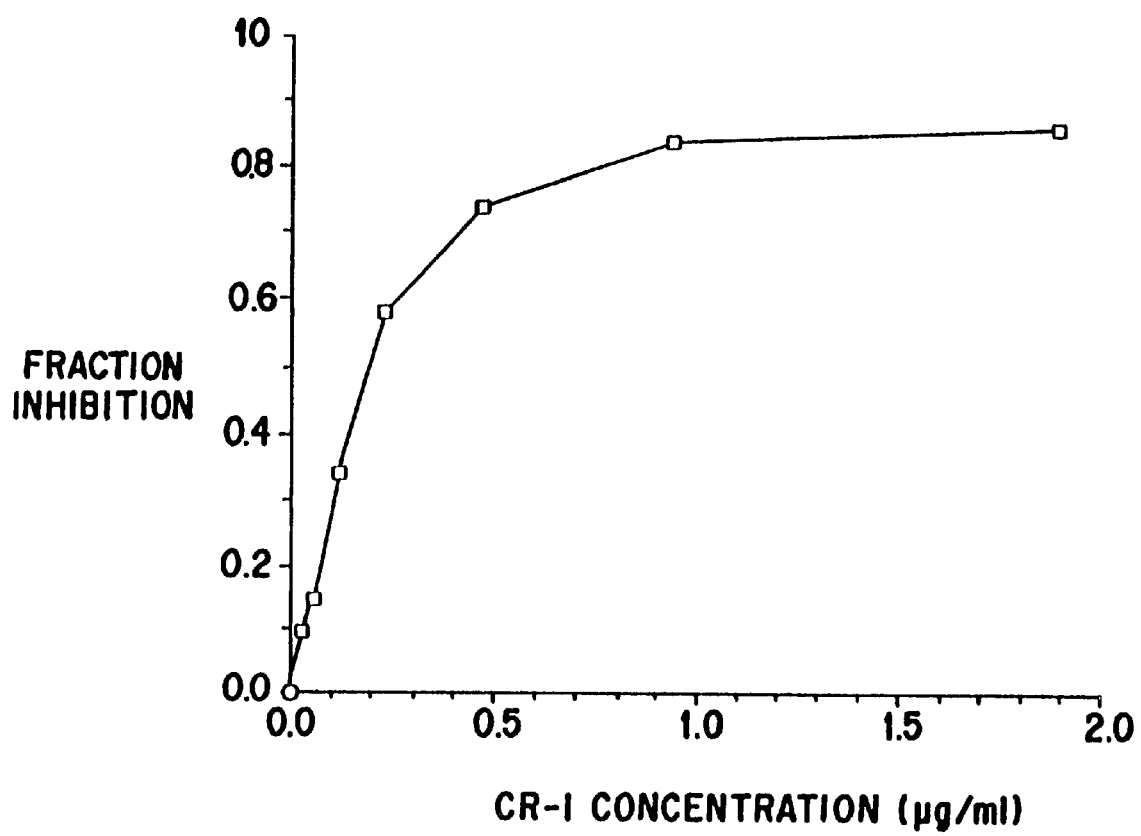

FIG. 29. Inhibition of complement-mediated hemolysis by recombinant sCR1. Similar profiles were observed for antibody affinity purified or HPLC purified sCR1.

FIG. 30(A through B). Gross morphology of RPAR in sCR1-treated (left) and untreated (right) rats. (A) Both rats received an intravenous injection of ovalbumin, followed by an intradermal injection of a mixture of either sCR1 (left rat) or PBS (right rat) with anti-ovalbumin, neat (left site); anti-ovalbumin, ½ dilution (middle site) or rabbit IgG (right site). The injections were performed in duplicate; top and bottom rows gave identical results. The rat which received sCR1 had barely visible changes, while the untreated rat developed full symptoms of RPAR. (B) The dermal surface of the skin biopsies from (A). The biopsy from the untreated rat (right) developed clearly visible lesion, while the biopsy from the sCR1 -treated rat (left) showed normal morphology.

FIG. 31(A through B). Light microscopy of skin biopsies from sCR1 -treated (A) and untreated (B) rats. (A) Perivascular accumulation of polymorphonuclear and mononuclear cells was observed, however, no extensive infiltration of neutrophils or extravasation of erythrocytes was seen. (B) Extensive infiltration of polymorphonuclear cells and extravasation of erythrocytes was identified.

5. DETAILED DESCRIPTION OF THE INVENTION

The present invention is directed to the C3b/C4b receptor (CR1) gene and its encoded protein. The invention is also directed to CR1 nucleic acid sequences and fragments thereof comprising 70 nucleotides and their encoded peptides or proteins comprising 24 amino acids. The invention further provides for the expression of the CR1 protein and fragments thereof. Such CR1 sequences and proteins have value in diagnosis and therapy of inflammatory or immune system disorders, and disorders involving complement activity.

In a specific embodiment, the invention relates to soluble CR1 molecules and the expression, purification, and uses thereof. As used herein, the term "soluble CR1 molecules" shall mean portions of the CR1 protein which, in contrast to the native CR1 proteins, are not expressed on the cell surface as membrane proteins. As a particular example, CR1 molecules which substantially lack a transmembrane region are soluble CR1 molecules. In a preferred embodiment, the soluble CR1 molecules are secreted by a cell in which they are expressed.

In specific embodiments of the present invention detailed in the examples sections infra, the cloning and complete nucleotide and deduced amino acid sequence of the fulllength CR1 cDNA, and of fragments thereof, and the expression of the encoded CR1 products, are described. The expression of CR1 and fragments thereof, with binding sites for C3b and/or C4b, and which inhibit factor I cofactor activity, is also described. The invention is further illustrated by the production and purification of soluble, truncated CR1 molecules. In specific examples, such molecules are demonstrated to be therapeutically useful in reducing inflammation, and in reducing myocardial infarct size and preventing reperfusion injury.

5.1. Isolation of the CR1 Gene

The complete coding sequence of the CR1 gene and its deduced amino acid sequence is presented in FIG. 1.

Any human cell can potentially serve as the nucleic acid source for the molecular cloning of the CR1 gene. Isolation of the CR1 gene involves the isolation of those DNA sequences which encode a protein displaying CR1-associated structure or properties, e.g., binding of C3b or C4b or immune complexes, modulating phagocytosis, immune stimulation or proliferation, and regulation of complement. The DNA may be obtained by standard procedures known in the art from cloned DNA (e.g., a DNA "library"), by chemical synthesis, by cDNA cloning, or by the cloning of genomic DNA, or fragments thereof, purified from the desired human cell. (See, for example, Maniatis et al., 1982, Molecular Cloning, A Laboratory Manual, Cold Spring Harbor Laboratory, Cold Spring Harbor, N.Y.; Glover, D. M. (ed.), 1985, DNA Cloning: A Practical Approach, MRL Press, Ltd., Oxford, U.K., Vol. I, II.) Cells which can serve as sources of nucleic acid for cDNA cloning of the CR1 gene include but are not limited to monocytes/macrophages, granulocytes, B cells, T cells, splenic follicular dendritic cells, and glomerular podocytes. Clones derived from genomic DNA may contain regulatory and intron DNA regions in addition to coding regions; clones derived from cDNA will contain only exon sequences. Whatever the source, the CR1 gene should be molecularly cloned into a suitable vector for propagation of the gene.

In the molecular cloning of the gene from genomic DNA, DNA fragments are generated, some of which will encode the desired CR1 gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the CR1 gene may be accomplished in a number of ways. For example, if an amount of a CR1 gene or its specific RNA, or a fragment thereof, is available and can be purified and labeled, the generated DNA fragments may be screened by nucleic acid hybridization to the labeled probe (Benton, W. and Davis, R., 1977, Science 196: 180; Grunstein, M. and Hogness, D., 1975, Proc. Natl. Acad. Sci. U.S.A. 72: 3961). Those DNA fragments with substantial homology to the probe will hybridize. If a purified CR1-specific probe is unavailable, nucleic acid fractions enriched in CR1 may be used as a probe, as an initial selection procedure. As an example, the probe representing B cell cDNA from which messages expressed by fibroblasts have been subtracted can be used. It is also possible to identify the appropriate fragment by restriction enzyme digestion(s) and comparison of fragment sizes with those expected according to a known restriction map if such is available. Further selection on the basis of the properties of the gene, or the physical, chemical, or immunological properties of its expressed product, as described infra, can be employed after the initial selection.

The CR1 gene can also be identified by mRNA selection by nucleic acid hybridization followed by in vitro translation. In this procedure, fragments are used to isolate complementary mRNAs by hybridization. Such DNA fragments may represent available, purified CR1 DNA, or DNA that has been enriched for CR1 sequences. Immunoprecipitation analysis or functional assays (e.g., for C3b or C4b binding, or promotion of phagocytosis or immune stimulation, or complement regulation, etc.) of the in vitro translation products of the isolated mRNAs identifies the mRNA and, therefore, the complementary DNA fragments that contain the CR1 sequences. In addition, specific mRNAs may be selected by adsorption of polysomes isolated from cells to immobilized antibodies specifically directed against CR1. A radiolabeled CR1 cDNA can be synthesized using the selected mRNA (from the adsorbed polysomes) as a template. The radiolabeled mRNA or cDNA may then be used as a probe to identify the CR1 DNA fragments from among other genomic DNA fragments.

Alternatives to isolating the CR1 genomic DNA include, but are not limited to, chemically synthesizing the gene sequence itself from a known sequence or making cDNA to the mRNA which encodes the CR1 gene. For example, as described supra, RNA for cDNA cloning of the CR1 gene can be isolated from cells including but not limited to monocytes/macrophages, granulocytes, B cells, T cells, dendritic cells, and podocytes. In a preferred embodiment, tonsilar cells can serve as the source of mRNA for cDNA cloning (See Section 6.1.2, infra). Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid or CDM8 plasmid (Seed, B., 1987, Nature 329: 840–842) or derivatives. Recombinant molecules can be introduced into host cells via transformation, transfection, infection, electroporation, etc.

In an alternative method, the CR1 gene may be identified and isolated after insertion into a suitable cloning vector, in a "shot gun" approach. Enrichment for the CR1 gene, for example, by size fractionation, can be done before insertion into the cloning vector.

The CR1 gene is inserted into a cloning vector which can be used to transform, transfect, or infect appropriate host cells so that many copies of the gene sequences are generated. In a specific embodiment, the cloning vector can be the CDM8 vector, which can be used to achieve expression in a mammalian host cell. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and CR1 gene may be modified by homopolymeric tailing.

Identification of the cloned CR1 gene can be accomplished in a number of ways based on the properties of the DNA itself, or alternatively, on the physical, immunological, or functional properties of its encoded protein. For example, the DNA itself may be detected by plaque or colony nucleic acid hybridization to labeled probes (Benton, W. and Davis, R., 1977, Science 196: 180; Grunstein, M. and Hogness, D., 1975, Proc. Natl. Acad. Sci. U.S.A. 72: 3961). Alternatively, the presence of the CR1 gene may be detected by assays based on properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, C3b and/or C4b and/or immune complex binding activity, complement regulatory activity, effects on phagocytosis or immune stimulation, or antigenic properties as known for CR1. Using an antibody to CR1, the CR1 protein may be identified by binding of labeled antibody to the putatively CR1-synthesizing clones, in an ELISA (enzyme-linked immunosorbent assay)-type procedure.

In specific embodiments, transformation of host cells with recombinant DNA molecules that incorporate the isolated CR1 gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

In a particular embodiment, CR1 cDNA clones in a CDM8 vector can be transfected into COS (monkey kidney) cells for large-scale expression under the control of the cytomegalovirus promoter (see Section 8, infra).

If the ultimate goal is to insert the gene into virus expression vectors such as vaccinia virus or adenovirus, the recombinant DNA molecule that incorporates the CR1 gene can be modified so that the gene is flanked by virus sequences that allow for genetic recombination in cells infected with the virus so that the gene can be inserted into the viral genome.

After the CR1 DNA-containing clone has been identified, grown, and harvested, its DNA insert may be characterized as described in Section 5.4.1, infra.

When the genetic structure of the CR1 gene is known, it is possible to manipulate the structure for optimal use in the present invention. For example, promoter DNA may be ligated 5' of the CR1 -coding sequence, in addition to or replacement of the native promoter to provide for increased expression of the protein. Expression vectors which express CR1 deletion mutants can also be made, to provide for expression of defined fragments of the CR1 sequence (see the example sections, infra). In a particular embodiment, deletion mutants can be constructed which encode fragments of the CR1 protein that exhibit the desired C3b and/or C4b binding activity (see Section 9, infra), e.g., LHR-A for binding of C4b, or LHR-C for binding of C3b. In a preferred embodiment, an expression vector which encodes a CR1 molecule with a deletion of the transmembrane region can be used to produce a soluble CR1 molecule (see the examples sections 11–14, infra). Many manipulations are possible, and within the scope of the present invention.

5.2. Expression of the Cloned CR1 Gene

The nucleotide sequence coding for the CR1 protein (FIG. 1) or a portion thereof, can be inserted into an appropriate expression vector, i.e., a vector which contains the necessary elements for the transcription and translation of the inserted protein-coding sequence. The necessary transcriptional and translation signals can also be supplied by the native CR1 gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. The expression elements of these vectors vary in their strength and specificities. Depending on the host-vector system utilized, any one of a number of suitable transcription and translation elements may be used. For instance, when cloning in mammalian cell systems, promoters isolated from the genome of mammalian cells or from viruses that grow in these cells (e.g., adenovirus, simian virus 40, cytomegalovirus) may be used. Promoters produced by recombinant DNA or synthetic techniques may also be used to provide for transcription of the inserted sequences.

Specific initiation signals are also required for efficient translation of inserted protein coding sequences. These signals include the ATG initiation codon and adjacent sequences. In cases where the entire CR1 gene including its own initiation codon and adjacent sequences are inserted into the appropriate expression vectors, no additional translational control signals may be needed. However, in cases where only a portion of the CR1 coding sequence is inserted, exogenous translational control signals, including the ATG initiation codon, must be provided. The initiation codon must furthermore be in phase with the reading frame of the protein coding sequences to ensure translation of the entire insert. These exogenous translational control signals and initiation codons can be of a variety of origins, both natural and synthetic.

Any of the methods previously described for the insertion of DNA fragments into a vector may be used to construct expression vectors containing a chimeric gene. consisting of appropriate transcriptional/translational control signals and the protein coding sequences. These methods may include in vitro recombinant DNA and synthetic techniques and in vivo recombinations (genetic recombination).

In a specific embodiment, a soluble CR1 molecule can be expressed. Such a soluble molecule can be produced by use of recombinant DNA techniques to delete the DNA sequences encoding the CR1 transmembrane region (see Sections 11–14, infra). As demonstrated infra, the ability to express a soluble CR1 molecule is not limited to any one genetic modification of the CR1 nucleic acid sequence; as long as the nucleic acid sequence encoding a substantial portion of the CR1 transmembrane region is deleted, soluble CR1 constructs can be obtained.

Expression vectors containing CR1 gene inserts can be identified by three general approaches: (a) DNA—DNA hybridization, (b) presence or absence of "marker" gene functions, and (c) expression of inserted sequences. In the first approach, the presence of a foreign gene inserted in an expression vector can be detected by DNA—DNA hybridization using probes comprising sequences that are homologous to the inserted CR1 gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes into the vector. For example, if the CR1 gene is inserted within the marker gene sequence of the vector, recombinants containing the CR1 insert can be identified by the absence of the marker gene function. In the third approach, recombinant expression vectors can be identified by assaying the foreign gene product expressed by the recombinant. Such assays can be based on the physical, immunological, or functional properties of the gene product.

Once a particular recombinant DNA molecule is identified and isolated, several methods known in the art may be used to propagate it. Once a suitable host system and growth conditions are established, recombinant expression vectors can be propagated and prepared in quantity.

In a particular embodiment detailed in the examples of the present invention, CDM8 vectors with an CR1 cDNA insert can be transfected into COS cells, in which the CR1 cDNA insert is expressed to produce the CR1 protein. In other particular embodiments detailed in the examples sections infra, CDM8 vectors with a CR1 cDNA insert corresponding to a portion of the CR1 coding region can be transfected into COS cells, where the CR1 or fragment is expressed. Per yet another example, infra, truncated, soluble CR1 molecules can be expressed in mammalian cells by use of expression vectors such as the pTCS vectors described in Section 11.3.1. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the chimeric gene product in the specific fashion desired. Expression from certain promoters can be elevated in the presence of certain inducers; thus, expression of the genetically engineered CR1 protein may be controlled. Furthermore, different host cells have characteristic and specific mechanisms for the translational and post-translational processing and modification of proteins. Appropriate cell lines or host systems can be chosen to ensure the desired modification and processing of the expressed heterologous protein. For example, in one embodiment, expression in a bacterial system can be used to produce an unglycosylated CR1 protein with the deduced amino acid sequence of FIG. 1. Expression in yeast will produce a glycosylated product. In another embodiment, mammalian COS cells can be used to ensure "native" glycosylation of the heterologous CR1 protein. Furthermore, different vector/host expression systems may effect processing reactions such as proteolytic cleavages to different extents. Many such variously processed CR1 proteins can be produced and are within the scope of the present invention.

In a preferred embodiment of the invention, large scale production of soluble CR1 molecules may be carried out as described infra in Section 12.1 et seq.

5.3. Identification and Purification of the Expressed Gene Product

Once a recombinant which expresses the CR1 gene is identified, the gene product should be analyzed. This can be achieved by assays based on the physical, immunological, or functional properties of the product.

The CR1 proteins may be isolated and purified by standard methods including chromatography (e.g., ion exchange, affinity, and sizing column chromatography, high pressure liquid chromatography), centrifugation, differential solubility, or by any other standard technique for the purification of proteins.

In a preferred aspect of the invention detailed in the examples infra, large quantities of soluble CR1 can be purified by procedures involving HPLC (see Section 12.2 et seq.). As described infra, large-scale production of purified CR1 can be achieved by using an expression system which produces soluble CR1 as starting material, thus eliminating the requirement of solubilizing membrane-bound CR1 with detergents. The reduction of fetal calf serum concentrations in the bioreactor cultures and/or the use of alternative culture medias in these cultures eliminates the need to remove high concentrations of extraneous proteins from the soluble CR1-containing starting material during subsequent purification. Either cation HPLC or a combination of cation HPLC followed by anion exchange HPLC can be used for purification in this preferred aspect. Substantially pure soluble CR1 in high yield can thus be achieved in only one or two steps.

Alternatively, once a CR1 protein produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller, M., et al., 1984, Nature 310: 105–111).

In particular embodiments of the present invention, such CR1 proteins, whether produced by recombinant DNA techniques or by chemical synthetic methods, include but are not limited to those containing, as a primary amino acid sequence, all or part of the amino acid sequence substantially as depicted in FIG. 1, including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Nonconservative substitutions can also result in functionally equivalent proteins.

In one embodiment, substitutes for an amino acid within the CR1 sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are CR1 proteins which are differentially modified during or after translation, e.g., by glycosylation, proteolytic cleavage, etc.

In an example of the invention detailed infra, cloned recombinant CR1 expressed by transfected cells was shown to be indistinguishable from the F allotype of erythrocytes by SDS-PAGE (FIG. 14), capable of mediating the binding of sheep erythrocytes bearing either C4b or C3b, and able to reproduce the ligand specificity of CR1 (FIG. 13), and exhibit factor I co-factor activity for cleavage of the alpha polypeptide of C3(ma) (FIG. 15).

5.4. Structure of the CR1 Gene and Protein

The structure of the CR1 gene and protein can be analyzed by various methods known in the art, including but not limited to those described infra.

5.4.1. Genetic Analysis

The cloned DNA or cDNA corresponding to the CR1 gene can be analyzed by methods including but not limited to Southern hybridization (Southern, E. M., 1975, J. Mol. Biol. 98: 503–517), Northern hybridization (see e.g., Freeman et al., 1983, Proc. Natl. Acad. Sci. U.S.A. 80: 4094–4098), restriction endonuclease mapping (Maniatis, T., 1982, Molecular Cloning, A Laboratory Manual, Cold Spring Harbor Laboratory, Cold Spring Harbor, N.Y.), and DNA sequence analysis. The stringency of the hybridization conditions for both Southern and Northern hybridization can be manipulated to ensure detection of nucleic acids with the desired degree of relatedness to the specific CR1 probe used. For example, hybridization under low stringency conditions with a probe containing CR1 gene sequences encoding LHR-B and LHR-C, can be used to detect CR2 nucleic acid sequences.

Restriction endonuclease mapping can be used to roughly determine the genetic structure of the CR1 gene. In a particular embodiment, cleavage with restriction enzymes can be used to derive the restriction map shown in FIG. 2, infra. Restriction maps derived by restriction endonuclease cleavage can be confirmed by DNA sequence analysis.

DNA sequence analysis can be performed by any techniques known in the art, including but not limited to the method of Maxam and Gilbert (1980, Meth. Enzymol. 65: 499–560), the Sanger dideoxy method (Sanger, F., et al., 1977, Proc. Natl. Acad. Sci. U.S.A. 74: 5463), or use of an automated DNA sequenator (e.g., Applied Biosystems, Foster City, Cailf.). The cDNA sequence of the CR1 gene comprises the sequence substantially as depicted in FIG. 1, and described in Sections 6 and 7, infra.

5.4.2. Protein Analysis

The amino acid sequence of the CR1 protein can be derived by deduction from the DNA sequence, or alternatively, by direct sequencing of the protein, e.g., with an automated amino acid sequencer. The amino acid sequence of a representative CR1 protein comprises the sequence substantially as depicted in FIG. 1, and detailed in Section 6, infra. As described infra, all of the coding sequence of the F allotype CR1 has been cloned and, after cleavage of the signal peptide of 41 amino acids, the mature receptor contained 1998 amino acids including an extracellular domain of 1930 residues that forms 30 SCRs, 28 of which are organized into LHRs-A, -B, -C and -D, (FIG. 10), a single membrane spanning domain of 25 amino acids and a relatively short cytoplasmic domain of 43 amino acids.

Among the C3/C4 binding proteins that contain multiple SCRs, CR1 is unique in having groups of SCRs organized into LHRs. Comparison of the four LHRs of CR1 reveals that each is a composite of four types of SCRs: types a, b, c and d (FIG. 19). For example, the sequences of SCR-1 and -2 of LHR-A are only 62%, 62% and 57% identical to the first two SCRs of LHR-B, -C and -D, respectively. However, SCR-3 through SCR-7 differ from the corresponding SCRs of LHR-B at only a single position, and SCR-3 and -4 differ from those of LHR-C at only three positions (FIG. 10). Thus, some of the type "a" SCRs of LHR-A are also present in LHR-B and -C. The first two SCRs of LHR-B, which differ from those of LHR-A, are 99% identical with the corresponding SCRs of LHR-C, so that LHR-B and -C share the type "b" SCR at these positions. The fifth, sixth and seventh SCR of LHR-C are only 77% identical to the type "a" SCRs in LHR-A and -B at these positions, and are considered as type "c" SCRS. The first through fourth SCRs of LHR-D are relatively unique and are type "d", while the fifth through seventh SCRs are approximately 93% identical to the "c" type found in LHR-C.

The CR1 protein sequence can be further characterized by a hydrophilicity analysis (Hopp, T. and Woods, K., 1981, Proc. Natl. Acad. Sci. U.S.A. 78: 3824). A hydrophilicity profile can be used to identify the hydrophobic and hydrophilic regions of the CR1 protein and the corresponding regions of the gene sequence which encode such regions. A hydrophilicity profile of the COOH-terminus of the CR1 protein is depicted in FIG. 5.

Secondary structural analysis (Chou, P. and Fasman, G., 1974, Biochemistry 13: 222) can also be done, to predict regions of CR1 that assume specific secondary structures.

Other methods of structural analysis can also be employed. These include but are not limited to X-ray crystallography (Engstom, A., 1974, Biochem. Exp. Biol. 11: 7–13) and computer modeling (Fletterick, R. and Zoller, M. (eds.), 1986, Computer Graphics and Molecular Modeling, in Current Communications in Molecular Biology, Cold Spring Harbor Laboratory, Cold Spring Harbor, N.Y.).

5.5. CR1-Related Derivatives, Analogues, and Peptides

The production and use of derivatives, analogues, and peptides related to CR1 are also envisioned, and within the scope of the present invention. Such derivatives, analogues, or peptides which have the desired immunogenicity or antigenicity can be used, for example, in immunoassays, for immunization, therapeutically, etc. Such molecules which retain, or alternatively inhibit, a desired CR1 property, e.g., binding of C3b or C4b, regulation of complement activity, or promotion of immune stimulation or phagocytosis, etc., can be used as inducers, or inhibitors, respectively, of such property.

The CR1-related derivatives, analogues, and peptides of the invention can be produced by various methods known in the art. The manipulations which result in their production can occur at the gene or protein level. For example, the cloned CR1 gene can be modified by any of numerous strategies known in the art (Maniatis, T., 1982, Molecular Cloning, A Laboratory Manual, Cold Spring Harbor Laboratory, Cold Spring Harbor, N.Y.). The CR1 sequence can be cleaved at appropriate sites with restriction endonuclease(s), followed by further enzymatic modification if desired, isolated, and ligated in vitro (see Section 8, infra). In the production of the gene encoding a derivative, analogue, or peptide related to CR1, care should be taken to ensure that the modified gene remains within the same translational reading frame as CR1, uninterrupted by translational stop signals, in the gene region where the desired CR1-specific activity is encoded.

Additionally, the CR1 gene can be mutated in vitro or in vivo, to create and/or destroy translation, initiation, and/or termination sequences., or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253: 6551), use of TAB® linkers (Pharmacia), etc.

Manipulations of the CR1 sequence may also be made at the protein level. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogues and peptides related to CR1 can be chemically synthesized. For example, a peptide corresponding to a portion of CR1 which mediates the desired activity (e.g., C3b and/or C4b binding, immune stimulation, complement regulation, etc.) can be synthesized by use of a peptide synthesizer.

5.6. Uses of CR1

5.6.1. Assays and Diagnosis

CR1 proteins, analogues, derivatives, and subsequences thereof, and anti-CR1 antibodies, have uses in assays and in diagnostics. The molecules of the invention which demonstrate the desired CR1 property or function can be used to assay such property or function. For example, CR1 proteins or fragments thereof, which exhibit binding of C3b and/or C4b, in free and/or in complex forms, can be used in assays to measure the amount of such substances in a sample, e.g., a body fluid of a patient.

In a specific embodiment, full-length CR1 or a CR1 deletion mutant expressed on the cell surface (e.g., those described in Section 8, infra) having the ability to bind C3b (e.g., see Table II, Section 9, infra), iC3b or C4b (e.g., see Table II) can be used in assays to measure the levels of C3b, iC3b, or C4b, respectively, in a sample. In another embodiment, a CR1 protein or fragment thereof which is constructed by recombinant DNA technology to lack a transmembrane sequence, and is thus secreted, can be used.

In a particular embodiment, such a measurement of C3b and/or C4b can be relied on as an indication of complement activity, and can be useful in the diagnosis of inflammatory and immune system disorders. Such disorders include but are not limited to tissue damage due to burn- or myocardial infarct-induced trauma, adult respiratory distress syndrome (shock lung), autoimmune disorders such as rheumatoid arthritis, systemic lupus erythematosus, and other diseases or disorders involving undesirable or inappropriate complement activity (see, e.g., Miescher, P. A. and Muller-Eberhard, H. J., eds., 1976, Text Book of Immunopathology, 2d Ed., Vols. I and II, Grune and Stratton, New York; Sandberg, A. L., 1981, in Cellular Functions in Immunity and Inflammation, Oppenheim, J. J. et al., eds., Elsevier/North Holland, New York, p. 373; Conrow, R. B. et al., 1980, J. Med. Chem. 23: 242; Regal, J. F. and Pickering, R. H., 1983, Int. J. Immunopharmacol. 5: 71; Jacobs, H. S., 1980, Arch. Pathol. Lab. Med. 104: 617).

The CR1 protein and fragments thereof containing an epitope have uses in assays including but not limited to immunoassays. The immunoassays which can be used include but are not limited to competitive and noncompetitive assay systems using techniques such as radioimmunoassays, ELISA (enzyme linked immunosorbent assay), "sandwich" immunoassays, precipitin reactions, gel diffusion precipitin reactions, immunodiffusion assays, agglutination assays, complement-fixation assays, immunoradiometric assays, fluorescent immunoassays, protein A immunoassays, and immunoelectrophoresis assays, to name but a few.

CR1 genes and related nucleic acid sequences and subsequences, can be used in hybridization assays. Such hybridization assays can be used to monitor inflammatory or immune responses associated with CR1 expression, to diagnose certain disease states associated with changes in CR1 expression, to determine the CR1 allotype of a patient, and to detect the presence and/or expression of the CR1 gene and related genes (e.g., CR2).

5.6.2. Therapy

The CR1 protein and fragments, derivatives, and analogues thereof can be therapeutically useful in the modulation of functions mediated by CR1. Such functions include but are not limited to binding of C3b and/or C4b, in free or in complex forms, promotion of phagocytosis, complement regulation, immune stimulation, etc. Effective doses of the CR1 proteins and related molecules of the invention have therapeutic value for many of the diseases or disorders associated with such functions, such as immune or inflammatory disorders (e.g., those described supra in Section 5.6.1). For example, full-length CR1 or fragments thereof and related molecules which exhibit the desired activity can have therapeutic uses in the inhibition of complement by their ability to act as a factor I cofactor, promoting the irreversible inactivation of complement components C3b or C4b (Fearon, D. T., 1979, Proc. Natl. Acad. Sci. U.S.A. 76: 5867; Iida, K. and Nussenzweig, V., 1981, J. Exp. Med. 153: 1138), and/or by the ability to inhibit the alternative or classical C3 or C5 convertases.

In a specific embodiment of the invention, an expression vector can be constructed to encode a CR1 molecule which lacks the transmembrane region (e.g., by deletion carboxy-terminal to the arginine encoded by the most C-terminal SCR), resulting in the production of a soluble CR1 fragment. In one embodiment, such a fragment can retain the ability to bind C3b and/or C4b, in free or in complex forms. In a particular embodiment, such a soluble CR1 protein may no longer exhibit factor I cofactor activity. The soluble CR1 product can be administered in vivo to a patient, so that the soluble CR1 can effectively compete out binding of the C3b and/or C4b to the native cell-surface CR1, thus blocking cell-surface CR1 factor I cofactor activity, and increasing complement activity.

After C3b has covalently attached to particles and soluble immune complexes, the inactivation of C3b by proteolytic processing into iC3b and C3dg has two biologic consequences: preventing excessive activation of the complement system via the amplification pathway, and formation of ligands that can engage receptors other than CR1. The iC3b fragment cannot bind factor B so that conversion to this state blocks additional complement activation via the alternative pathway amplification loop. However, iC3b can be bound by CR1 and CR3, the two complement receptors that mediate phagocytosis by myelomonocytic cells. Therefore, the primary biologic consequence of C3b to iC3b conversion is cessation of complement activation without interference with CR1- and CR3-mediated clearance of the C3 -coated complex. In contrast, the additional conversion of iC3b to C3dg creates a fragment that interacts only with CR2 and not with CR1 and CR3. This circumstance limits complement-dependent binding of the C3dg-bearing complex to cell types expressing CR2, which include B lymphocytes, follicular dendritic cells and perhaps epithelial cells of the dermis, and diminishes or excludes interaction with phagocytic cell types. The biologic consequence of this altered pattern of cellular association would be targeting of the C3dg-bearing complexes to cells involved in the afferent phase of the immune response rather than to cells involved in clearance and degradation of particles and complexes. Therefore, CR1 molecules may be used therapeutically not only to affect the clearance process, but also in the targeting of complexes to the CR2-bearing cell types that participate in antigen presentation and antibody production.

In an alternative embodiment, a CR1 protein or fragment thereof which can bind C3b or C4b, and/or retains the ability to inhibit the alternative or classical C3 or C5 convertases, or retains factor I cofactor activity, can be used to promote complement inactivation. In such an embodiment, the CR1 protein or fragment can be valuable in the treatment of disorders which involve undesirable or inappropriate complement activity (e.g., shock lung, tissue damage due to burn or ischemic heart conditions, autoimmune disorders, inflammatory conditions, etc.).

In a specific embodiment detailed in the examples Sections 11–14 infra, a soluble CR1 molecule can be expressed which retains a desired functional activity, as demonstrated, e.g., by the ability to inhibit classical complement-mediated hemolysis, classical C5a production, classical C3a production, or neutrophil oxidative burst in vitro. In a particular embodiment, such a soluble CR1 molecule can be used to reduce inflammation and its detrimental effects, or to reduce myocardial infarct size or prevent reperfusion injury, etc. Such CR1 molecules useful for in vivo therapy may be tested in various model systems known in the art, including but not limited to the reversed passive Arthrus reaction (see Section 14.1) and a rat myocardial infarct model (see Section 14.3).

In another embodiment of the invention, a fragment of CR1, or an analogue or derivative thereof, which is shown to inhibit a desired CR1 property or function, can be used to prevent or treat diseases or disorders associated with that function.

Various delivery systems are known and can be used for delivery of CR1 and related molecules, e.g., encapsulation in liposomes, expression by hematopoietic stem cell progeny in gene therapy, etc. Other methods of introduction include but are not limited to intradermal, intramuscular, intraperitoneal, intravenous, subcutaneous, intranasal, and oral routes.

EXAMPLE 6

The Cloning and Sequencing of the Human C3b/C4b Receptor (CR1)

In the examples detailed herein, we describe the cloning and nucleotide sequence of 5.5 kilobase pairs (kb) of the CR1 coding region (Klickstein, L. B., et al., 1987, J. Exp. Med. 165: 1095–1112).

Ten overlapping CR1 cDNA clones that span 5.5 kb were isolated from a tonsillar library and sequenced in whole or in part. A single long open reading frame beginning at the 5' end of the clones and extending 4.7 kb downstream to a stop codon was identified. This sequence represents ~80% of the estimated 6 kb of coding sequence for the F allotype of CR1.

Three tandem, direct, long homologous repeats (LHRs) of 450 amino acids were identified. Analysis of the sequences of tryptic peptides provided evidence for a fourth LHR in the F allotype of CR1. Amino acid identity between the LHRs ranged from 70% between the first and third repeats to 99% between the $NH_2$-terminal 250 amino acids of the first and second repeats. Each LHR comprises seven short consensus repeats (SCRs) of 60–70 amino acids that resemble the SCRs of other C3/C4 binding proteins, such as complement receptor type 2, factors B and H, C4 binding protein, and C2. Two additional SCRs join the LHRs to a single membrane-spanning domain of 25 amino acids: thus, the F allotype of CR1 probably contains at least 30 SCRs, 23 of which have been sequenced. Each SCR is predicted to form a triple loop structure in which the four conserved half-cystines form disulfide linkages. The linear alignment of 30 SCRs as a semi-rigid structure would extend 1,140 Angstroms from the plasma membrane and might facilitate the interaction of CR1 with C3b and C4b located within the interstices of immune complexes and microbial cell walls. The COOH-terminal cytoplasmic domain of 43 residues contains a six amino acid sequence that is homologous to the sequence in the epidermal growth factor receptor that is phosphorylated by protein kinase C.

6.1. Materials and Methods

6.1.1. Isolation and Sequence of CR1 Tryptic Peptides

CR1 was purified from washed human erythrocyte membranes by sequential Matrex Red A and YZ-1 monoclonal antibody affinity chromatography (Wong, W. W., et al., 1985, J. Immunol. Methods 82: 303). Tryptic peptides were prepared and isolated by sequential gradient and isocratic reversephase HPLC (high performance liquid chromatography) as described (wong, W. W., et al., 1985, Proc. Natl. Acad. Sci. U.S.A. 82: 7711). Tryptic peptide analysis was performed with a 470A Protein Sequencer (Applied Biosystems, Inc., Foster City, Calif.), and analysis of each degradative cycle was achieved using a 120 PTH-amino acid analyzer (Applied Biosystems, Inc.).

6.1.2. Isolation of cDNA Clones and Genomic Clones

A cDNA library was constructed in λgt11 from human tonsilar poly(A)$^+$ RNA as described (Wong, W. W., et al., 1985, Proc. Natl. Acad. Sci. U.S.A. 82: 7711). By RNA blot hybridization, the tonsil donor was homozygous for the F allele of CR1 (id.). The cDNA was selected on an agarose gel to include fractions between 2 and 7 kb before the cloning steps. The initial complexity of the library was $4.5 \times 10^6$ recombinants per 100 ng cDNA and the library was amplified in *Escherichia coli* strain Y1088. The library was screened (Maniatis, T., et al., 1982, Molecular Cloning, A Laboratory Manual, Cold Spring Harbor Laboratory, Cold Spring Harbor, N.Y.) with CR1 probes, CR1-1 (ATCC accession nos. 57330 (*E. coli* containing CR1-1 plasmid), 57331 (purified CR1-1 DNA)) and CR1-2 (Wong, W. W., et al., 1985, Proc. Natl. Acad. Sci. U.S.A. 82: 7711), that had been radiolabeled to a specific activity of $2-8 \times 10^8$ cpm/μg by nick translation. Hybridization was performed in 50% formamide, 5× SSC (1× SSC: 15 mM sodium citrate, 150 mM sodium chloride) at 43° C. and filters were washed at 60° C. in 0.2× SSC, conditions that do not allow the detection of CR2 cDNA clones (Weis, J. J., et al., 1986, Proc. Natl. Acad. Sci. U.S.A. 83: 5639). Positive clones were plaque-purified twice before restriction mapping and DNA sequence analysis.

A genomic library was constructed in EMBL-3 with 15–20 kb fragments produced by partial digestion of human leukocyte DNA with Sau3AI. The initial complexity was $1.2 \times 10^6$, and the library was amplified in *E. coli* strain P2392. The library was also screened with the cDNA probes CR1-1 and CR1-2 (Wong, W. W., et al., 1985, Proc. Natl. Acad. Sci. U.S.A. 82: 7711).

6.1.3. DNA Sequence Analysis

Restriction fragments of the cDNA clones were subcloned in M13mp18 or M13mp19 and sequenced by the dideoxy-nucleotide chain termination method (Sanger, F., et al., 1977, Proc. Natl. Acad. Sci. U.S.A. 74: 5463). Some clones were sequenced in whole or in part by first creating ordered deletion mutants using exonuclease III (Henikoff, S., 1984, Gene 28: 351). Each region was sequenced on both strands and in most cases each region was sequenced on M13 subclones constructed from two independently isolated cDNA clones (FIG. 2). Sequence data were analyzed with the University of Wisconsin Genetics Computer Group package (Madison, Wis.).

6.2. Results

6.2.1. Nucleotide Sequence of the CR1 Gene

A size-selected tonsillar cDNA library was screened with the CR1-1 and CR1-2 probes obtained from the CR1 cDNA clone, λT8.3 (Wong, W. W., et al., 1985, Proc. Natl. Acad. Sci. U.S.A. 82: 7711). Fifteen positive phage were identified out of $1.5 \times 10^6$ recombinants and 13 of these represented distinct clones. Ten were restriction mapped and sequenced in whole or in part by the dideoxynucleotide chain termination method. The cDNA clones were aligned on the basis of overlapping sequence identity (FIG. 2) and were found to span 5.5 kb (FIGS. 3A–3D). A single long open reading frame was identified beginning at the 5' end of the cDNA clones and extending 4.7 kb downstream to a stop codon. The coding sequence for CR1 in this library is expected to be 6 kb, based on an estimated 220,000 dalton molecular weight for the nonglycosylated receptor (Wong, W. W., et al., 1983, J. Clin. Invest. 72: 685). Thus, these clones span ~80% of the estimated coding sequence.

Clones T49.1 and T55.1 contain coding sequence at their 5' ends, indicating that additional 5' coding and noncoding sequences remain to be identified. In the 3' region, the overlapping clones, T8.2, T43.1 and T87.1, contain the transmembrane and cytoplasmic regions encoded by an identical sequence in each clone. The clone extending most 3', T8.2, contains 807 bp of untranslated sequence without a poly(A) sequence. Clone T8.3 contains a 91-bp deletion of nucleotides 1,406–1,497 and clone T40.1 contains a 9-bp deletion of nucleotides 1,498–1,507 relative to the sequences found in clones T6.1 and T55.1. These deletions occurred in regions having sequences homologous to 5' splice sites and may represent splicing errors in the mRNA. Clones T49.1 and T55.1 contain a 110 bp insertion between nucleotides 147 and 148 of the open reading frame (FIGS. 3A–3D). This sequence is judged to be a portion of an intron because it did not hybridize to blots of tonsillar poly(A)$^+$ RNA, it contains a 5' splice site (Breathnach, R., et al., 1978, Proc. Natl. Acad. Sci. U.S.A. 75: 4853) (FIGS. 3A–3D), it is flanked by cDNA sequences in CR1 genomic clones, and it shifts the reading frame. Clone T9.4 contains 0.88 kb of intervening sequence at the 3' end that does not hybridize to blots of tonsillar poly(A)$^+$ RNA.

6.2.2. Analysis of the Nucleotide and Amino Acid Sequence of CR1

Dot matrix analysis of the nucleotide sequence of CR1 (FIGS. 3A–3D) revealed two types of internal homologies (FIG. 4). The first type of internal homology is represented by the bold, uninterrupted lines that indicate the presence of three tandem, direct, highly homologous repeats of 1.35 kb. These nucleotide sequences encode the long homologous repeats (LHRs) of CR1. The second type of repeat is represented by the dashed parallel lines that indicate regions of lesser homology. These sequences occur every 190–210 nucleotides and encode the short consensus repeats (SCRs) of CR1.

The amino acid sequence deduced from the cDNA sequence is presented in FIG. 5B and the three LHRs, designated LHR-B, LHR-C and LHR-D, are aligned to demonstrate their homology. LHR-B extends from residue 1 through residue 438, LHR-C corresponds to residues 439–891, and LHR-D extends from residue 892 through 1,341. Residues 451–694 of LHR-C are 99% identical to residues 1–244 of LHR-B, but only 61% identical to the corresponding residues of LHR-D. In contrast, residues 695–891 of LHR-C are 91% identical to residues 1,148–1,341 of LHR-D but only 76% identical to the corresponding region of LHR-B. Thus, LHR-C appears to be a hybrid that comprises sequences most homologous to the first half of LHR-B and the second half of LHR-D. The LHRs are followed by two SCRs that are not repeated, a 25 residue hydrophobic segment and a 43 amino acid COOH-terminal region with no sequence homology to the SCRs (FIG. 5B).

The 5' 1.3 kb of the CR1 coding sequence represents a fourth LHR, LHR-A (see FIGS. 1A–1P, supra, and Section 7, infra). This conclusion was supported by analysis of tryptic peptides of erythrocyte CR1. Ten tryptic peptides have sequences identical to the amino acid sequences derived from the cDNA clones (Table I).

TABLE I

CR1 TRYPTIC PEPTIDES FOUND IN THE DERIVED AMINO ACID SEQUENCE*

| Peptide Number | Amino acid sequence | Residue Numbers in the Derived Sequence |
|---|---|---|
| 66 | VDFVCDEGFQLKGS-A | 330–345 |
| 28 | GAASL----QG-WSPEAP | 732–749, 1,185–1,202 |
| 49 | ------------IFC-NP-AIL | 805–826, 1,258–1,279 |
| 35 | CQALNKWEPELPSCSR | 228–243, 678–693 |
| 41c | DKDNFSPGQEVFYSCEPGYDLR | 260–281 |
| 34b | AV-YTCDPHPDRGTSFDLIGESTIR | 393–417 |
| 44d | VCQPPPEILHG | 694–704, 1,147–1,157 |
| 54d | VFELVGEPSIYCTSNDDQVGIWSGPAPQ | 152–179, 602–629 |
| 57b | YECRPEYYGRPFS | 19–31, 469–481 |
| 39b | LIGHSSAECILSGNAA | 85–100 |

*Tryptic peptides from human erythrocyte CR1 found in the derived amino acid sequence. The number ranges in the right-hand column indicate the location of the peptide in the derived amino acid sequence. Each dash in peptides 66, 28 and 49 indicates multiple residues were identified at that cycle. The dash in peptide 34b indicates no residue was identified at that cycle.

Figure 6B:
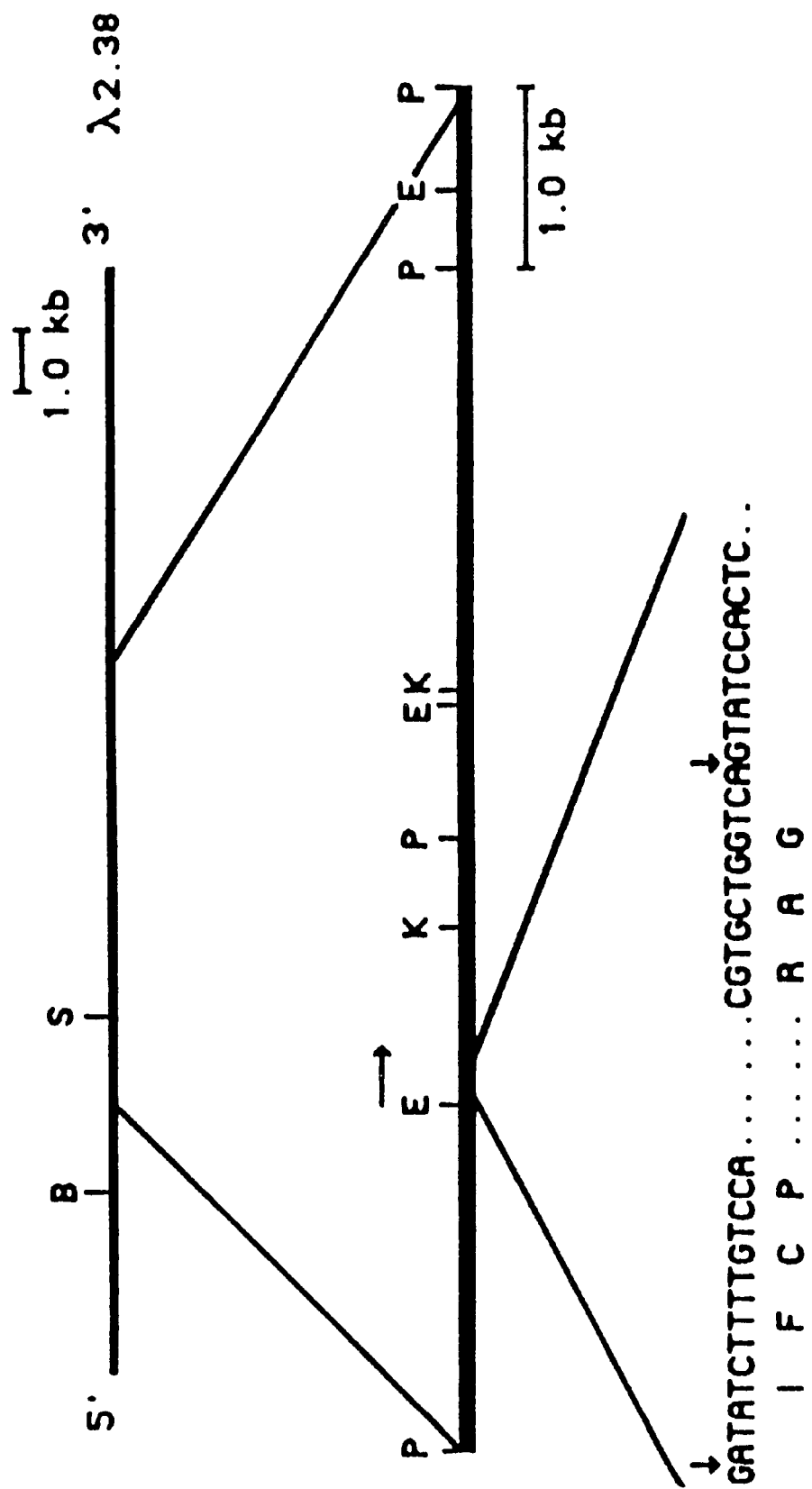

Each LHR comprises seven 60–70 amino acid SCRs that characterize the family of C3 and C4 binding proteins (C4bp) (FIG. 6A). Maximal homology between the 23 SCRs of CR1 was observed by introducing spaces in the alignment of the sequences (FIG. 6A). Altogether, 29 of the average 65 residues in each repeat are conserved. There are six residues that are present in all SCRs: the four half-cystines that are in similar relative positions suggesting that each may be involved in a critical disulfide linkage, and the tryptophan and the second glycine after the second half-cystine (FIG. 6A). Secondary structure analysis of the sequences between the invariant half-cystines using the algorithm of Chou and Fasman (Chou, P. Y. and Fasman, G. D., 1974, Biochemistry 13: 222) predicted high probability β-turn formation and low probability α-helix formation. Sequence analysis of two CR1 genomic clones, 2.38 (FIG. 6B) and 2.46, indicates that SCR-14 (FIG. 6A) is encoded by a single exon and that the COOH-terminus of SCR-23 corresponds to the end of an exon. Thus, the SCRs of CR1 may be encoded by separate exons as has been shown for the SCRs of factor B (Campbell, R. D. and Bentley, D. R., 1985, Immunol. Rev. 87: 19) and of the IL-2-R (Leonard, W. J., et al., 1985, Science 230: 633).

The consensus sequence of the CR1 SCRs is compared with the SCRs of the other members of the superfamily having this characteristic structure (FIG. 7). These members include not only proteins having C3/C4 binding function, CR2 (Weis, J. J., et al., 1986, Proc. Natl. Acad. Sci. U.S.A. 83: 5639), C4bp (Chung, L. P., et al., 1985, Biochem. J. 230: 133), factor H (Kristensen, T., et al., 1986, J. Immunol. 136: 3407), factor B (Morley, B. J. and Campbell, R. D., 1984, EMBO J. 3: 153; Mole, J. E., et al., 1984, J. Biol. Chem. 259: 3407), and C2 (Bentley, D. R. and Porter, R. R., 1984, Proc. Natl. Acad. Sci. U.S.A. 81: 1212; Gagnon, J., 1984, Philos. Trans. R. Soc. Lond. B. Biol. Sci. 306: 301), but also the proteins not known to have this function, such as the interleukin-2 receptor (Leonard, W. J., et al., 1985, Science 230: 633), $\beta_2$-glycoprotein I (Lozier, J., et al., 1984, Proc. Natl. Acad. Sci. U.S.A. 81: 3640), C1r (Leytus, S. P., et al., 1986, Biochemistry 25: 4855), haptoglobin α chain (Kurosky, A., et al., 1980, Proc. Natl. Acad. Sci. U.S.A. 77: 3388), and factor XIIIb (Ichinose, A., et al., 1986, Biochemistry 25: 4633). The half-cystine residues are invariant in the SCRs of all proteins, except haptoglobin which lacks the third half-cystine. The tryptophan is also invariant with the exception of the fifth SCR in $\beta_2$-glycoprotein I and two of the repeats in factor XIIIb. Other residues that are conserved but not present in each SCR tend to cluster about the half-cystines. There is only one free thiol group in factor B and C2 (Christie, D. L. and Gagnon, J., 1982, Biochem. J. 201: 555; Parkes, C., et al., 1983, Biochem. J. 213: 201), and in the SCRs of $\beta_2$-glycoprotein I, the first half-cystine is disulfide-linked to the third and the second to the fourth (Lozier, J., et al., 1984, Proc. Natl. Acad. Sci. U.S.A. 81: 3640).

In the derived amino acid sequence of CR1, there are 17 potential sites for N-linked oligosaccharides and all of them are in the extracellular region (FIG. 6A). Molecular weight differences between CR1 synthesized in the presence and absence of tunicamycin (Lublin, D. M., et al., 1986, J. Biol. Chem. 261: 5736) and analysis of glucosamine content (Sim, R. B., 1985, Biochem. J. 232: 883) suggest the presence of only 6–8 N-linked complex oligosaccharides, indicating that all potential sites are not used. For example, the asparagine at residue 263 of the derived amino acid sequence (FIG. 5B) was identified in peptide 41c (Table I), indicating absence of glycosylation at this site. In contrast, the unidentified amino acid in peptide 34b probably corresponds to a glycosylated asparagine at residue 395.

Figure 5C:
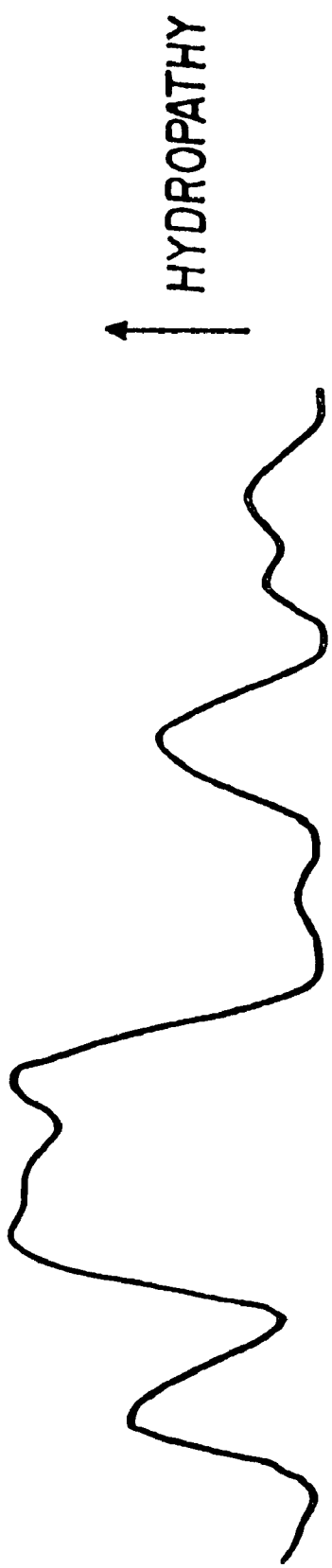

The only nonrepetitive CR1 sequences identified in the 5.5 kb of cDNA are located in the COOH-terminal region. A secondary structure analysis of this region identifies a single 25-residue putative membrane-spanning segment having strong hydrophobic character and high potential for α-helix formation (FIG. 5C). This sequence is immediately followed by four positively charged residues, a characteristic of many membrane proteins. The presumed cytoplasmic region of CR1 comprises 43 residues and contains a six amino acid sequence, VHPRTL, which is homologous to the sequence VRKRTL, a site of protein kinase C phosphorylation in the epidermal growth factor (EGF) receptor and the erbB oncogene product (Hunter, T., et al., 1984, Nature 311: 480; Davis, R. J. and Czech, M. P., 1985, Proc. Natl. Acad. Sci. U.S.A. 82: 1974). There are no tyrosine residues in the cytoplasmic region of tonsillar CR1.

6.3. Discussion

Figure 8B:
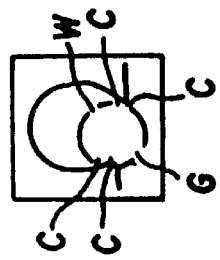

Approximately 80% of the primary structure of the F allotype of CR1 has been obtained by sequencing overlapping cDNA clones. The most unusual structural feature of CR1 observed in this analysis is the presence of tandem, direct LHRs of 450 amino acids, four of which are predicted to occur in the F allotype of CR1 that has an estimated polypeptide chain length of 2,000 residues (Wong, W. W., et al., 1983, J. Clin. Invest. 72: 685; Sim, R. B., 1985, Biochem. J. 232: 883). Three of the LHRs have been cloned and sequenced while evidence for the existence of the fourth was provided by the analysis of tryptic peptides. Each LHR is comprised of seven SCRs which are the basic structural elements of other C3/C4 binding proteins. The conservation of the four half-cystines per SCR, the probable involvement of the first and third and the second and fourth half-cystines in disulfide linkages (Lozier, J., et al., 1984, Proc. Natl. Acad. Sci. U.S.A. 81: 3640) and the presence of conserved amino acids such as proline, glycine and asparagine which are frequently found in β-turns (Rose, G. D., et al., 1985, Adv. Protein Chem. 37: 1) lead to the proposal that an SCR forms a triple loop structure maintained by disulfide linkages (FIG. 8B). This role for the half-cystine residues is supported by the finding that mildly trypsin-treated CR1 (Sim, R. B., 1985, Biochem. J. 232: 883) and factor H (Sim, R. B. and DiScipio, R. G., 1982, Biochem. J. 205: 285) migrate as intact molecules when analyzed by SDS-polyacrylamide gel electrophoresis (PAGE) under non-reducing conditions and as multiple tryptic fragments after reduction.

This series of tandemly repeated SCRs is predicted to form an elongated structure (FIG. 8A) as has been proposed for factor H and for each subunit of human C4bp (Sim, R. B. and DiScipio, R. G., 1982, Biochem. J. 205: 285; Whaley, K. and Ruddy, S., 1976, J. Exp. Med. 144: 1147; Dahlback, B., et al., 1983, Proc. Natl. Acad. Sci. U.S.A. 80: 3461). Electron microscopic studies of the subunits of C4bp have indicated dimensions of 300×30 Angstroms (Dahlback, B., et al., 1983, Proc. Natl. Acad. Sci. U.S.A. 80: 3461). As each subunit is composed of eight SCRs (Chung, L. P., et al., 1985, Biochem. J. 230: 133), an individual SCR is calculated to be 38×30 Angstroms. Assuming that the SCRs of CR1 have similar dimensions and that the F allotype has 30 SCRS, the receptor could extend as much as 1,140 Angstroms from the cell membrane. Consistent with this prediction of CR1 structure is the earlier finding that ferritin-labeled antibody bound to CR1 on neutrophils was frequently 500 Angstroms from the outer leaflet of the plasma membrane (Abrahamson, D. R. and Fearon, D. T., 1983, Lab. Invest. 48: 162). Such an elongated structure of CR1 would facilitate the interaction of receptor-bearing cells with C3b that has covalently bound to relatively inaccessible sites within immune complexes and microbial cell surfaces.

The finding that the SCR is the major, and perhaps only, extracytoplasmic element of CR1 provides structural evidence for a close relationship between the receptor and factor H and C4bp, two plasma proteins that are exclusively or predominantly composed of SCRs (Chung, L. P., et al., 1985, Biochem. J. 230: 133; Kristensen, T., et al., 1986, J. Immunol. 136: 3407). CR1 was initially isolated as an erythrocyte membrane protein having factor H-like activity after detergent solubilization (Fearon, D. T., 1979, Proc. Natl. Acad. Sci. U.S.A. 76: 5867), and it was found subsequently to have the regulatory functions of factor H and C4bp when residing on the plasma membrane (Iida, K. and Nussenzweig, V., 1981, J. Exp. Med. 153: 1138). By analysis of the inheritance of structural polymorphisms of CR1, factor H, and C4bp, the genes encoding these three proteins were shown to be linked (de Cordoba, R., et al., 1985, J. Exp. Med. 161: 1189), and the locus for this linkage group and for the structurally related receptor, CR2, have been shown recently by in situ hybridization and by the analysis of somatic cell hybrids to be on the long arm of chromosome 1, band q32 (Weis, J. H., et al., 1987, J. Immunol. 138: 312). Before the present study, the only evidence for a structural relationship between these proteins was a significant similarity in their amino acid compositions (Wong, W. W., et al., 1985, J. Immunol. Methods 82: 303). Therefore, the present finding of at least 23 SCRs in CR1 constitutes the direct and formal demonstration of a structural relationship of the receptor with factor H and C4bp (Chung, L. P., et al., 1985, Biochem. J. 230: 133; Kristensen, T., et al., 1986, J. Immunol. 136: 3407), proteins with similar functions, and with the Ba and C2b fragments of factor B and C2 (Morley, B. J. and Campbell, R. D., 1984, EMBO J. 3: 153; Mole, J. E., et al., 1984, J. Biol. Chem. 259: 3407; Bentley, D. R. and Porter, R. R., 1984, Proc. Natl. Acad. Sci. U.S.A. 81: 1212; Gagnon, J., 1984, Philos. Trans. R. Soc. Lond. B Biol. Sci. 306: 301), components that form enzymatic complexes with C3b and C4b, respectively. However, the SCR is also found in several noncomplement proteins (Campbell, R. D., and Bentley, D. R., 1985, Immunol. Rev. 87: 19; Lozier, J., et al., 1984, Proc. Natl. Acad. Sci. U.S.A. 81: 3640; Leytus, S. P., et al., 1986, Biochemistry 25: 4855; Kurosky, A., et al., 1980, Proc. Natl. Acad. Sci. U.S.A. 77: 3388; Ichinose, A., et al., 1986, Biochemistry 25: 4633) (FIG. 7), indicating that it does not necessarily represent a C3/C4 binding structure.

Among the proteins having SCRs, CR1 is unique in having organized this basic structure and genetic unit into the higher order structural unit of the LHR. Analysis of a 14.5 kb BamHI fragment of genomic DNA that is associated with expression of the S allotype has suggested that at least one repeating genomic unit in CR1 is an extended segment of DNA containing the exons encoding at least five SCRs and their flanking introns (Wong, W. W., et al., 1986, J. Exp. Med. 164: 1531). These studies have also suggested that the S allele contains an additional copy of this genomic unit compared with the number present in the F allele. This observation, combined with a tryptic peptide mapping study (Nickells, M. W., et al., 1986, Mol. Immunol. 23: 661) and the present finding that an LHR represents a peptide of ~40–50 kD allows us to predict the presence in the S allotype (290 kD) of an additional LHR relative to the estimate of four LHRs in the F allotype (250,000 daltons molecular weight).

In addition to providing evidence for duplication events, the sequences of the LHRs also suggest that conversion events have occurred within the CR1 gene. LHR-B and -D are 67% identical to each other throughout their length, whereas LHR-C is 99% identical to LHR-B in the $NH_2$-terminal four SCRs and 91% identical to LHR-D in the COOH-terminal three SCRS. This organization could not have occurred by a single recombinational event between identical parental alleles in the origin of this hybrid LHR.

Rather, the hybrid LHR may have arisen by gene conversion (Atchison, M. and Adesnik, M., 1986, Proc. Natl. Acad. Sci. U.S.A. 83: 2300) in which sequences in an LHR-C precursor were replaced by sequences present in LHR-B or LHR-D. The near complete identity and precise alignment of homologous sequences in these LHRs (FIG. 5B) also may have been maintained by a mechanism involving gene conversion. Analysis of the extent of homology between intervening sequences of those segments of the CR1 gene encoding the LHRs should determine whether gene conversion or selection based on functional constraints have strictly limited sequence divergence.

Although a previous study suggested that CR1 is monovalent (Wilson, J. G., et al., 1982, N. Engl. J. Med. 307: 981), each LIR might represent a single C3b/C4b binding domain, which would make the receptor multivalent and adapted for the binding of complexes bearing multiple molecules of C3b and C4b. Alternatively, distinct LHRs might be responsible for binding C3b and C4b, respectively (see Section 9, infra), providing a structural basis for the combination of factor H and C4bp activities in CR1. Finally the LHRs of CR1 may represent structural domains that serve to extend CR1 from the plasma membrane, as suggested by the proposed structural model (FIG. 8A), and SCRs at the $NH_2$-terminal region bind C3b and C4b, as has been found for factor H (Sim, R. B. and DiScipio, R. G., 1982, Biochem. J. 205: 285; Alsenz, J., et al., 1984, Biochem. J. 224: 389).

Activation of protein kinase C by phorbol esters induces phosphorylation of CR1 in neutrophils, monocytes, and eosinophils (Changelian, P. S. and Fearon, D. T., 1986, J. Exp. Med. 163: 101) and the CR1 cytoplasmic domain of 43 amino acids has a sequence that is homologous to a site that is phosphorylated by protein kinase C in the epidermal growth factor receptor (Hunger, T., et al., 1984, Nature 311: 480; Davis, R. J. and Czech, M. P., 1985, Proc. Natl. Acad. Sci. U.S.A. 82: 1974). However, this cytoplasmic sequence, which was found in three independent clones of the tonsillar library, is most likely that of B cell CR1, which is not phosphorylated after activation of protein kinase C (Changelian, P. S. and Fearon, D. T., 1986, J. Exp. Med. 163: 101).

7. EXAMPLE:

CR1 5' cDNA Sequences Contain a Fourth Long Homologous Repeat

Analysis of a partial cDNA sequence of CR1 revealed a strucure in which three LHRs, LHR-B, LHR-C, LHR-D, of 450 amino acids were each comprised of seven short consensus repeats (SCR) of 65 amino acids characteristic of C3/C4 binding proteins (see Section 6, supra). In the examples described herein, we describe the cloning and nucleotide sequence of a fourth amino-terminal LHR, LHR-A (Klickstein, L. B., et al., 1987, Complement 4: 180) by the sequencing of 5' cDNA clones. Analysis of LHR-A revealed that it is 99% homologous to LHR-B in the five 3' SCRs, but only 61% homologous in the two 5' SCRs.

7.1. Materials and Methods

7.1.1. Construction of a cDNA Library

A selectively primed cDNA library, λHH, was constructed from 3 μg of poly (A)$^+$ RNA purified from DMSO-induced cells as described (Chirgwin, J. M. et al., 1979, Biochemistry 18: 5290; Aviv, H. and Leder, P., 1972, Proc. Natl. Acad. Sci. U.S.A. 69: 1408; Ausubel, F. M., et al., 1987, Current Protocols in Molecular Biology, John Wiley & Sons, New York) with the following modifications. LK35.1, a 35-mer oligonucleotide, 5'-TGAAGTCATC ACAGGATTTC ACTTCACATG TGGGG-3', was used in place of oligo(dT)$_{12-18}$ and 40 μCi of α$^{32}$P-dCTP were added during second strand synthesis. One third of the cDNA was cloned in λgt11 and a cDNA library was constructed from human tonsilar poly (A)$^+$ RNA as described in Section 6.1.2, supra. 750,000 independent recombinants were obtained.

7.1.2. Isolation of Clones, Probes, and DNA Sequence Analysis

The probes used for screening cDNA libraries were CR1-1 (Wong, W. W., et al., 1985, Proc. Natl. Acad. Sci. U.S.A. 82: 7711) (ATCC accession no. 57331), CR-2 (Wong, W. W., et al., supra), CR1-4 (Wong, W. W. et al., 1986, J. Exp. Med. 164: 1531), and CR1-18, a 252 bp Sau3AI fragment from the 0.5 kb EcoRI fragment of cDNA clone λH3.1 corresponding to nucleotides 101–352 in FIG. 1A. Under conditions of high stringency, CR1-18 hybridizes only to cDNA clones encoding either the $NH_2$-terminal SCR of LHR-A or the signal peptide. The inserts of the cDNA clones were sequenced by the dideoxynucleotide technique (Sanger, F., et al., 1977, Proc. Natl. Acad. Sci. U.S.A. 74: 5463) after subcloning fragments into M13mp18 and M13mp19 (Yanisch-Perron, C. et al., 1985, Gene 28: 351).

7.2. Results

A specifically primed λgt11 cDNA library, λHH, that contained 7.5×10$^5$ recombinants was prepared with cDNA synthesized from poly (A)$^+$ RNA from DMSO induced HL-60 cells. These cells express only the F allotype of CR1 (Lublin, D. M., et al., 1986, J. Biol. Chem. 261: 5736) which is predicted to have four LHRs (Lapata, M. A., et al., 1984, Nucl. Acids Res. 12: 5707). The primer, LK35.1, was an antisense 35-mer corresponding to nucleotides 896–930 of the partial cDNA sequence of CR1 presented in FIGS. 3A–3D. This oligonucleotide was shown to hybridize to LHR-B, LHR-C and LHR-D under the conditions of reverse transcription. Two hundred and fifty positive clones were identified in a plating of 3.8×10$^5$ unamplified recombinant phage screened with a mixture of the CR1 cDNA probes, CR1-1 and CR1-4. Thirty-eight positive clones were picked and plaque purified. Southern blots of EcoRI-digested DNA from these clones were screened with the 23-mer oligonucleotide, KS23.1, 5'-CTGAGCGTAC CCAAAGG-GAC AAG-3', corresponding to nucleotides 763–785 of the partial CR1 cDNA sequence of FIG. 3. This probe hybridizes under conditions of high stringency at a single site in the sequence encoding LHR-B but not to sequences encoding LHR-C or LHR-D. The insert of clone λH7.1 (FIG. 9) contained three EcoRI fragments of 1.0 kb, 0.9 kb and 0.4 kb and the two larger fragments hybridized to KS23.1, indicating that this clone contained sequences coding for the 3' 5/7 of LHR-A and all of LHR-B. This finding confirmed that LHR-A is highly homologous to LHR-B. Clone λH3.1 (FIG. 9) contained a single KS23.1-positive EcoRI fragment of 1.0 kb and a 5', 0.5 kb fragment that hybridized weakly with CR1-4 at high stringency. This clone was considered to contain the additional 5' sequence completing LHR-A, including SCRs -1 and -2 and 0.1 kb of upstream sequence. None of the remaining 36 clones, all of which hybridized with CR1-1, were detected with the probe, CR1-18, a 252 bp Sau3AI fragment from the 0.5 kb EcoRI fragment of clone λH3.1 that does not hybridize to sequences encoding LHR-B, -C or -D.

DNA sequence analysis of λH3.1 revealed that the open reading frame continued to the 5' end of the cDNA, indicating that the clone did not extend to the translational start site. Therefore, the cDNA libraries, λHH and λS2T, were rescreened with the probe CR1-18 to identify one clone from each, λH10.3 and λT109.1, respectively. The EcoRI fragments of these clones that hybridized with CR1-18 were sequenced as were the inserts from the clones, λH3.1 and λH7.1. The composite sequence is presented in FIGS. 1A–1D such that the nucleotide following number 1531 in FIG. 1D is nucleotide #1 in FIG. 3A. The overlapping sequences of the cDNA clones from the HL-60 and tonsillar libraries are identical.

Immediately upstream of LHR-A, clones λH10.3 and λT109.1 contain identical putative hydrophobic leader sequences (Von Heijne, G., 1986, Nucl. Acids Res. 14: 4683) encoding 41 amino acids, including an ATG matching the consensus NNA/GNNATGG proposed for eukaryotic translation initiation sites (FIG. 10) (Kozak, M., 1986, Cell 44: 283). A second ATG, located six codons upstream of the chosen ATG and just downstream of an in-frame stop codon, is a poor match for this consensus sequence. The first three amino acids of this leader sequence for CR1, MGA, are the same as those reported for CR2. The sequences of these two clones diverge upstream of the ATG and that from clone λ10.3 is believed to represent a portion of an intervening sequence, as has been described for other CR1 cDNA clones in Section 6, supra.

The signal peptidase cleavage is predicted (Von Heijne, G., 1986, Nucl. Acids Res. 14: 4683) to occur between glycine-46 and glutamine-47, suggesting that the blocked $NH_2$-terminus of CR1 (Wong., W. W., et al., 1985, J. Immunol. Methods 82: 303; Holeis, V. M., et al., 1986, Complement 3: 63) may be due to the presence of a pyrrolidone amide. The first two SCRs of the $NH_2$-terminal LHR-A contained in these clones are only 61% identical to the corresponding region of LHR-B, whereas SCRs 3–7 of LHR-A are 99% identical to the corresponding SCRs of LHR-B (FIG. 10). Comparison of LHR-A with LHR-C reveals that only the third and fourth SCRs of each are highly homologous (99% identical). LHR-A and -D have only 68% overall identity, with maximal identity of 81% between the sixth SCR of each LHR. Thus, completion of the 5' cDNA sequence of CR1 indicates that the F allotype is comprised of 2039 amino acids including a 41 amino acid signal peptide, four LHRs of seven SCRs each, two additional COOH-terminal SCRs, a 25 residue transmembrane region and a 43 amino acid cytoplasmic domain. There are 25 potential N-linked glycosylation sites.

7.3. Discussion

The primary structure of the $NH_2$-terminus and the signal peptide of the F allotype of CR1 has been deduced by the isolation and sequencing of 5' cDNA clones. The highly repetitive nature of the CR1 sequence made critical the development of an appropriate strategy for the preparation and identification of cDNA clones encoding this region of the receptor. A cDNA library was prepared using as a primer a 35-mer oligonucleotide known to hybridize under the conditions of reverse transcription to LHR-B, -C and -D, the possibility was considered that this primer might hybridize also to LHR-A that had been predicted to be highly homologous to LHR-B (see Section 6 supra). Appropriate cDNA clones were identified by the use of another oligonucleotide, KS23.1, that hybridizes only to LHR-B under stringent conditions, thereby increasing the probability of finding 5' cDNA clones. Two clones were found that encompassed almost all of the residual sequence of CR1, and a Sau3AI fragment of one of these, CR1-18, had sequence sufficiently unique to permit its use in the identification of the remaining 5' clones (FIGS. 9, 10).

A 250 bp probe from the 5' region of LHR-A, CR1-18, hybridized not only to CR1 transcripts of 7.9 and 9.2 kb, but also to a 2 kb transcript in human tonsillar RNA under stringent conditions. This cross-hybridizing mRNA was not observed with CR1 cDNA probes from other LHRs or in northern blots of RNA from dimethyl sulfoxide-induced HL-60 cells and HSB-2 T lymphoblastoid cells. Thus, CR1 contains sequences homologous to two additional B cell proteins, one that is encoded by this newly recognized mRNA, and CR2.

8. EXAMPLE:

Expression of Recombinant Human CR1

As described supra, human CR1 cDNA clones have been isolated that span 7.0 kb and contain an open reading frame encoding 2039 amino acids (FIGS. 1A–1D). The proposed precursor form of the receptor includes a 41 amino acid signal peptide, four long homologous repeats (LHRs) of 450 amino acids with each LHR comprised of 7 short consensus repeats (SCRs), two COOH-terminal SCRs of 65 amino acids, a 25 amino acid transmembrane domain, and a 43 amino acid cytoplasmic region. Thus, the CR1 F allotype contains 30 SCRs. The $NH_2$-terminal LHR, LHR-A (see Section 7, supra), is 61% identical to the corresponding region of LHR-B in the first two SCRs and 99% identical in the COOH-terminal five SCRs. Restriction fragments of eight CR1 cDNA clones were spliced to form a full length construct of 6.9 kb and placed downstream of a mouse metallothionein promoter or a cytomegalovirus promoter, and transfected into L (mouse) cells or COS (monkey) cells. Recombinant cell surface CR1 was detected by indirect radioimmunoassay and immunofluorescence. No antigen was detected on cells transfected with the parental vector (CR1$^-$) only. Immunoprecipitation of transfected, surface $^{125}$I-labeled, COS (monkey) cells by anti-CR1 monoclonal antibody, and analysis by non-reducing sodium dodecyl sulfate (SDS) polyacrylamide gel electrophoresis, yielded a 190,000 daltons molecular weight band which co-migrated with the F allotype from human erythrocytes. The expression of recombinant CR1 antigen of the correct molecular weight (Klickstein, L. B., et al., 1988, FASEB J. 2: A1833) provides evidence that the cDNA contains the entire coding sequence of human CR1.

8.1. Construction of Plasimd pBSABCD, Containing the Entire CR1 Coding Sequence We describe herein the construction of plasmid pBSABCD, a vector encoding the full length (SCRs 1–30) CR1 protein.

The 2.3 kb insert from cDNA clone λT8.2 (Klickstein, L. B., et al., 1987, J. Exp. Med. 165: 1095; see Section 6, supra) was subcloned into pUC18 as an EcoRI fragment, such that the 5' end was proximal to the HindIII site in the plasmid polylinker. This plasmid was named p188.2. p188.2 was cut with ApaI and HindIII, and the large 4.7 kb fragment containing CR1 sequence from SCR 26 through the 3' untranslated region plus vector sequences was gelpurified.

The insert from cDNA clone λT50.1 (Klickstein, L. B., et al., 1987, J. Exp. Med. 165: 1095; see Section 6, supra) was subcloned as an EcoRI fragment into M13mp18. This phage was called 18R50.1. DNA from the replicative form of this clone was cut with HindIII and ApaI, and the 1.45 kb fragment containing CR1 SCRs 18–25 was isolated, ligated to the 4.7 kb fragment from p188.2, and the ligation transformed into E. coli DH5α. This plasmid was called p8.250.1.

The 0.75 kb and the 0.93 kb EcoRI fragments from cDNA clone λT8.3 (Wong, W.W., et al., 1985, Proc. Natl. Acad. Sci. U.S.A 22: 7711) were subcloned into plasmid pBR327. These subclones were called pCR1-1 and pCR1-2, respectively, and contained SCRs 11–14 and SCRs 17–21, respectively. The EcoRI inserts were purified from each. The 0.75 kb pCR1-1 fragment was digested with SmaI, and the digest was ligated to pUC18 DNA cut with EcoRI and SmaI. A subclone, p181-1.1, with a 0.5 kb insert corresponding to SCRs 12–14, was isolated. The 0.93 kb fragment of pCR1-2 was digested with HindIII, and ligated to pUC19 cut with EcoRI and HindIII, and a subclone, p191-2.1, was isolated that contained a 0.27 kb insert containing SCR 17.

The cDNA clone λT6.1 (See Section 6, supra; Klickstein, L. B., et al., 1987, J. Exp. Med. 165: 1095; Wong, W. W., et al., 1987, J. Exp. Med. 164: 1531) was digested with EcoRI, and the 0.37 kb fragment corresponding to CR1 SCRs 15 and 16 was subcloned into pBR322. This clone was called pCR1-4. Clone p181-1.1 was cut with EcoRI and ScaI, and the 1.4 kb fragment was isolated. Clone p191-2.1 (Klickstein, L. B., et al., 1987, J. Exp. Med. 165: 1095; see Section 6, supra) was digested with EcoRI and ScaI and the 2.0 kb fragment was isolated, ligated to the 1.4 kb fragment from p181-1.1, and the mixture was transformed into E. coli DH5α. The resulting plasmid was called p1-11-2. Plasmid p1-11-2 was digested with EcoRI, and the 0.37 kb insert fragment from pCR1-4 was inserted by ligation. The resulting plasmid was used to transform E. coli DH5α.

A subclone was chosen that contained a 0.39 kb BamHI-HindIII fragment. This plasmid was called p142 and contained CR1 SCRs 12–17. The 3.5 kb EcoRI-HindIII insert fragment from p8.250.1 was transferred to pGEM3b. This plasmid was called pG8.250.1. The 1.2 HindIII fragment from p142 was purified and ligated to pG8.250.1 that had been cut with HindIII. A subclone was chosen that contained a 2.4 kb PstI-ApaI insert, thus selecting the correct orientation. This plasmid was called pCD and contained CR1 sequences from SCR 12 through the 3' end.

The cDNA clone λ5'7.1 (Klickstein, L. B., et al., September 1987, Complement 4: 180; see Section 7, supra) was cut with PstI, and the 1.35 kb fragment corresponding to SCRs 6–12 was isolated and ligated to PstI-cut pCD. The mixture was transformed, and a subclone was selected which contained 1.35 kb and 1.1 kb HindIII fragments. This clone was called PBCD.

The cDNA clone λ5'3.1 (Klickstein, L. B., et al., 1987, Complement 4: 180; see Section 7, supra) was cut with EcoRI, and the digest was ligated to EcoRI-cut pUC18. A subclone, p3.11-1, was isolated, that contained a 1.0 kb insert corresponding to SCRs 3–7, which insert was gelpurified. The cDNA clone λ5'10.3 (Klickstein, L. B., et al., 1987, Complement 4: 180; see Section 7, supra) was cut with EcoRI, and the 0.63 kb insert containing SCRs 1 and 2 was subcloned into pUC18. This clone was called p10.3.5. Plasmid p10.3.5 was partially digested with EcoRI, and a 3.4 kb fragment corresponding to linear plasmid was isolated and ligated with the 1 kb fragment from p3.11-1. A subclone, pLA, was picked, which contained a 1.3 kb PstI fragment, in the correct site of insertion and orientation.

The cDNA clone λT109.4 (Klickstein, L. B., et al., 1987, Complement 4: 180; see Section 7, supra) was digested with EcoRI, and subcloned into pUC18. A subclone was chosen that contained a 0.55 kb EcoRI fragment corresponding to the 5' untranslated region through the leader sequence and SCRs 1 and 2. The plasmid p109.4 was cut with PstI and BsPMII, and a 3.0 kb fragment containing the vector, leader sequence, and SCR 1, was isolated. The fragment was ligated to a 0.81 kb PstI-BspMII fragment from pLA that contained SCRs 2–5. This new plasmid was called pNLA. The plasmid pNLA was partially digested with EcoRI and completely digested with PstI, and a 1.1 kb EcoRI-PstI fragment containing CR1 sequence from the leader sequence through SCR 5 was isolated and ligated to pBluescript KS+(Stratagene, San Diego, Calif.) to put an XhoI site on the 5' side of the cDNA. This plasmid was called pXLA.

The plasmid pBCD was cut with EcoRV and then partially digested with PstI, and a 6.0 kb PstI-EcoRV fragment containing CR1 sequence from SCR 6 through the 3' untranslated region was isolated and ligated to PstI+SmaI-digested pXLA. The resulting bacterial expression plasmid, which contains the entire CR1 cDNA coding sequence, was called pBSABCD.

Figures 11A, 11B:
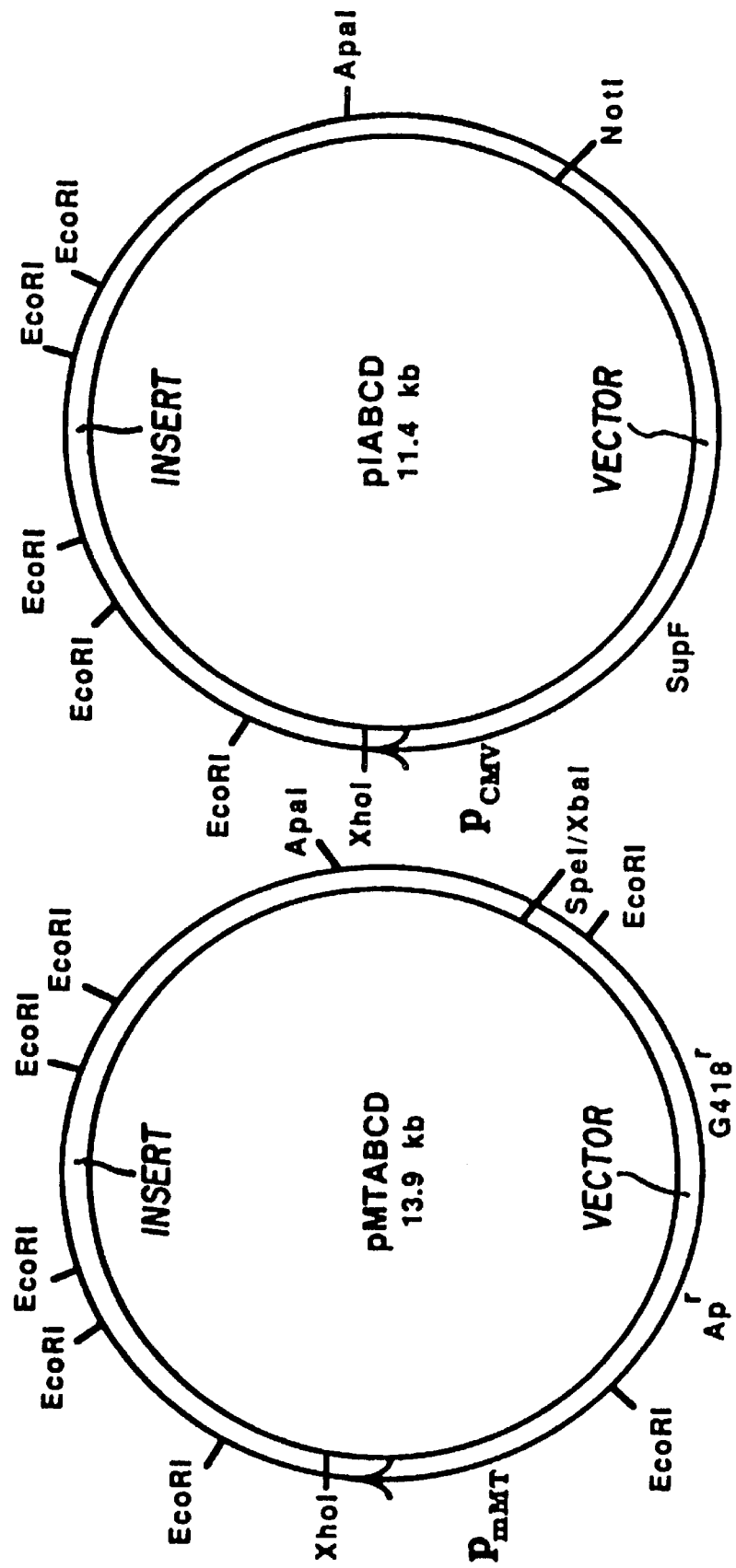
Figure 12A:
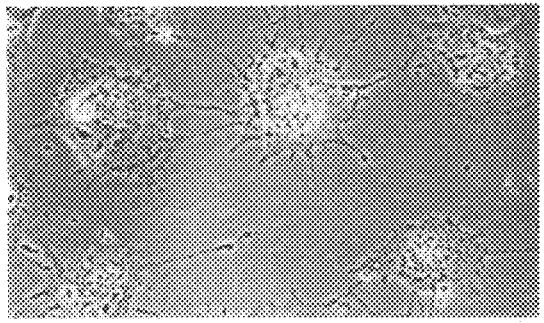
Figure 12B:
Figure 12C:
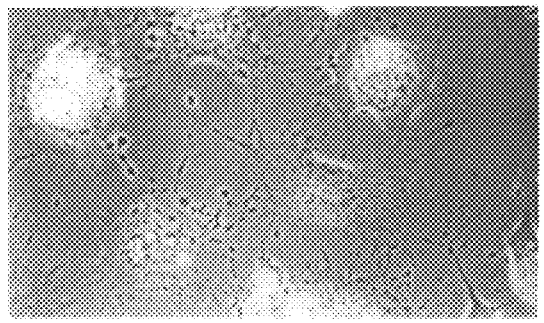
Figure 12D:
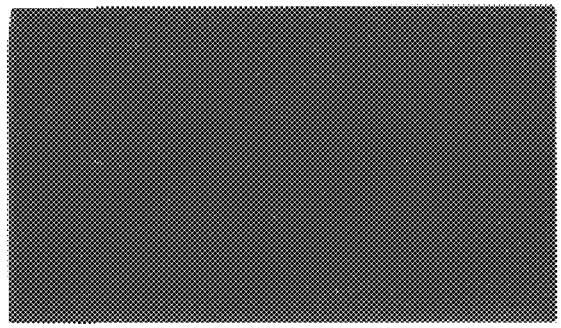
Figure 13A:
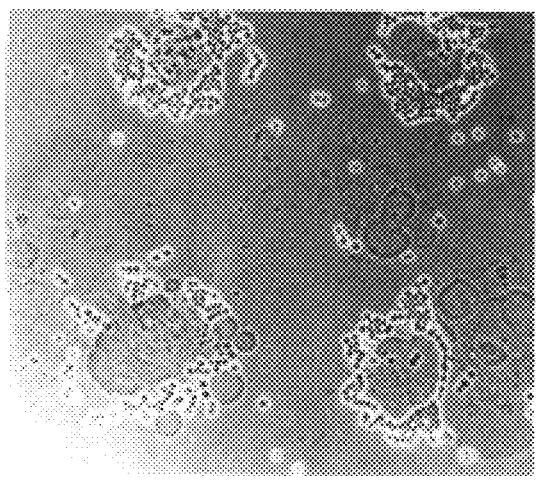
Figure 13B:
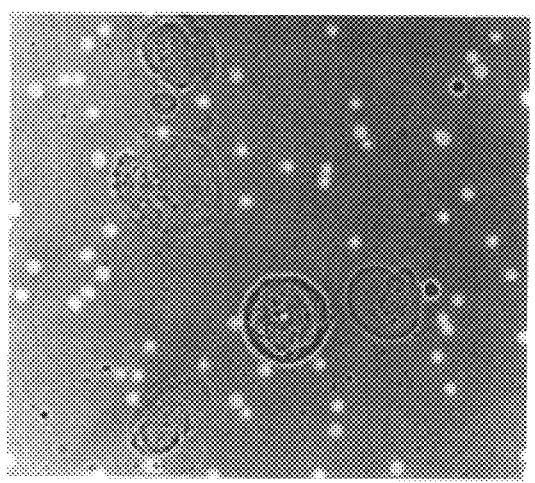
Figure 13C:
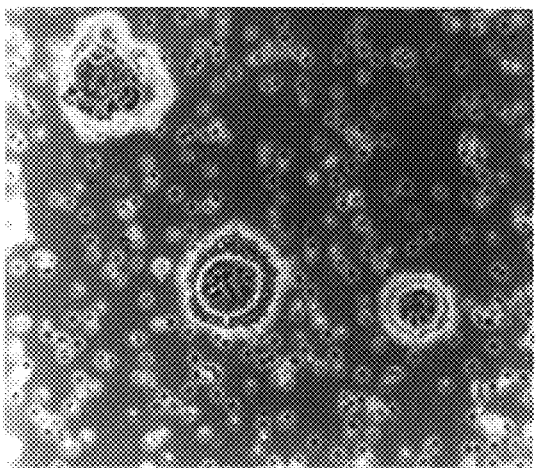
Figure 13D:
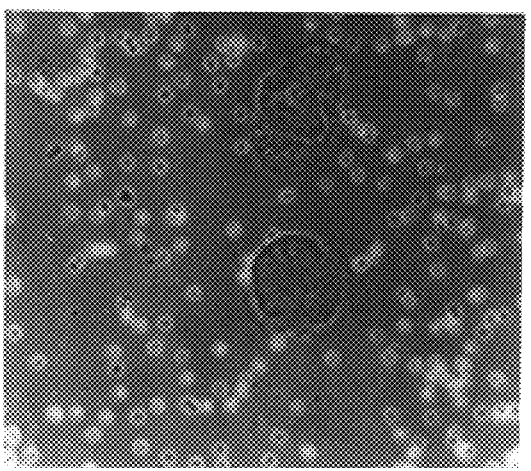

8.2. Construction and Assay of Plasmid piABCD, a Mammalian Expression Vector Containing the Entire CR1 Coding Sequence The pBSABCD plasmid was digested with XhoI and NotI, and the insert was ligated downstream from the CMV promotor in the 4.4 kb fragment of the expression vector, CDM8 (Seed, B., 1987, Nature 329: 840–842), which also had been cut with these restriction enzymes. The resulting construction was termed piABCD (FIG. 11B). Alternatively, the 6.9 kb XhoI-NotI fragment was ligated downstream from the metallothionein promoter in the expression vector, pMT.neo1, which had also been cut with these restriction enzymes. The resulting construction was termed pMTABCD (FIG. 11A).

Sheep erythrocytes sensitized with rabbit antibody (EA) and limited amounts of C4b [EAC4b(lim)] and 12,000 cpm $^{125}$I-C3b per cell [EAcC4b(lim),3b] were prepared by sequential treatment of EAC4b(lim) (Diamedix) with C1, C2 and $^{125}$I-C3 followed by incubation for 60 minutes at 37° C. in gelatin veronal-buffered saline containing 40 mM EDTA. Alternatively, methylamine-treated C3 [C3(ma)] were covalently attached to sheep E (erythrocytes) treated with 3-(2-pyridyldithio) propionic acid N-hydroxysuccinimide ester (Sigma) (Lambris, J. D., et al., 1983, J. Immunol. Methods 65: 277). EAC4b were prepared with purified C4 (Hammer, C. H., et al., 1981, J. Biol. Chem. 256: 3995).

Both piABCD and PMTABCD were transfected by the DEAE (diethylaminoethyl)-dextran method into COS (monkey) cells. Recombinant CR1 was detected on the surface of the transfected cells by immunofluorescence using the anti-CR1 monoclonal antibody, YZ-1; and by immunoprecipitation of $^{125}$I-labeled cells followed by non-reducing SDS-PAGE, which revealed a protein having a mobility identical to that of CR1 immunoprecipitated from human erythrocytes of a donor homozygous for the F allotype (Wong, W. W., et al., 1983, J. Clin. Invest. 72: 685); and by formation of rosettes with sheep erythrocytes coated with C3b (Fearon, D. T., 1980, J. Exp. Med. 152: 20). The identical electrophoretic mobilities of the native and recombinant CR1 proteins confirmed that the CR1 F allotype contains SCRs 1–30.

In addition, murine L cells were co-transfected by the DEAE-dextran method (Ausubel, F. M., et al., 1987, Current Protocols in Molecular Biology, Seidman, J. G. and Struhl, K., eds., John Wiley & Sons, New York; Seed, B., 1987, Nature 329: 840) in duplicate with 0, 2, or 4 μg of either piABCD or pMTABCD and 2 μg of pXGH5, a reporter plasmid that directs the expression of growth hormone (Selden, R. F., et al., 1986, Mol. Cell. Biol. 6: 3173). The cells were harvested after two days and assayed for expression of CR1 by binding of YZ1 monoclonal anti-CR1 antibody. There was a dose response relationship between recombinant plasmid DNA and the expression of CR1 antigen (Table II).

TABLE II

DOSE RESPONSE OF RECOMBINANT CR1 AND HUMAN GROWTH HORMONE IN CO-TRANSFECTED L CELLS

| Plate Number | pXGH5 (μg) | pMTABCD (μg) | piABCD (μg) | YZ1 Anti-CR1 mAB RIA* (cpm) | Growth Hormone (ng/ml) |
|---|---|---|---|---|---|
| 1 | 2 | 0 | 0 | 1444 | 120 |
| 2 | 2 | 0 | 2 | 6058 | 130 |
| 3 | 2 | 0 | 2 | 6531 | 140 |
| 4 | 2 | 0 | 4 | 10620 | 180 |
| 5 | 2 | 0 | 4 | 9898 | 80 |
| 6 | 2 | 2 | 0 | 3111 | 180 |
| 7 | 2 | 2 | 0 | 2747 | 160 |
| 8 | 2 | 4 | 0 | 3547 | 160 |
| 9 | 2 | 4 | 0 | 3337 | 140 |

*For radioimmunoassay (RIA), replicate samples of $3 \times 10^5$ transfected cells in 0.1 ml phosphate-buffered saline containing 1% bovine serum albumin and 0.02% sodium azide were incubated at 0° C. for 60 minutes with 3 μg/ml YZ-1 IgG1 anti-CR1 (Changelian, P. S., et al., 1985, J. Immunol. 134:1851). The cells were washed and resuspended in 0.1 ml of buffer containing 1–2 μCi/ml of $^{125}$I-F(ab')$_2$ goat-anti-mouse IgG or $^{125}$I-protein A. After 1–2 hours at 0° C., the cells were washed and assayed for $^{125}$I.

The plasmid, piABCD, directed the expression of nearly three-fold more CR1 antigen than did pMTABCD. The growth hormone concentration in the culture medium varied by less than two-fold with the exception of plate 5. Additional experiments revealed that piABCD directed the transient expression of three-fold more CR1 antigen in COS cells than in L cells.

CR1 antigen was present in clusters on the surface of the transfected COS cells when assessed by indirect immunofluorescence of cells stained with YZ1 anti-CR1 mAB (FIGS. 12a–12d). This distribution of recombinant CR1 on COS cells resembles that of wild type CR1 on human leukocytes (Fearon et al., 1981, J. Exp. Med. 153: 1615).

The molecular weight of the recombinant CR1 was determined by surface iodination of COS cells transfected with piABCD, immunoprecipitation of cell lysates with Sepharose-YZ1, SDS-PAGE and autoradiography. The recombinant CR1 had a molecular weight of 190,000 unreduced which is equivalent to that of the F allotype and less than that of the S allotype of erythrocyte CR1 (FIG. 14).

The C3b-binding and C4b-binding function of recombinant CR1 was assayed by the formation of rosettes between the transfected COS cells and EAC4b or EAC4b(lim),3b. In 31 separate transfections, 5%–50% of COS cells transfected with the plasmid, piABCD, bound five or more EAC4b or EAC4b(lim),3b (FIG. 13a–13d). The COS cells expressing CR1 did not form rosettes with EAC4b(lim),3bi, although this intermediate did form rosettes with Raji B lymphoblastoid cells expressing CR2.

8.3. Expression of CR1 Fragments

Expression vectors encoding part of the CR1 coding sequence (deletion mutants) were constructed as described infra, and found to express their respective CR1 inserts when transformed into COS cells. The CR1 fragments were expressed as cell-surface proteins.

8.3.1. Construction of Deletion Mutants piBCD, piABD, piACD, piAD, piBD, piCD and piD The construction of these deletion mutants was performed by taking advantage of the presence of a single BsmI site in a homologous position near the amino-terminus of each of the four CR1 long homologous repeats (LHRs), and the absence of BsmI sites elsewhere in the CR1 cDNA and Bluescript vector (Stratagene, San Diego, Calif.).

Ten micrograms of the plasmid pBSABCD were partially digested with 50 units of the restriction enzyme BsmI for 45 minutes, and the digest was fractionated by agarose gel electrophoresis. DNA fragments of 8.55 kb, 7.20 kb and 5.85 kb were purified that corresponded to linear segments of the parent plasmid that lacked one, two or three LHRs, respectively. Each of the three fragments was ligated to itself and the ligations used separately to transform competent E. coli DH5α to ampicillin resistance.

The 8.55 kb fragment was generated as the consequence of cleavage of PBSABCD at two adjacent BsmI sites, thus there are three possible product plasmids after ligation, pBCD, pACD or pABD, where the capital letters represent the LHRs that remain in the plasmid. These were distinguishable by restriction mapping with SmaI. DNA was prepared from 12 colonies, digested with SmaI, and separated by agarose gel electrophoresis. Five clones had two SmaI fragments of 2.5 kb and 6.1 kb, corresponding to deletion of the coding sequence of LHR-A, thus representing PBCD. Three clones had a single linear fragment of 8.5 kb corresponding to pACD. Four clones had two SmaI fragments of 1.2 kb and 7.4 kb, which was expected for the deletion of the coding sequence of LHR-C, producing PABD. The 5.6 kb insert of each of these three constructions was gel-purified after double digestion with XhoI and NotI, and ligated to the expression vector CDM8 that had been gel-purified after digestion with the same restriction enzymes. E. coli DK1/P3 was transformed with the ligation mixtures and DNA was prepared from five colonies of each. The presence of the deleted CR1 cDNA insert in the expression vector was shown in each case by SacI digestion, which revealed the expected two fragments of 4.20 kb and 5.75 kb. These plasmids were called piBCD, piACD and piABD.

The 7.20 kb fragment from the partial digestion of pBSABCD was a consequence of BsmI digestion at three adjacent sites or, equivalently with respect to the large fragment, at two sites with a single uncut site between them, thus there were two possible products obtainable after transformation, pAD and pCD. These were distinguished by double digestion with XhoI and PstI, which yielded two fragments of 1.0 kb and 6.2 kb in the case of pAD, and a linear fragment of 7.2 kb for pCD. The 4.2 kb insert from each of these plasmids was gel-purified after double digestion with XhoI and NotI, and subcloned into CDM8 as above. The presence of the deleted CR1 cDNA in the expression vector was shown by double digestion with PstI and BglII. The clone piAD had fragments of 2.4 kb and 6.2 kb, while piCD had a single fragment of 8.6 kb.

The 5.85 kb fragment from the BsmI digestion of pBSABCD represents a product of complete digestion and a single clone, pD, was obtained after transformation of E. coli DH5α. This was confirmed by double digestion with HindIII and BglII which yielded the expected 3.7 kb and 2.2 kb fragments. The 2.9 kb insert of the clone was gel-purified after double digestion with XhoI and NotI and ligated to the expression vector as above. HindIII digestion of the resulting piD clone yielded the expected 7.3 kb fragment, a XhoI+BglII double digest gave 2.2 kb and 5.1 kb fragments, and a SacI digest resulted in the expected 1.5 kb and 5.8 kb fragments.

The plasmid pBD was prepared by BsmI partial digestion of pBCD. The linear 7.2 kb fragment corresponding to cleavage of two adjacent BsmI sites was gel-purified, self-ligated as above, and E. coli DH5α was transformed to ampicillin resistance. pBD was identified by the presence of 1.2 kb and 6.0 kb fragments upon SmaI digestion. The 4.2 kb insert was purified after double digestion with XhoI and NotI, and transferred to CDM8 as above. The clone piBD was confirmed by observation of the expected 0.8 kb and 7.8 kb fragments after HindIII digestion.

COS cells transiently expressing the piABCD, piBCD, piCD, and piD constructs, respectively, were surface-labelled with $^{125}I$, and immunoprecipitated with anti-CR1 antibody. On SDS-PAGE following reduction, the product of the piABCD construct comigrated with the F allotype of CR1, while the deletion mutants demonstrated stepwise decrements of approximately 45,000 daltons, indicative of the deletion of one, two and three LHRS, respectively (FIG. 17).

8.3.2. Construction of Deletion Mutants piP1, piE1, piE2, piE-2, piU1, piU-2 and piA/D The plasmid piABCD was completely digested with BstEII and the two fragments at 1.35 kb (a doublet) and 8.6 kb were gel-purified, mixed, and ligated, and E. coli DK1/P3 was transformed to ampicillin and tetracycline resistance. Colonies were screened by hybridization with the CR1 cDNA probe CR1-4 (see Section 8.1, supra), and strongly positive clones were picked and further screened by digestion with SmaI. piE1 was identified by the presence of two fragments at 2.7 kb and 7.3 kb, and piE2 was identified by a single 10.0 kb linear fragment. piE-2 was identified as a weakly CR1-4 positive clone that contained a single 8.6 kb SmaI fragment.

The plasmid piP1 was obtained by complete digestion of piABCD with PstI and gel-purification of the large, 10.0 kb fragment. This fragment was ligated and E. coli DK1/P3 was transformed with the mixture. The resulting plasmid, piP1, contained a single, 10.0 kb SmaI fragment.

The plasmids piU1 and piU-2 were prepared by first transforming the dcm⁻ strain GM271/P3 with the plasmid PXLA, and isolating DNA. This DNA was double digested with StuI and NotI, and the 3.3 kb fragment was gel-purified. The plasmid pBSABCD was partially digested with NsiI, and the resulting four base pair 3' overhangs were removed by treatment with the Klenow fragment of E. coli DNA polymerase I. The DNA was then digested to completion with NotI, and fragments of 5.4 kb and 4.0 kb were gel-purified. These were ligated to the 3.3 kb StuI-NotI fragment from PXLA, and the ligation mixture was used to transform E. coli DH5α to ampicillin resistance. Colonies were screened by hybridization to the CR1 cDNA probe CR1-4, and positive clones were further checked by restriction digestion with HindIII which yielded three fragments of 0.8 kb, 1.3 kb and 6.5 kb for pU1, and two fragments of 0.8 kb and 6.5 kb for pU-2. The StuI-blunted NsiI splice was confirmed to be inframe by DNA sequencing of these plasmids. The inserts of pU1 and pU-2, 5.6 kb and 4.2 kb, respectively, were gelpurified after XhoI and NotI double digestion, and were ligated to the expression vector CDM8 as described supra. The structures of the clones, piU1 and piU-2, were confirmed by restriction digestion with XhoI+PstI, yielding the expected two fragments of 1.2 kb and 8.8 kb for piu1 and a linear 8.7 kb fragment for piU-2.

The plasmid piA/D was prepared by first digesting piA-BCD with PstI to completion. The PstI digest was then partially digested with ApaI, and the 3' overhangs were removed with the Klenow fragment of E. coli DNA polymerase I. The DNA was then fractionated by agarose gel electrophoresis and the 7.5 kb fragment was isolated, ligated, and used to transform E. coli DK1/P3 to ampicillin and tetracycline resistance. The construction was confirmed by double digestion with KpnI+SacI, which yielded the expected four fragments of 0.8 kb, 1.5 kb, 1.7 kb and 3.3 kb.

9. EXAMPLE:

Identification of C3b and C4b Binding Domains

9.1. ASSAYS and RESULTS

Plasmids piABCD, piAD, piCD, and piD, containing the LHR(s) denoted by the capital letter(s) of their names, were transformed into COS cells, which were used in assays to assess the ability of their encoded CR1 fragments to bind C3b or C4b. Binding assays were carried out by observation of erythrocyte resetting resulting from the binding of C3b or C4b-coated red cells by COS cells expressing a full-length CR1 molecule or a CR1 deletion mutant on their cell surface (transient expression). Transfected cells, $1-4\times10^6$/ml, were incubated with C3- or C4-bearing erythrocytes, $2-6\times10^8$/ml, in 0.02 ml for 60 minutes at 20° C. The percentage of transfected cells forming rosettes was evaluated microscopically with a transfected cell scored as a rosette if there were at least five adherent erythrocytes. The results are shown in Table III.

TABLE III

FORMATION OF ROSETTES BETWEEN COS CELL TRANSFECTANTS EXPRESSING RECOMBINANT FORMS OF CR1 AND SHEEP ERYTHROCYTES BEARING C3(ma) OR C4(ma)

| COS Cell Transfectant | % Transfectants Forming Rosettes | |
|---|---|---|
| | % Transfectants Fluorescent with Anti-CR1 | |
| | EC3(ma)* | EC4(ma)# |
| piABCD | 109 (3)^π | 62 (2) |
| piAD | 8 (3) | 107 (2) |
| piBD | 107 (3) | 12 (2) |
| piCD | 127 (3) | 32 (2) |
| piD | 0 (3) | 0 (2) |
| piA/D | 11 (2) | 83 (2) |
| piE-2 | 1 (1) | 102 (1) |

*The numbers of C3(ma) per erythrocyte were 60,000, 350,000 and 900,000, respectively, in the three experiments using this intermediate.
The number of C4(ma) per erythrocyte were 160,000 and 140,000, respectively, in the two experiments using this intermediate.
πNumber of experiments.

In each of three separate experiments, the proportion of COS cells expressing the full length piABCD construct that formed rosettes with the EC3(ma) was similar to the fraction having detectable recombinant receptor, as assessed by immunofluorescence using either YZ1 monoclonal anti-CR1 antibody or rabbit anti-CR1 antiserum (Table III). In contrast, cells expressing piD did not form rosettes, indicating that a C3-binding site(s) must reside in or require the presence of LHR-A, -B or -C. A site was shown to be present in both LHR-B and -C by demonstrating that cells expressing either the piBD or piCD constructs formed rosettes with EC3(ma). Cells expressing piAD, piA/D, or piE-2 did not have equivalent C3-binding function. As the piE-2 construct differs from piCD only in having SCR-1 and -2 of LHR-A instead of the first two SCRs of LMR-C, the function of the C3-binding site in LHR-C must require these $NH_2$-terminal SCRS.

The proportion of COS cells expressing the full length piABCD recombinant that formed rosettes with EC4(ma) was less than the fraction rosetting with EC3(ma), perhaps reflecting fewer C4(ma) per erythrocyte (Table III) or fewer C4-binding sites per receptor. Deletion mutants having all or part of LHR-A, the piAD, piA/D and piE-2 constructs, bound EC4(ma) better than did the deletion mutants, piBD and piCD; piD lacked this function. Thus, the C4-binding site of CR1 resides primarily in LHR-A, although secondary sites may be present in LHR-B and -C. The improved rosetting capability of the piE-2 construct relative to that of piCD suggests that SCR-1 and -2 of LHR-A are involved in the C4 binding site.

Radioimmunoassay of the binding of YZ1 monoclonal anti-CR1 antibody indicated significant uptake by COS cells expressing the piABCD, piAD, piBD, and piCD constructs (Table IV). Cells transfected with piD or piA/D, which is comprised of the five $NH_2$-terminal SCRs of LHR-A and the three COOH-terminal SCRs of LHR-D, did not bind YZ1 anti-CR1 antibody, although the products of these constructs bound polyclonal anti-CR1 antiserum (Table IV). Thus, the YZ1 epitope is repeated in LHR-A, -B and -C, is not present in the $NH_2$-terminal SCRs of LHR-A, and is not present or is inaccessible in LHR-D.

TABLE IV

BINDING OF MONOCLONAL AND POLYCLONAL ANTI-CR1
ANTIBODY TO COS CELL TRANSFECTANTS EXPRESSING
RECOMBINANT FORMS OF CR1

| COS Cell Transfectant | Bound YZ1 Monoclonal Antibody* | Bound Rabbit Polyclonal Antibody* |
|---|---|---|
| piABCD | 2362 | 12277 |
| piAD | 2879 | 19891 |
| piBD | 3646 | 21922 |
| piCD | 2189 | 19926 |
| piA/D | 410 | 23052 |
| piD | 404 | 16386 |
| CDM8 | 428 | 4886 |

*Replicate samples of $3 \times 10^5$ transfected cells in 0.1 ml phosphate-buffered saline containing 1% bovine serum albumin and 0.02% sodium azide were incubated at 0° C. for 60 minutes with 3 µg/ml YZ1 IgG1 anti-CR1 mAb (Changelian, P. S., et al., 1985, J. Immunol. 134:1851) or with 90 µg/ml rabbit IgG anti-CR1 antibody. The cells were washed and resuspended in 0.1 ml of buffer containing 1–2 µCi/ml of $^{125}$I-F(ab')$_2$ goat-anti-mouse IgG or $^{125}$I-protein A. After 1–2 hours at 0° C., the cells were washed and assayed for $^{125}$I. Values shown are the mean of duplicate determinations, cpm per $3 \times 10^5$ COS cells.

9.2. Discussion

The conserved BsmI site found midway through the coding sequence of the first SCR in each LHR permitted the construction of a series of deletion mutants that corresponded closely to the boundaries of the LHRs, and maintained the open reading frame and the appropriate positions of the four cysteines necessary for the presumed disulfide bond formation (FIG. 16). Comparison of the C3(ma)- and C4(ma)-binding functions of these deletion mutants distinguished not only the LHRs having these specificities, but also those SCRs critical for determining the ligand specificity. Thus, the capacity of piAD, piA/D, and piE-2 forms of the receptor, but not the piD form, to mediate rosette formation between the transfected COS cells and EC4(ma) indicated that the $NH_2$-terminal two SCRs of LHR-A contained a site for interaction with this complement protein (Table III). This site was only relatively specific for C4(ma) because transfectants expressing piAD and piA/D also were capable of binding EC3(ma) (Table III). The C3(ma)-binding function of the receptors encoded by the piBD and piCD constructs, demonstrated by rosette assay and factor I-cofactor function for cleavage of C3(ma) (Table III; FIG. 18), indicated the presence of sites specific for C3(ma) in the first two SCRs of these LHRs. These sites also were capable of interacting with C4(ma) (Table III). Thus, there are preferential, but overlapping, C4- and C3-binding activities in LHR-A, -B and -C.

Alternatively, the capacity of the COS cells expressing the piBD and piCD constructs to bind EC4(ma) may have been caused by the transfer of nucleotides encoding the $NH_2$-terminal 36 amino acids from SCR-1 of LHR-A to LHR-B and -C through the ligation of the BsmI fragments. However, these 36 amino acids alone did not confer on the piD product C4-rosetting function. We cannot exclude a secondary function of LHR-D in these reactions because this LHR was present in all the constructs assayed for function. The finding of three distinct ligand recognition sites in CR1, two for C3b and one for C4b (FIG. 19), indicates that each receptor molecule may be capable of effectively binding complexes bearing multiple C4b and C3b molecules despite having a relatively low affinity for monovalent ligands (Arnaout, M. A., et al., 1983, Immunology 48: 229). This finding also provides an explanation for the inability of soluble C4b to inhibit formation of rosettes between erythrocytes bearing C3b and a human B lymphoblastoid cell line (Gaither, T. A., et al., 1983, J. Immunol. 131: 899). Possible ligands for which CR1 would be especially adapted may be the molecular complexes, C4b/C3b and C3b/C3b, that are generated during activation of the classical and alternative pathways, respectively. Since there are distinct binding sites in three of the four LHRs, the CR1 structural allotypes differing by their number of LHRs may have significant functional differences caused by variations in the number of ligand binding sites. Although in vitro studies have not reported differing binding activities of the F, S and F' (A, B and C, respectively) allotypes, the smaller F' allotype presumably having only three LHRs might have an impaired capability to clear immune complexes. The F' allotype has been reported possibly to be associated with systemic lupus erythematosus (van Dyne, S., et al., 1987, Clin. Exp. Immunol. 68: 570).

10. EXAMPLE

Demonstration of Factor I Cofactor Activity

The recombinant CR1 protein, and specific fragments thereof, in both cell-surface and solubilized forms, were demonstrated to have C3b factor I cofactor activity.

Assays of factor I cofactor activity were carried out by modifications of a published procedure (Fearon, D. T., 1979, Proc. Natl. Acad. Sci. U.S.A. 76: 5867).

For assay of factor I cofactor activity of solubilized CR1 and fragments, cell-surface CR1 protein and fragments were solubilized with Nonidet P-40, and the lysate was immunoprecipitated with anti-CR1 monoclonal antibody YZ-1 coupled to Sepharose beads. Detergent lysates of $1 \times 10^6$ transfected COS cells were immunoprecipitated sequentially with Sepharose UPC10 anti-levan and Sepharose-YZ-1. The immunoprecipitate was then assayed for factor I cofactor activity by incubation of the washed beads for 60 minutes at 37° C. with 0.5 μg of $^{125}$I-C3(ma) and 200 ng of factor I in 0.05 ml PBS, 0.5% NP-40. After incubation, the supernatant containing radiolabeled C3(ma) was analyzed by SDS-polyacrylamide gel electrophoresis and autoradiography. Factor I cofactor activity was indicated by the appearance on the autoradiogram of lower molecular weight forms of the alpha chain of C3(ma) resulting from proteolytic cleavage by factor I.

For assay of factor I cofactor activity of cell-surface CR1 and fragments, transfected COS cells carrying a CR1 expression vector (piABCD, piAD, piBD, piCD, or piD, described supra) were incubated with 0.5 μg $^{125}$I-C3(ma) and 0.2 μg factor I (Fearon, D. T., 1977, J. Immunol. 119: 1248), and analyzed as described supra.

The factor I-cofactor activity of cell-surface recombinant CR1 is shown in FIG. 15. Factor I cleaved the alpha chain of C3(ma) into fragments of molecular weights 76,000 and 46,000 only in the presence of immunoimmobilized, recombinant CR1 or factor H (FIG. 15). The regions corresponding to bands from the autoradiogram were excised from the gel and assayed for $^{125}$I to determine the amount of alpha chain cleaved. In the presence of factor H, 91% of the alpha chain was cleaved while in the presence of increasing amounts of recombinant CR1, 26%, 41%, and 55%, respectively, was cleaved. Although the COS cells transfected with the CDM8 vector alone contained some endogenous factor I-cofactor activity, an increase in this function was evident with COS cells transfected with piABCD, piBD and piCD (FIG. 18). No enhanced cleavage of $^{125}$I-C3(ma) was seen with COS cells transfected with piAD or piD. Thus, among these constructs, only the deletion mutants, piBD and piCD, that conferred on COS cells a capacity for binding C3, also had factor I-cofactor activity for cleavage of C3.

The results of the assays for factor I cofactor activity with both cell-surface and solubilized forms of CR1 and fragments thereof are shown in Table V.

TABLE V

FACTOR I COFACTOR ACTIVITY OF CELL-SURFACE AND SOLUBILIZED FORMS OF CR1 and CR1 FRAGMENTS

| | Factor I Cofactor Activity[b] | |
|---|---|---|
| Plasmid[a] | Cell-Surface | Solubilized |
| piABCD | + | + |
| piAD | − | − |
| piBD | + | ND[c] |
| piCD | + | + |
| piD | − | ND[d] |

[a]Encoding the assayed CR1 protein or fragment, and transfected into COS cells for expression.
[b](+) denotes an increase in cofactor activity above the endogenous level observed upon transfection with the CDM8 vector alone.
[c]Not determined.
[d]Not determined, due to the absence from LHR-D of the epitope recognized by anti-CR1 monoclonal antibody YZ-1.

As shown in Table V, expression of piABCD (encoding a full-length CR1 protein), piBD (encoding LHR-B and -D) or piCD (encoding LHR-C and -D) produced a CR1 product with C3b factor I cofactor activity. The data of Table V thus provide evidence that the CR1 protein or a fragment thereof can promote complement inactivation.

11. EXAMPLE

Expression of Recombinant Soluble CR1

The CR1 cDNA was modified by recombinant DNA procedures so that a soluble form (sCR1) of CR1 or CR1 fragments was produced. The sCR1 constructs were expressed in a mammalian system where the expressed protein was secreted from the cells. Large quantities of the soluble polypeptides were produced, which, in contrast to the membrane bound form of CR1 proteins, did not have to be solubilized to obtain them in solution.

11.1. Materials and Methods

11.1.1. Enzyme Digestions

All restriction enzyme digestions, linker ligations, and T4 DNA ligase and E. coli DNA polymerase reactions were done according to the manufacturer's (New England Biolabs, Inc., Beverley, Mass.) reccolindations. E. coli DH1 or DH5α were made competent by the procedure of Morrison, D. A., 1979, Meth. Enzymol 68: 326–331. Competent bacterial cells were transformed with DNA according to Maniatis, T., et al., 1982, Molecular Cloning, A Laboratory Manual, Cold Spring Harbor Laboratory, Cold Spring Harbor, N.Y. Plasmids were purified by alkaline lysis or by the boiling method (Maniatis, T., et al., supra).

11.1.2. DNA Fragment Isolations

DNA fragments were purified from agarose (BioRad, Richmond, Calif.) gels as follows. The appropriate DNA band was excised from the gel using a blade, and the agarose slice was placed on a piece of parafilm, sliced into very small pieces, and transferred to a new piece of parafilm. The agarose pieces were crushed, and the agarose transferred to a 1.5 ml tube. An equal volume of phenol (Ultra pure, BRL, Gaithersburg, Md.) was added, the mixture vortexed, then frozen at −70° C. for 10 minutes, and centrifuged for 10 minutes. The aqueous phase was further extracted twice with phenol/chloroform (1:1), and twice with chloroform. The DNA was then ethanol precipitated, the pellet washed, dried in vacuo, and resuspended in 10 mM Tris-HCl, pH 7.0, 1 mM EDTA.

DNA fragments were isolated from low gelling temperature agarose (FMC, Corp., Rockland, Me.) as follows. The appropriate DNA band was excised from the agarose gel, placed in a 1.5 ml tube, and melted a 65° C. for 15 minutes. The liquified gel was extracted with phenol containing 0.1% sodium dodecyl sulfate (SDS, ultra pure, BRL, Gaithersburg, Md.). The aqueous phase was further extracted once with phenol-SDS and twice with chloroform. The DNA was then ethanol precipitated in 2.0M NH$_4$Acetate, dried, and resuspended in water.

11.1.3. Transfection into Mammalian Cells

Transfection of DNAs into mammalian cells was performed by the CaPO$_4$ precipitation and glycerol shock procedure of Graham and van der Eb (1973, Virology 52: 456–467). DUX B11 CHO cells, after being incubated with the DNA-calcium phosphate preparation for 4 to 6 hours, were subjected to glycerol shock by removing the growth medium by aspiration and adding 5 ml of 20% glycerol DMEM medium for 1 minute. Cells were then washed twice in complete alpha MEM and incubated in this medium for 48 hours.

11.1.4. CHO Transfectant Cell Culture

DUX B11 CHO cell transfectants were grown in DHFR (dihydrofolate reductase) selection medium consisting of alpha MEM medium (Gibco) without nucleosides, supplemented with 10% dialyzed fetal calf serum (Gibco) and 4 mM L-glutamine. Amplification was carried out by growing cells in increasing concentrations of methotrexate (Sigma, #A-6770, Amethopterin) (Kaufman, R. J., et al., 1985, Molec. Cell Biol. 5: 1750–1759).

11.1.5. Elisa for the Detection of Soluble CR1 Levels

11.1.5.1. CR1 Standards

Detergent lysates of hemoglobin-free red blood cell (RBC) ghosts were used as a CR1 standard in the ELISA (enzyme-linked immunosorbent assay). The ghosts were prepared as previously described (Wong, W. W. and Fearon D. T., 1987, Meth. Enzymol 150: 579–585). Briefly, expired whole blood was obtained from the Red Cross. The red cells were washed three times in PBS, then lysed in 6 volumes of hypotonic lysis buffer (10 mM Tris pH 8, 0.1 mM PMSF (phenyl methyl sulfonyl fluoride), 0.1 mM TPCK (tosylamide-phenylethyl chloromethyl ketone), aprotonin, 2 mM EDTA). The ghosts were washed several times in lysis buffer, counted in a hemocytometer, aliquoted and frozen at −70° C. until needed. For the CR1 ELISA, ghosts were diluted to $1.6 \times 10^8$ ghosts/ml in solubilizing buffer (10 mM Tris pH 8, 50 mM KCl, 0.2% NP40, 0.3% DOC, 6.2 mM PMSF, 0.2 mM iodacetamide, aprotonin, 0.1 mM TPCK, 2 mM EDTA, 0.2% NaN3) and serially diluted to $2.5 \times 10^6$ ghosts/mil for use as standards in the ELISA. Absorbances at 490 nm were plotted and any unknown sample run was referred to the plot to obtain ghost equivalents/ml. 11.1.5.2. CR1 Elisa Immulon-II plates were coated with 100 μl/well of a 0.4 μg/ml concentration of an anti-CR1 monoclonal antibody (clone J3D3, AMAC IOT 17) (Cook, J., et al., 1985, Molec. Immunol. 22: 531–538) in PBS and incubated overnight at 4° C. The antibody solution was then discarded and the plates were blocked by the addition of blocking buffer (1.0% BSA in PBS) at 300 μl/well and incubation at 37° C. for 2 hours. After blocking, plates were used immediately or stored at 4° C. until needed.

Plates were washed three times using PBS containing 0.05% Tween-20. Samples were added at 100 μl/well in duplicate and incubated 2 hours at 37° C. If necessary, samples were diluted in solubilizing buffer. Standard RBC ghosts were included on each plate. After sample incubation, plates were washed three times and a conjugate (Wilson, M. B. and NaKane, P. K., 1978, Immunofluorescence and Related Staining Techniques, North Holland Biomedical Press, pp. 215–224) of horseradish peroxidase (HRP) and the monoclonal antibody YZ1 (Changelian, P. S., et al., 1985, J. Immunol 184: 1851–1858) was diluted 1: 8000 in 50% FCS, 50% blocking buffer and added at 100 μl/well. After incubating for two hours at 37° C., the plates were again washed three times with PBS containing 0.05% Tween-20. The substrate orthophenylenediamine (OPD) was added at 0.2% concentration in substrate buffer (0.36% citric acid $H_2O$, 1.74% $Na_2HPO_4 \cdot 7H_2O$, 0.1% thimerosal, 0.4% $H_2O_2$, pH 6.3) at 100 μl/well. The reaction was stopped after 20 minutes at room temperature using 50 μl/well of 2N $H_2SO_4$. Absorbances at 490 nm were read.

11.2. Genetic Modifications of CR1 Coding Sequences

CR1 cDNA is composed of approximately 6,951 nucleotide base pairs FIGS. 1A–1P, Sections 6, 7, supra). The translational stop signal of the native cDNA is located at base pair 6145. The protein is a membrane-bound receptor molecule composed of four long homologous repeats (LHRs) which are exposed on the exterior surface of the cell membrane, plus a membrane-spanning domain of approximately 25 amino acids, followed by a carboxyl terminal region extending into the cytoplasm. This cytoplasmic domain consists of forty-three amino acids. The strategy we used to produce soluble CR1 molecules (sCR1 ) was to remove the transmembrane region that anchors a protein in the cell membrane and then to express the truncated constructs as secreted polypeptides.

11.2.1. Construction of pBSCR1c

Plasmid pBSABCD (Example 8, supra) contains the CR1 cDNA from nucleotides 1 to 6860 and lacks the untranslated sequences 3' to the EcoRV site at nucleotide 6860. CR1 cDNA possesses a unique BalI restriction endonuclease recognition site at base pair 5914, twenty-nine base pairs away from the start of the transmembrane domain. pBSABCD was first digested with BalI to produce a linear molecule with flush ends and was then ligated using T4 DNA ligase to a synthetic oligonucleotide consisting of two 38 nucleotide complementary strands with the following sequence:

5': CCAAATGTACCTCTCGTGCACATGATGCT taaCTCGAG

3': GGTTTACATGGAGAGCACGTGTACTAC-GAATTGAGCTC

The resulting molecule had a restored BalI site and an altered sequence which reproduced the native CR1 sequence up to and including the alanine residue at the start of the transmembrane domain. In addition, a translational stop signal (in lower case and underlined above) had been introduced immediately after the alanine, followed by an XhoI restriction site to faciliate subcloning the altered cDNA.

XhoI digestion of this plasmid (designated pBSCR1c) excised the cDNA insert (designated sCR1c) by cutting at the oligonucleotide-added XhoI site in the cDNA and at the XhoI site in the pBSKS+• multiple cloning site at the 5' end of the CR1 cDNA. pBSCR1c contains the following C-terminal sequences: Base No. 5911: CTGGCCAAATG-TACCTCTCGTGCACATGATGCTTAACTCGAG Amino Acids: LAKCTSRAHDA END XhoI site

11.2.2. Construction of pBSCR1s

A second sCR1 construct lacking a transmembrane region was generated as follows. pBSABCD was digested with SacI which cut at the unique SacI site at nucleotide base pair 5485 in the CR1 cDNA and at the SacI site in the multiple cloning site of the host plasmid, located at the 3' end of the CR1 cDNA. This digestion resulted in the excision of 1375 nucleotides of DNA sequence from the 3' end of the cDNA. This fragment was then removed electrophoretically. The exposed ends of the resulting plasmid, containing the remaining sCR1 cDNA, were made flush using T4 DNA polymerase and a blunt-end ligation was performed. The Pharmacia univeral translation terminator (catalog #27-4890-01, Pharmacia, Inc., Piscataway, N.J.), a self-complementary oligomer which contains translational stop signals in all three reading frames, was also included in the ligation. Upon ligation, the inserted oligomer provided a new translation stop signal for the sCR1 cDNA.

11.2.3. Construction of pBM-CR1c pBMT3X is a eukaryotic expression vector (Krystal, M., et al., 1986, Proc. Natl. Acad. Sci. USA 83: 2709–2713) that contains the human metallothionein—1A gene, which confers to cells resistance to increased levels of heavy metals such as cadmium. The vector also contains the mouse metallothionein-1 gene that contains an engineered XhoI site preceding the initiation codon for the Mt-1 protein. The XhoI site is used as the insertion site for expression of genes under the control of the mouse Mt-I promoter.

sCR1c insert (approximately 5.9 kb) was excised from pBSCR1c using XhoI and then ligated to the unique XhoI site of vector pBMT3X. The correct orientation of the sCR1c insert in pBMT3X was determined by restriction digestion (Maniatis, T., et al., 1982, Molecular Cloning, A Laboratory Manual, Cold Spring Harbor Laboratory, Cold Spring Harbor, N.Y.). The resulting plasmid was named pBM-CR1c.

11.2.4. Construction of Deletion Mutants pT-CR1c1, pT-CR1c2, pT-CR1c3 pT-CR1c4, and pT-CR1c5

Various deletion mutants were also constructed that specifically deleted portions of the sCR1 cDNA (FIG. 20). Each deletion mutant lacked the transmembrane region of the full length cDNA so that expression of the mutants would yield soluble polypeptides.

11.2.4.1. pT-CR1c1 pBSCR1c was digested with SmaI, resulting in two fragments of size 2.56 kb and 7.3 kb. These fragments were separated by agarose gel electrophoresis, and the 7.3 kb fragment was purified and religated to itself. *E. coli* DH5α cells were made competent (Morrison, D. A., 1979, Meth. Enzymol. 68: 326–331) and then transformed with the ligation mix. The resulting plasmid was named pBL-CR1c1. This construct removed 38% of LHR-B, 100% of LHR-C, and 51% of LHR-D of the CR1c insert. In addition, it regenerated the SmaI site at junction 2335/4894 bp and maintained the correct translational frame. pBL-CR1c1 was digested with XhoI and the CR1 insert was separated from the pBluescript® vector. The isolated CR1 fragment was then inserted into the unique XhoI site of expression vector pTCSgpt to produce plasmid pT-CR1c1.

11.2.4.2. pT-CR1c2 pBSCR1c was digested with ClaI and BalI, resulting in two fragments of size 3.96 kb and 5.9 kb. These fragments were purified from an agarose gel. Plasmid pBR322 was digested with ClaI and BalI and the 2.9 kb pBR322 fragment was purified and ligated to the 5.9 kb fragment from pBSCR1c. *E. coli* DH5α cells were transformed with the ligation mix and the resulting plasmid was termed pBR8.8. This plasmid was digested with XbaI, generating two fragments of size 7.45 kb and 1.35 kb. The 7.45 kb fragment was purified from an agarose gel and religated to itself. The resulting plasmid, pBR7.45, was digested with ClaI and BalI, and the isolated 4.5 kb fragment containing the sCR1 cDNA was ligated to the 3.96 kb fragment from pBSCR1c, resulting in plsmid pBL-CR1c2. This construct removed 90% of LHR-B in the sCR1 insert, regenerated the XbaI site at junction 1637/2987 bp, and maintained the correct reading frame. pBL-CR1c2 was digested with XhoI, and the sCR1 insert was separated from the pBluescript® vector. The isolated sCR1 fragment was then inserted into the unique XhoI site of expression vector pTCSgpt to produce plasmid pT-CR1c2.

11.2.4.3. pT-CR1c3 pBSCR1c was digested with NsiI resulting in three fragments of sizes 1.09 kb, 1.35 kb, and 7.46 kb. The 7.46 kb fragment was purified from an agarose gel and religated to itself, thus generating plasmid pBL-CR1c3. This construction removed 77% of LHR-A and the rest of the CR1 insert. The NsiI site was regenerated at junction 463/2907 bp. The translational frame was modified such that a nonsense codon was introduced immediately following the regenerated NsiI site. pBL-CR1c3 was digested with XhoI and the sCR1 insert separated from the pBluescript® vector. The isolated sCR1 fragment was then inserted into the unique XhoI site of expression vector pTCSgpt to produce plasmid pT-CR1c3.

11.2.4.4. pT-CR1c4 pBSCR1c digested with PstI. The PstI site in the polylinker region of pBluescript® had been removed during ligation of the CR1 cDNA to this vector (Example 8.1, supra). The resulting fragments of size 1.35 kb and 8.5 kb were separated by gel electrophoresis, and the 8.5 kb fragment was purified and religated to itself, generating plasmid pBL-CR1c4. This construction removed 31% of LHR-A and 69% of LHR-B of the sCR1 insert. The PstI site was regenerated at junction 1074/2424 bp, thus maintaining the correct reading frame. pBL-CR1c4 was digested with XhoI and the sCR1 insert separated from the pBluescript® vector. The isolated sCR1 fragment was then inserted into the unique XhoI site of expression vector pTCSgpt to produce plasmid pT-CR1c4.

11.2.4.5. pT-CR1c5 pBL-CR1c1 was digested with SmaI, thus linearizing the plasmid at the unique SmaI site. The plasmid was dephosphorylated, and ligated to phosphorylated NheI linker containing a Nonsense codon (New England Biolabs, Beverley, Mass.). This type of linker contains a translational stop codon in all three possible reading frames, and it also contains an NheI restriction site, which faciliates confirming the presence of the nonsense linker in the sCR1 cDNA. The resulting plasmid was named pBL-CR1c5, and it retained LHR-A and 62% of LHR-B of the sCR1 cDNA. pBL-CR1c5 was digested with XhoI, and the sCR1 insert was separated from the pBluescript® vector. The isolated sCR1 fragment was then inserted into the unique XhoI site of expression vector pTCSgpt to produce plasmid pT-CR1c5.

11.3. Expression of Soluble CR1

As demonstrated herein, the expression of a soluble form of CR1 that can be secreted from cells in high yield is (i) not limited to one exact site in the CR1 cDNA to be used for deletion or truncation, and (ii) is also not limited to the use of a particular expression vector (see infra). The ability to produce secreted sCR1 was demonstrated in two different expression systems.

11.3.1. Construction of pTCS Series of Expression Vectors

The pTCS series of expression vectors which were used consists of three plasmids, each with a unique XhoI cloning site for insertion of cDNAs (FIG. 21). Transcription of the inserted cDNA is driven by a set of tandem promoters. The SV40 early promoter which is located upstream of the adenovirus 2 major late promotor (AD2 MLP). Between the beginning of the cDNA and the AD2 MLP is the adenovirus tripartite leader. Transcribed mRNAs are terminated at a polyadenylation signal provided by the murine immunoglobulin kappa (Igκ) sequences located downstream of the XhoI cDNA cloning site. Selectable markers xanthine-guanine phosphoribosyltransferase (gpt), dihydrofolate reductase (dhfr), or neomycin resistance (neo$^r$) were provided by the insertion of the corresponding markers from pSV2gpt, pSV2dhfr, or pSV2neo, respectively. These plasmids were also the source of the bacterial origin of replication and beta-lactamase gene for ampicillin resistance. In general, the choice of which of these vectors to use depends upon which selectable marker or combination of markers is preferred for selection of the recombinants.

The complete DNA sequences are known for adenovirus 2 (Ad2), SV40, pSV2cat (Gorman, C., 1985, DNA Cloning, Volume II, A Practical Approach, ed. D. M. Glover, IRL Press, pp. 143–190), and murine immunoglobulin kappa. Sequences are located in the GenBanke database and the National Biomedical Research annotation and references. Any of these sequences could also serve as a source for the appropriate segments of the pTCS vectors.

The vectors pTCSgpt, pTCSneo, and pTCS dhfr were constructed from the intermediate plasmids pEAXgpt and pMLEgpt as follows:

11.3.1.1. Construction of pEAXgpt

Step 1. The Ad2 MLP DNA fragment was derived from M13 mp9/MLP (Concino, M. F., et al., 1983, J. Biol. Chem. 258: 8493–8496). This plasmid contains adenovirus 2 sequences of nucleotides 5778 (XhoI site) to 6231 (HindIII site) including the PvuII restriction site at nucleotide 6069 and the SacII site at nucleotide 5791 (see NBRF Nucleic database, accession #Gdad2). The XhoI to HindIII fragment had been cloned into the HindIII and SalI sites of M13 mp9 to generate plasmid M13 mp9/MLP.

Plasmid M13 mp9/MLP was digested with EcoRI and HindIII and the smaller MLP containing fragment isolated. A pUC plasmid (Pharmacia, Inc., Piscataway, N.J.) was also digested with EcoRI and HindIII and the larger fragment from this plasmid was then ligated to the EcoRI to HindIII MLP fragment. This resulted in a new MLP-containing plasmid with the plasmid backbone of pUC. This plasmid was digested with SmaI, ligated to SalI linkers, and recircularized. This new plasmid was then digested with PvuII which cleaved the plasmid at the PvuII site located at position #6069 within the adenovirus 2 insert sequences. The resulting linear fragment was ligated to XhoI linkers and recircularized. This plasmid was then digested with XhoI and SalI and the smaller fragment containing MLP DNA was isolated (fragment #1).

Step 2. Plasmid, pSV2gpt (American Type Culture Collection (ATCC) Accession No. 37145), was digested with PvuII, ligated to SalI linkers, and digested with SalI. The final product was a linear pSV2gpt fragment that served as the source of the gpt gene (fragment #2).

Step 3. A murine immunoglobulin Igκ fragment (Hieter, P. A., et al., 1980, Cell 22: 197–207) was digested with HaeIII and AvaII and the fragment containing the polyadenylation sequences isolated. In the murine Ig kappa sequence available in the NBRF Nucleic database (accession #Kcms), the Ig stop codon is at position 1296, followed by the AvaII site at 1306, the AATAAA polyadenylation site at 1484, and the HaeIII site at 1714. The overhanging ends of this fragment were filled in with E. coli DNA polymerase, and the fragment was then ligated to XhoI linkers, and digested with XhoI. This fragment (fragment #3) served as the source of the polyadenylation site.

Step 4. Fragments 1, 2, and 3 were ligated together with T4 DNA ligase to produce a circular plasmid. The correct orientation of the fragments in this plasmid was confirmed by restriction enzyme analysis. Downstream of the XhoI cDNA cloning site was the murine kappa polyadenylation site, and further downstream from this site was the SV40 promoter and gpt gene. Upstream of the XhoI site was the MLP promoter and further upstream from this promoter was the bacterial origin of replication and ampicillin gene. This plasmid was then digested with SalI and the overhanging ends filled in with E. coli DNA polymerase. The resulting blunt end fragment was ligated to EcoRI linkers and recircularized with T4 DNA ligase. This final plasmid was designated pEAXgpt.

11.3.1.2. Construction of pMLEgpt

Step 1. Plasmid pMLP CAT (Lee, R. F., et al., 1988, Virology, 165: 51–56) is an expression plasmid with a pML vector backbone and contains the adenovirus 2 MLP and tripartite leader sequences 5' to the CAT gene. PMLP CAT was digested with XhoI and SacII; the XhoI cut at a site between the CAT gene and the L3 region of the tripartite leader, and SacII cut at position #5791 within the adenovirus DNA but 5' of the MLP. The AD2 MLP and tripartite leader were thus located on this small XhoI to SacIII fragment (fragment #4).

Step 2. Plasmid pEAXgpt was digested with XhoI and SacII, and the smaller MLP containing fragment was discarded. The larger fragment (fragment #5) was isolated. Fragments 4 and 5, both with SacII and XhoI ends, were ligated to produce plasmid pMLEgpt.

11.3.1.3. Construction of pTCSgpt

Step 1. pMLEgpt was digested with SacII and the ends filled in with T4DNA polymerase to yield a blunt end fragment (fragment #6). This SachII site is located at nucleotide 5791 in the Adenovirus 2 sequence, 5' of MLP-tripartite leader.

Step 2. pSV2dhfr (ATCC Accession No. 37146) was digested with HindIII and PvuII. The smaller 342 nucleotide fragment containing the SV40 early promoter was blunt ended using the Klenow fragment of E. coli DNA polymerase (fragment #7). Fragments 6 and 7 were ligated with T4 DNA ligase. Restriction enzyme analysis confirmed that the fragments were correctly oriented to give two, tandem promoters upstream of the XhoI cDNA cloning site, each promoter able to prime RNA synthesis in the same direction. This plasmid was named pTCSgpt (FIG. 22).

11.3.1.4. Construction of pTCSdhfr

Step 1. pSV2dhfr was digested with HindIII and PvuII, and the larger fragment was then purified from an agarose gel (fragment #8). The smaller SV40 early promoter containing fragment was discarded.

Step 2. pTCSgpt was digested with EcoRI and then filled in with the Klenow fragment of E. coli DNA polymerase to generate blunt ends. This linear fragment was then digested with HindIII, and the fragment (about 1600 nucleotides) containing the pTCS transcription unit of SV40 promoter, MLP, tripartite leader, XhoI cDNA cloning site, murine Igλ sequences, and second SV40 promoter was isolated (fragment #9). This fragment had one flush end and one HindIII overhanging end. Ligation of fragments 8 and 9 generated plasmid pTCSdhfr.

11.3.1.5. Construction of pTCSneo

Step 1. pSV2neo (ATCC No. 37149) was digested with HindIII and BamHI, and the larger fragment (fragment #10) was isolated. This fragment contained the plasmid backbone and neo gene.

Step 2. pTCSdhfr was digested with HindIII and BamHI, and the pTCS transcription unit (fragment #11) was isolated from an agarose gel after electrophoresis of the digestion products. Ligation of fragments 10 and 11 generated plasmid pTCSneo.

11.3.2. Expression and Assay of Plasmids pBSCR1c, pBSCR1s and pBM-CR1c, Mammalian Expression Vectors Containing Soluble CR1 Coding Sequences

11.3.2.1. Expression of CR1 Constructs Truncated at Different Positions within the CR1 cDNA Plasmids pBSCR1c and pBSCR1s were constructed (Section 11.1, supra) such that most of the cDNA coding regions, except the transmembrane and cytoplasmic regions were preserved (FIG. 20). pBSCR1s is shorter than pBSCR1c since it is also missing a portion of LHR-D and SCRs 29 and 30 that are present in pBSCR1c. The sCR1 portions of these plasmids were inserted into pTCSgpt, followed by transfection and expression as described infra.

pBSCR1c/pTCSgpt construction: pBSCR1c was digested with XhoI to yield the 5.9 kb insert, sCR1c. sCR1c was inserted into the XhoI cDNA cloning site of pTCSgpt to produce pBSCR1c/pTCSgpt.

pBSCR1s/pTCSgpt construction: pBSCR1s was digested with XhoI and PvuI to release the sCR1s insert. The ends of the insert were made blunt with T4 DNA polymerase. This insert was purified from an agarose gel. Vector pTCSgpt was digested with XhoI, and the overhanging XhoI ends were filled in with $E.$ $coli$ DNA polymerase I. Next, the sCR1s insert was ligated to the blunt end vector to produce pBSCR1s/pTCSgpt.

Plasmids pBSCR1c/pTCSgpt and pBSCR1s/pTCSgpt were digested with FspI, and the resultant linear DNA's were transfected into Chinese Hamster Ovary cells that were mutant in the dhfr gene (CHO DUX B11 cells) via calcium phosphate coprecipitation with plasmid pSV2dhfr. Transfectants were selected by their ability to grow in DHFR selection medium. Culture supernatants of transfectant clones were assayed for secreted sCR1 by ELISA. Culture supernatants from fifty pBSCR1c/pTCSgpt recombinants were assayed and the positive recombinants were taken through the amplification process by culturing them in increasing concentrations of methotrexate. In addition, pools of transfectants were prepared by co-culturing eight pBSCR1c/pTCSgpt transfectants together per pool and carrying them through the same amplification process. Results of the amplification are presented in Table VI.

TABLE VI

EXPRESSION OF pBSCR1c/pTCSgpt

Secreted Soluble CR1 (μg/ml)

| CLONE | 0 MTX | 20 nM MTX | 50 nM MTX | 100 nM MTX | 500 nM MTX |
|---|---|---|---|---|---|
| 2* | 0.7 | 3.4 | 11 | 10.9 | |
| 4 | 0.04 | 0.1 | | | |
| 6 | 0.04 | | | | |
| 9 | 0.02 | | | | |
| 10 | 0.2 | | | | |
| 11 | 0.12 | | | | |
| 12 | 0.14 | | | | |
| 13 | 0.07 | | | | |
| 14 | 0.2 | | | | |
| 15 | 0.45 | 1.1 | 7.3 | 9.0 | |
| 21 | 0.07 | | | | |
| 30 | 0.27 | <0.02 | <0.02 | | |
| 35*† | 0.82 | 6.3 | 8.4 | 10.9 | 10.9 |
| 40 | 0.05 | | | | |
| 41 | 0.05 | | | | |
| 50 | 0.12 | | | | |
| 52 | 0.12 | | | | |
| POOL | | | | | |
| A | | 0.02 | | | |
| B | | 0.04 | | | |
| C | | 0.23 | | | |
| D | | <0.02 | <0.02 | | |
| E | | 0.27 | 1.1 | | |
| F | | 3.6 | 5.8 | 9.1 | |
| G | | 0.27 | | | |
| H | | 0.04 | | | |

*clones 2 and 35 were chosen for large scale production of sCR1.
†Clone 35 was subcloned by limiting dilution, and the production of soluble CR1 was determined for each subclone. pBSCR1c/pTCSgpt-clone 35.6 was the highest producer, showing 17.7 μg/ml sCR1.
MTX: methotrexate Twelve recombinants from pBSCR1s/pTCSgpt were assayed for production of soluble CR1 by ELISA. All twelve candidates showed detectable levels of secreted sCR1. The best producers gave levels of sCR1 which were comparable to those produced by the best pBSCR1c/pTCSgpt transfectants.

pBSCR1c/pTCSgpt and pBSCR1s/pTCSgpt recombinants produced soluble CR1 with similar levels of production. This indicated that the ability to produce a soluble CR1 polypeptide was not dependent upon an exact truncation point within the CR1 cDNA.

11.3.2.2. Expression of sCR1c in Two Different Expression Systems

The truncated CR1 cDNA insert, sCR1c, was inserted into the expression vector pTCSgpt and expressed as described above. It was also inserted into the expression vector pBMT3X as described supra in Section 11.2.3, to yield pBM-CR1c. Both these expression vectors have very strong promoters. Expression of soluble CR1 was tested in both systems to determine whether one system would produce better yields of secreted polypeptide.

C127I mouse cells (ATCC Accession No. CRL 1616, Rockville, Md.) were transfected with pBM-CR1c using the calcium phosphate method (Graham, F. L. and van der Eb, A. J., 1973, Virology 52: 456–467). After glycerol shock, the cells were refed with D-MEM medium containing 10% fetal bovine serum and 2 mM L-glutamine, and incubated at 37° C. for 48 hours. Thereafter, the cells were trypsinized, and split at 1:5 and 1:10 ratios into complete D-MEM medium plus 10 μM cadmium chloride. Cadmium-resistant colonies appeared within 10 days. Ten colonies were removed with the use of cloning cylinders. Each colony was transferred to a 60 mm petri dish containing complete D-MEM medium, and incubated at 37° C., 5% $CO_2$ until the cells reached confluency. Thereafter, for each dish, the cells were trypsinized and divided into three 60 mm dishes to be used for preparation of frozen cell stocks, RNA extraction, and ELISA test of the cell medium for the presence of secreted sCR1c.

When cell medium from each confluent petri dish was removed and subjected to ELISA analysis, all pBM-CR1c clones tested were positive for soluble CR1 production. The levels of secreted sCR1 from the pBM-CR1c recombinants were comparable to those from the pBSCR1c/pTCSgpt recombinants. This indicated that the ability to produce high levels of secreted sCR1 polypeptide was not dependent upon the use of only certain promoters or expression systems.

11.3.3. Expression and Assay of Plasmids pT-CR1c1, pT-CR1c2, pT-CR1c3, pT-CR1c4, and pT-CR1c5, Mammalian Expression Vectors Containing Soluble CR1 Coding Sequences The pT-CR1c series of deletion mutants were missing the transmembrane and cytoplasmic domains, as were the constructs, pBSCR1c and pBSCR1s. In addition, the deletion mutants also contained fairly large deletions of various LHR regions of the CR1 cDNA (see FIG. 20). The deletion mutants were expressed in CHO DUX B11 cells and the levels of soluble CR1 polypeptide produced were measured.

For each deletion construct, forty different pools of clones were selected for ELISA analysis to determine whether soluble CR1 polypeptides were being produced. All five pT-CR1c constructs were found to be secreting sCR1 into the cell culture medium, as determined either by ELISA or by the presence of functional activity in the cell culture media. Supernatants from cells transfected with four of the five pT-CR1c constructs were producing sCR1 that was functional as determined by a hemolytic assay (see Table VII and Section 13.2, infra).

TABLE VII

PRODUCTION OF FUNCTIONAL sCR1 FRAGMENTS*

| Construct | ELISA | Hemolytic Assay |
|---|---|---|
| pT-CR1c1 | − | + |
| pT-CR1c2 | + | + |
| pT-CR1c3 | − | + |
| pT-CR1c4 | + | Not determined |
| pT-CR1c5 | − | + |

*Supernatants tested for ELISA or hemolytic assays were obtained either from cultures growing in T75 flasks or in 24 well dishes. Since various amounts of soluble CR1 could have accumulated in the culture supernatants under these conditions, the results shown are qualitative. (+) indicates the production of functional sCR1 as detected by the indicated assay.

The fact that the deletion mutants were also able to produce soluble CR1, further demonstrated that the ability to express sCR1 was not dependent upon one exact genetic modification of the CR1 cDNA. As long as the transmembrane regions were deleted, all constructs were able to produce a soluble polypeptide.

12. EXAMPLE

Production and Purification of Soluble CR1

Large quantities of sCR1 were produced in a hollow fiber bioreactor system. The quantities of sCR1 obtained were proportional to the relative yield of the inoculated recombinant clones. For optimal purification results, a serum-free medium was chosen that resulted in high production levels of sCR1 in the absence of large quantities of exogenously added fetal calf serum polypeptides.

12.1. Large Scale Production of Soluble CR1

A Cell-Pharm™ Cell Culture System I (CD Medical, Inc., Miami Lakes, Fla.), equipped with a model IV-L hollow fiber bioreactor (30 kD molecular weight cutoff), was assembled under sterile conditions. Two clones (clone 2 and clone 35 of pBSCR1c/pTCSgpt) were expanded into eight T-225 flasks. At confluency, the cells were trypsinized, washed, pelleted, and resuspended in culture media. Approximately $5 \times 10^8$ cells of clone 2 and $10 \times 10^8$ cells of clone 35 were inoculated into two separate hollow fiber bioreactors. A 20 liter feed reservoir of alpha-MEM plus 10% fetal calf serum, 8 mM L-glutamine, 100 $\mu$g/ml penicillin-streptomycin and the appropriate concentration of methotrexate (50 nM for clone 2; 500 nM for clone 35) was used. Premixed gas (5% $CO_2$ in air) was bubbled into the reservoir medium through the oxygenator to maintain pH. Media recirculation, replacement and gas flow rates were adjusted to yield maximum production. Samples were harvested through inoculating ports, centrifuged at 1000 rpm for 10 minutes, filtered through a 0.22 $\mu$M pore size filter, and kept at 4° C. before purification. Harvest volume and frequency were increased gradually from 25 ml, three times per week at the beginning of the culture, to 40 ml, five times a week after 2–3 months. The production of sCR1 was assayed by a CR1 ELISA. The yields of clone 2 and clone 35 for the first month after inoculation were 66 $\mu$g/day and 1060 $\mu$g/day, respectively. These yields increased as the cultures became established.

12.1.1. Production of sCR1 in Serum-Free Media

Two commercially available serum-free media were tested for their ability to support cell growth and production of sCR1. A confluent T75 flask of pBSCR1c/pTCSgpt clone 35 was divided into two T75 flasks. one flask was cultured with alpha MEM, supplemented with 10% fetal calf serum, L-glutamine, antibiotics, and 500 nM methotrexate. The other flask was weaned stepwise from 5%, 1%, 0.5% and no fetal calf serum in alpha MEM plus L-glutamine, antibiotics, 500 nM methotrexate plus HB CHO growth supplement (Hana Biologics, Inc., Alameda, Calif.). The cell growth and sCR1 production levels of the two flasks were compared. The growth of the cells in the serum-free media never reached confluency. The levels of sCR1 production are given in Table VIII. In each case, the level of sCR1 production was best when cells were grown in 10% fetal calf serum. For comparison, the levels found at day 14 in serum-free media were $1.4 \times 10^{10}$ ghosts/ml as compared to $4.2 \times 10^{10}$ ghosts/ml for 10% fetal calf serum supplemented media.

TABLE VIII

PRODUCTION OF sCR1 IN SERUM-FREE MEDIA SUPPLEMENTED WITH CHO GROWTH SUPPLEMENT VERSUS 10% FETAL CALF SERUM CONTAINING MEDIA

| | Day 4 | Day 7 | Day 11 | Day 14 |
|---|---|---|---|---|
| Flask 1 CHO Growth Supplement Plus | 5% FCS 2.6 | 1% FCS 2.4 | 0.5% FCS 2.95 | 0% FCS 1.4 |
| Flask 2 10% FCS | 4.8 | 3.85 | 4.3 | 4.2 |

*expressed as $10^{10}$ ghosts/ml

Cell growth and sCR1 production in recombinants were tested using a second source of serum-free media (CHO-1, Ventrex Laboratories, Inc., Portland, Me.). Since it was not necessary to wean serum-grown cells into this media, cells were thawed and cultured directly in the serum-free media. This media consists of a DME-F12 base and a growth additive. Equal numbers of cells were thawed and seeded into separate wells in a 24-well plate. After the cells had attached, the media was discarded, and either 10% fetal calf serum containing media or serum-free media was added to appropriate wells. Each condition was performed in duplicate. Unlike the previously tested serum-free media, the CHO-1, Ventrex Laboratories media yielded similar levels of cell growth as did the fetal calf serum containing media.

12.1.2. Conclusions

The above-described results indicated that sCR1 producing CHO cells could be maintained in a defined serum-free media. This resulted in a savings in the cost of culture media for large scale production runs. A further advantage was that purification of sCR1 from the cell culture supernatants was simplified, since no fetal calf serum proteins had to be removed.

12.2. Purification of Soluble CR1

With the advent of specific anti-CR1 antibodies, it became possible to replace the many chromatographic steps needed to produce purified CR1 with a simplified two step procedure. This increased the yields of CR1 proteins that could be obtained to approximately 1–5 mg CR1 per $5.9 \times 10^{13}$ erythrocytes (Wong, W. W., et al., 1985, J. Immunol. Methods 82: 303–313). However, since the reported purification was of membrane-bound forms of CR1, it was always necessary to solubilize the CR1 containing material in detergents.

Soluble CR1 produced by recombinant transfectants does not have to be solubilized with detergents for purification; it is already soluble. Although soluble CR1 can be purified by anti-CR1 antibody chromatography (see below), this procedure does not lend itself easily to large-scale production. The extent of scale-up is limited by the amount of anti-CR1 antibody that can be obtained for preparing the antibody matrix of the antibody purification columns. In addition, the high binding affinity of an antibody such as YZ-1 for CR1 means that rather harsh conditions, for example pH 12.2, have to be used to remove the bound sCR1 product from the antibody matrix (Wong, W. W., et al., 1985, J. Immunol. Methods 82: 303–313).

To have the capacity of purifying very large quantities of soluble CR1, purification procedures involving HPLC columns were developed. These HPLC columns can easily be scaled up to produce even larger quantities of purified soluble CR1. In addition, they do not require harsh conditions for the elution and recovery of sCR1.

12.2.1. Antibody Affinity Column Purification

12.2.1.1. Methods

For antibody affinity purification of sCR1, 100 mg of monoclonal antibody YZ-1 was covalently coupled to 7 mg of AffiGel-10 (BioRad, Richmond, Calif.) according to the manufacturer's instructions. CR1 containing supernatant from cell cultures was incubated with the immobilized YZ-1 in a flask rocking at 4° C. overnight. The material was poured into a glass column and washed extensively with 10 mM Hepes, 0.1M NaCl, pH 7. The sCR1 was eluted using 20 mM sodium phosphate, 0.7M NaCl, pH 12 (Yoon, S.H. and Fearon, D. T., 1985, J. Immunol. 134: 3332–3338). Eluted fractions were tested for the presence of protein using the Biorad Protein Assay (BioRad, Richmond, Calif.). Samples containing protein were immediately pooled and dialyzed in 0.1M Hepes pH 7 overnight (2×1 liters) at 4° C. The sample was then dialyzed in PBS. Presence of sCR1 was analyzed by CR1 ELISA.

12.2.1.2. Results

Cell culture supernatant containing sCR1 produced by transfectant pBSCR1c/pTCSgpt clone 2 was loaded onto the anti-CR1 antibody affinity column and the peak sCR1 fractions pooled. An aliquot of this purified material was run on a 4–20% SDS-PAGE gel (DAIICHI; Inc., polyacrylamide gels; modified procedure of Laenali, U. K., 1970, Nature 227: 680–685). Under reducing conditions, the apparent molecular weight of soluble CR1 was about 224,000 daltons (FIG. 24). This purified CR1 was also shown to be active by its ability to inhibit complement-mediated hemolysis as well as C5a and C3a production (Section 13, infra).

12.2.2. CR1 Purification by HPLC

12.2.2.1. Methods

12.2.2.1.1. Starting Material

When cultures were first established in the bioreactors, the levels of sCR1 production were lower than when the cultures had been growing for several months. Generally there was a period of several weeks before the cells in the bioreactor reached confluency and produced maximum levels of sCR1. Cell culture supernatants with low levels of sCR1 could be concentrated before purification by either ammonium sulfate precipitation or by ultrafiltration. Ammonium sulfate fractionation of supernatants over the range of 60 to 80% saturation precipitated sCR1 in essentially equivalent yields. The precipitate was dissolved in a minimum volume and dialysed into starting buffer for the cation exchange HPLC. Alternatively, the CHO cell culture supernatants could be concentrated by ultrafiltration and dialyzed into starting buffer for cation exchange chromatography.

As the bioreactors produced higher concentrations of soluble CR1, the CHO cell culture supernatants from these cultures could be dialyzed directly into starting buffer for cation exchange chromatography.

12.2.2.1.2. Cation Exchange HPLC Procedure

Samples were dialyzed into starting buffer (0.02M sodium phosphate, 0.06N sodium chloride, pH 7.0) and then filtered through a 0.2 μm filter to remove any particulate material. The sample was then loaded onto a cation exchange high pressure liquid chromatography column (10 cm×10 mm, Hydropore-SCX HPLC column from Rainin). The column was washed and eluted with a sodium chloride gradient developed using 0.02M phosphate, 0.5N NaCl, pH 7.0. The sCR1 eluted somewhere between 0.06N and 0.25N NaCl. Elution was monitored by absorbance at 280 nm and by ELISA.

12.2.2.1.3. Anion Exchange HPLC Procedure

If desired, further purification of the cation HPLC purified sCR1 could be obtained by anion HPLC. Peak fractions from the cation HPLC were dialyzed into the starting buffer for anion HPLC. Samples were loaded and the column (Hydropore-AX from Rainin) was washed in 0.01M phosphate pH 7.5. The column was eluted with a series of steps and gradients developed using 0.01M phosphate, 0.5N NaCl, pH 7.5. The sCR1 eluted somewhere between 0.0N and 0.3N NaCl. Elution was monitored as before for cation exchange HPLC. The concentrations and pH of the cation and anion HPLC column buffers are given as examples only. Other buffer concentrations, salt conditions, or pH conditions would also work.

12.2.2.1.4. Western Blot Analysis

Western blotting was performed using a modified procedure from Towbin, H., et al., 1979, Proc. Natl. Acad. Sci. USA, 76: 4350–4354. Briefly, purified sCR1 was run on a 4–20% SDS-PAGE, transferred to nitrocellulose, specifically probed with anti-CR1 (mouse mAb YZ-1 or J3D3), and detected with goat anti-mouse antibody conjugated with alkaline phosphatase.

12.2.2.2. Results

For a typical run, 50–100 ml of supernatant from a bioreactor culture were dialyzed into starting buffer and loaded onto a 10 cm×10 mm cation exchange HPLC. The peak fractions were determined by ELISA and absorbance at 280 nm, and were pooled. The protein concentration of the pool was determined by absorbance at 280 nm ($\epsilon$(1%) at 280 nm =10, as estimated from the CR1c amino acid composition). Several tens of milligrams were purified from 100 ml of amplified culture supernatant.

As an example, 100 ml of culture supernatant from transfectant pBSCR1c/pTCSgpt clone 2 produced 22 mg of purified sCR1, as determined by absorbance at 280 nm, when purified by cation HPLC (FIG. 24). When monitored by CR1 ELISA, the yield was calculated to be 202% with another 13% in the flow-through or column wash fraction. The greater than 100% yield probably reflects matrix effects in the ELISA.

Given the rates that culture supernatant can be withdrawn from a bioreactor, it should be possible at this level of methotrexate amplification to produce about 100 mg of purified soluble CR1 per week per bioreactor. Some ways in which this level of production can be scaled up, include amplifying the starting cultures to a maximum extent with methotrexate prior to seeding the bioreactor, increasing the number of bioreactors in production at any one time, and using larger capacity HPLC columns.

12.2.2.3. Characterization of Purified Soluble CR1

The sCR1 containing peak fraction from the cation HPLC (FIG. 24) was further purified on an anion HPLC. The purity of the sCR1 material at the various steps was tested by SDS-PAGE (FIG. 25). The smaller bands seen in these heavily loaded gels represent fragments of sCR1 as determined by Western Blot analysis using anti-CR1 monoclonal antibodies, YZ1 or J3D3. The fragment sCR1 bands were not seen in most preparations. The functional activity of purified sCR1 was tested by its ability to inhibit classical complement-mediated hemolysis by 50% at a purified sCR1 concentration of 0.25 μg/ml. The purified soluble CR1 was also able to inhibit classical complement C5a production by 50% at 5 μg/ml and C3a production by 50% at 13 μg/ml (see Section 13, infra).

12.2.2.4. Conclusions

As described supra, we developed an improved method for the purification of soluble CR1 that can easily be scaled up to produce the quantities of sCR1 needed for therapeutic applications. The basic elements of this procedure included a starting material that is already soluble, thus eliminating the requirement of solubilizing membrane bound CR1 with detergents. The reduction of fetal calf serum concentrations in the bioreactor cultures and/or the use of alternative culture medias in these cultures eliminated the need to remove high concentrations of extraneous proteins from the sCR1-containing starting material during subsequent purification. Furthermore, the development of an HPLC procedure for purification provided a method for large-scale purification. Either cation HPLC or a combination of cation HPLC followed by anion exchange HPLC can be used for purification. Substantially pure soluble CR1 in high yield can be achieved by this procedure in only 1 or 2 steps.

13. Example

Demonstration of In Vitro Activity of Soluble CR1

13.1. Inhibition of the Neutrophil Oxidative Burst

In the reperfusion injury model of tissue damage incurred during a myocardial infarction, activated complement components induce neutrophil adhesion and activation. The activated neutrophil undergoes an oxidative burst creating highly toxic oxygen radicals. These and other potential toxins are released during neutrophil degranulation, damaging the surrounding tissue. Soluble CR1 may reduce the area of damaged tissue by preventing the generation of C3a and C5a, the complement components involved in neutrophil activation.

To monitor the ability of soluble CR1 to block the generation of C5a during complement activation in vitro, a bioassay which can quantitate the generation of oxygen radicals produced by neutrophils during a C5a induced oxygen burst was used (Bass, D. A., et al., 1983, J. Immunol. 130: 1910–1917). This assay employs dichlorofluorescin diacetate (DCFDA), a lipid soluble molecule which can enter cells, become trapped, and turn highly fluorescent upon oxidation.

13.1.1. Materials and Methods

13.1.1.1. Materials

Fresh whole blood, human complement sources (Beth Israel Hospital, Boston, Mass.), dried Baker's yeast, PBS with 0.1% gelatin and 5 mM glucose, 100 mM EDTA, 10 mM DCFDA in HBSS (Kodak), Red blood cell (RBC) lysing buffer (Ortho Diagnostics), purified C5a (Sigma Chemical Co., St. Louis, Mo.), and soluble CR1 were used.

13.1.1.2. Prearation of Neutrophils

Neutrophils were prepared as described by Bass (1983, J. Immunol. 130: 1910–1917). 2.0 ml of whole blood was washed 3 times in PBS-gelatin-glucose, resuspended in 5 ml of 10 μM DCFDA in HBSS plus 5 ml PBS-gelatin-glucose and incubated for 15 minutes at 37° C. Cells were then centrifuged and resuspended in 2.0 ml PBS-gelatin-glucose plus 5 mM EDTA.

13.1.1.3. Preparation of Yeast Particles

Dried baker's yeast was resuspended in $H_2O$, washed 2 times and boiled for 30 minutes. Particles were rewashed 2 times in $H_2O$ and resuspended at 0.5 grams/ml in $H_2O$ (Simpson, P. J., et al., supra).

13.1.1.4. Activation of Neutrophils by Purified C5a

100 μl of DCFDA-loaded cells were treated with RBC lysing buffer, washed one time in PBS-gelatin-glucose-EDTA and resuspended in 1.0 ml of PBS-gelatin-glucose. Fifty μl of purified C5a at 200 ng/ml or control was added to 0.5 ml of target cells at 37° C. and analyzed on the flow cytometer at various time intervals.

13.1.1.5. Activation of Neutrophils by Purified C5a in Human Serum or Plasma 100 μl of DCFDA-loaded cells were incubated with 50 μl of C5a diluted 1:1 in human serum or heparinized plasma (100 ng/ml) or control at 37° C. for 30 minutes. The RBC's were lysed out, and the neutrophils were analyzed on a flow cytometer.

13.1.1.6. Activation of Neutrophils by Yeast Particle-Activated Human Serum or Plasma 425 μl of fresh frozen serum and plasma plus 50 μl of sCR1 or control were incubated with 25 μl of yeast particles at 37° C. for 30 minutes. The complement-activated and control samples were then centrifuged to remove the yeast particles. Ten 2-fold dilutions of each of these samples were performed in PBS-gelatin-glucose-EDTA. 50 μl of each serial dilution of control and activated serum and plasma was added to 50 μl of DCFDA-loaded target cells and incubated at 37° C. for 30 minutes. The RBC's were then lysed out, and neutrophils were analyzed by flow cytometry.

13.1.2. Results

13.1.2.1. C5a Induces an Oxygen Burst in Human Neutrophils which can be Measured using DCFDA FIGS. 26a–26g show a rapid increase in fluorescence intensity of the human neutrophils after stimulation with purified C5a. Within four minutes after addition of C5a (20 ng/ml final concentration), the neutrophils were 10-fold brighter than control DCFDA-loaded neutrophils. By 20 minutes, the neutrophils were 20-fold as bright as controls. This assay seems to be a sensitive indicator of C5a.

13.1.2.2. Human Serum Blocks the Oxygen Burst Effects of Purified C5a on Neutrophils No increase in fluorescent intensity was observed in neutrophils loaded with DCFDA and incubated with purified C5a diluted in human serum. This effect may be due to platelet derived growth factor (PDGF) released from platelets during clotting. It has been shown that low levels of PDGF can inhibit C5a-induced neutrophil activation (Wilson, E., et al., 1987, Proc. Natl. Acad. Sci. USA 84: 2213–2217).

13.1.2.3. Heparinized Plasma does not Block the Effects of C5a on Neutrophils C5a diluted 1:1 in heparinized plasma induced an oxygen burst in DCFDA loaded neutrophils. Although not as dramatic as C5a in buffer, there was a ten-fold increase in fluorescent intensity after a 30 minute incubation with the neutrophils. The decreased signal may be caused by PDGF release during phlebotomy or plasma isolation. More gentle and rapid isolation of the plasma from the cellular components of blood may minimize the release of PDGF and allow for better C5a function.

13.1.2.4. sCR1 Present During Complement Activation Blocks C5a Generation

Figure 27A:
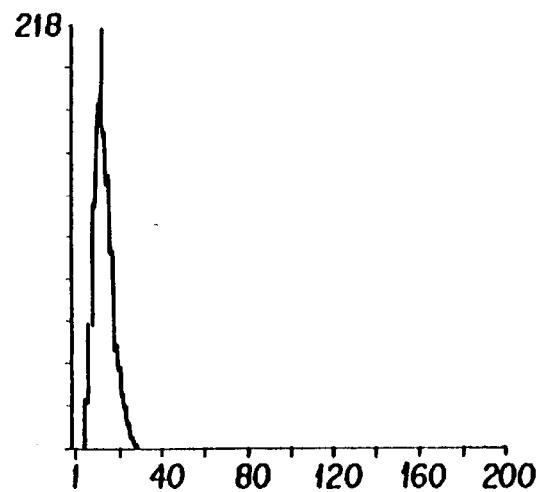
Figure 27B:
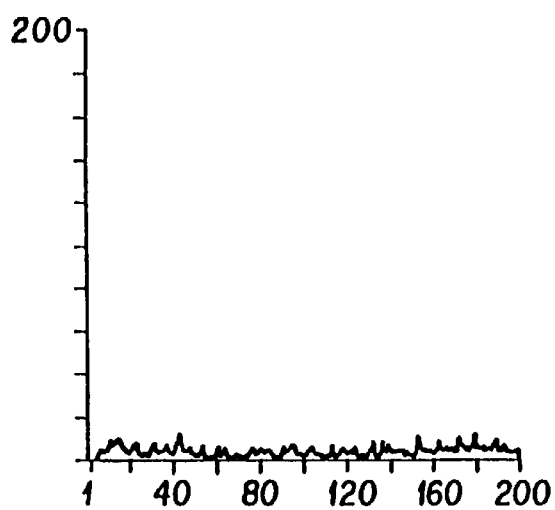
Figure 27C:
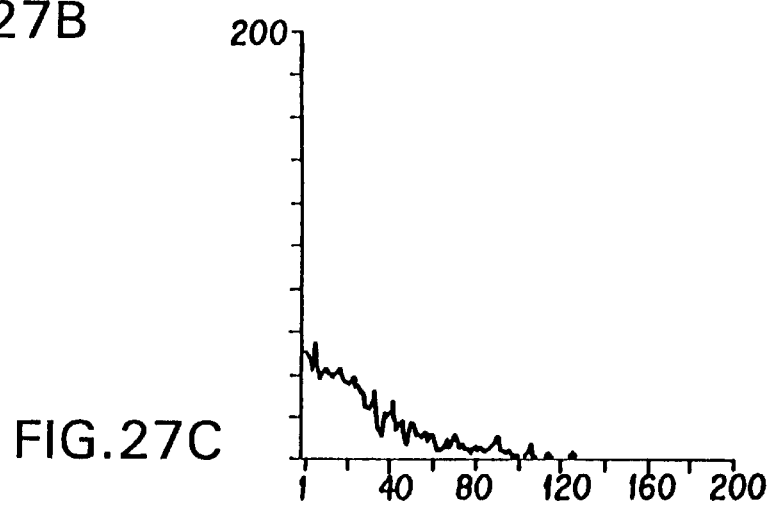

Zymosan induced activation of human complement in the presence of soluble CR1 showed reduced C5a activity as measured with the DCFDA assay. As can be seen in FIGS. 27a–27c, the 1:16 dilution of human plasma activated in the presence of sCR1 generated 70% less fluorescence intensity increase in the neutrophils as the 1:16 diluted plasma activated without sCR1 present. This implies inhibition of C5a generation by sCR1. Further optimization of the DCFDA assay and plasma collection should result in a more dynamic and sensitive assay of soluble CR1 activity.

13.2. Inhibition of Complement Mediated Hemolysis

13.2.1. Methods

The ability to inhibit complement was tested by assaying for inhibition of complement-mediated red cell lysis (hemolysis). The inhibition of hemolysis was determined as a function of soluble CR1 concentration. The sCR1 samples to be tested were diluted in 0.1M Hepes buffer (0.15N NaCl, pH 7.4), and 50 μl were added to each well of a V-bottom microtiter plate typically in triplicate. Human serum, used as the complement source, was diluted 1 to 125 in Hepes buffer, and 50 μl were added to each well. Next, commercially available sheep erythrocytes with anti-sheep antibody (Diamedix Cat. No. 789-002) were used as received and added 100 μl/well to initiate the complement pathway leading to hemolysis. The plate was incubated for 60 minutes at 37° C. and then centrifuged at 500×g for 10 minutes. The supernatants were removed and placed in a flat-bottom microtiter plate. The extent of hemolysis was measured as a function of the sample absorbance at 410 nm. The maximal absorbance (corresponding to maximal hemolysis), $A_{max}$, was obtained from the absorbance of an erythrocyte sample containing only human serum $A_s$, minus the absorbance of a sample containing only the red cells, $A_O$. Thus, $A_{max}=A_S-A_O$. The difference between the absorbance of an erythrocyte sample containing both human serum and sCR1, and the absorbance of a cell sample containing sCR1 only, was defined as $A_{sample}$. The inhibition, IH, was expressed as the fraction $(A_{max}-A_{sample}/A_{max})$ and $IH_{50}$ was defined as the concentration of sCR1 required to produce a value of IH=½. To monitor chromatography fractions, the serum-free controls were not included and anti-complement activity was monitored qualitatively as a decrease in the absorbance at 410 nm of the sample.

The hemolytic assay described above was also used to assess the capability of human recombinant sCR1 to inhibit sheep red cell lysis by complement from other species, such as guinea pig and rat. For each species, fresh-frozen serum or freshly lyophilized serum or plasma was used as a complement source. In some cases sera were obtained commercially (Sigma Chemical Company, St. Louis, Mo.).

The serum was first titered for its capacity to lyse activated red cells. The greatest dilution which yielded at least 80% maximal red cell lysis was chosen to assess the effects of added human sCR1. The assay was then performed as described above, substituting animal for human serum at the preferred dilution.

13.2.2. Results

As indicated in FIG. 28, purified sCR1 inhibited classical complement-mediated lysis by 50% at a sCR1 concentration of 0.12 μg/ml. The ability of antibody affinity purified sCR1 to inhibit the hemolytic assay was compared to that of unpurified material (sCR1 containing cell culture supernatant). The purified sCR1 had activity comparable to that of the unpurified sCR1, with both producing 50% inhibition in the hemolytic assay at $1.6 \times 10^8$ ghosts/ml. This indicated that the purification procedure was not substantially diminishing the functional activity of the final sCR1 product.

To determine if purified sCR1 could be stored frozen, an aliquot was stored at −70° C. for one week. The concentration of the frozen sCR1 was the same as the nonfrozen sCR1, as determined by absorbance at 280 nm and CR1 ELISA. The frozen sCR1 also had the same activity as the nonfrozen sCR1 as determined by inhibition of hemolysis.

The ability of human recombinant sCR1 to inhibit hemolysis mediated by complement from several species is summarized in Table IX.

TABLE IX

HEMOLYSIS OF SENSITIZED SHEEP RBC USING
COMPLEMENT FROM VARIOUS ANIMAL SERA

| Animal | Final Conc. Serum Used | Inhibition by sCR1 | Inhibition (IH)** (ghost/ml) | IH$_{50}$** (ghost/ml) |
|---|---|---|---|---|
| guinea pig* | 1:500 | Yes | 66%(2.6 × 10$^9$) | 1.0 × 10$^9$ |
| human | 1:500 | Yes | 94%(2.5 × 10$^9$) | 2.0 × 10$^8$ |
| human | 1.312 | Yes | 94%(1.2 × 10$^9$) | 1.0 × 10$^7$ |
| rat | 1:200 | Yes | 85%(2.6 × 10$^9$) | 2.4 × 10$^8$ |
| rat* | 1:200 | Yes | 77%(3.8 × 10$^9$) | 1.0 × 10$^9$ |
| dog | 1:50 | No | | |
| rabbit* | 1:20 | No | | |
| mouse* | 1:5 | No | | |

*lyophilized sera obtained commercially (Sigma Chemical Co., St. Louis, Mo.
**as defined in text (Section 13.2)

Both guinea pig and rat complement appeared to be inhibited by human sCR1. The lack of clear inhibition for other species may reflect (a) the inappropriateness of using rabbit antibodies and sheep erythrocytes in the assay system, or (b) the high concentration of serum required for hemolysis in this system.

13.3. Inhibition of C3a and C5a Production

13.3.1. Methods

The ability to inhibit complement was also tested by assaying for specific inhibition of C3a and C5a production. For all experiments, a single human serum pool, to be used as a source of complement, was aliquoted and stored frozen at −70° C. Human IgG was heat-aggregated, aliquoted, and stored frozen at −70° C. For each experiment, serum aliquots were equilibrated at 37° C. with varying concentrations of sCR1 to be tested. The complement pathway was initiated by the addition of aggregated human IgG. Control samples containing no IgG were always included. After a fixed reaction time of 15 minutes (determined in an earlier time-course study to provide a convenient time interval during which the production of C5a or C3a is nearly complete, i.e., greater than 90%), the levels of the released complement peptides (C5a or C3a) were determined by radioimmunoassay using commercially available radioimmunoassay (RIA) kits (C5a RIA, Amersham Cat No. RPA.520; C3a RIA, Amersham Cat. No. RPA.518) in modified procedures.

Since a competitive immunoassay was used, complement peptide (C5a and C3a) concentrations varied inversely with the counts. The counts bound (CB) for a sample were defined as the total counts (in counts per minute, cpm) measured in the pellet.

The y-axis in FIG. 29 represents the fraction inhibition. The fraction inhibition is equal to the counts bound (CB) for a "sample", less the CB in the "sample with no sCR1", divided by the CB for the "no IgG control" less the CB in the "sample with no sCR1."

$$\text{INHIBITION} = \frac{[(CB\,\text{sample}) - (CB\,no\,sCR1)]}{[(CB\,no\,IgG) - (CB\,no\,sCR1)]}$$

13.3.2. Results

The activity of purified sCR1 was assayed by testing its ability to inhibit C5a and C3a production in an activated human serum sample.

As indicated by FIG. 29, under the conditions tested, purified sCR1 was able to maximally inhibit C5a production by 100% and C3a by 60%. Inhibition of 50% was observed at sCR1 concentrations of 5 μg/ml for C5a production and 15–20 μg/ml for C3a production. The data suggest that recombinant sCR1 inhibits the C5 convertase more efficiently than the C3 convertase.

14. EXAMPLE

Demonstration of Functional in Vivo Therapeutic Activity of Soluble CR1

14.1. Soluble CR1 Demonstrates in Vivo Function in a Reversed Passive Arthus Reaction The Arthus reaction is a classic immunologically induced inflammatory response caused by injecting antigen locally that then reacts with antibodies in circulation. The major biological response is characterized by immune complex deposition, complement fixation, polymorphonuclear (PMN) leukocyte infiltration, release of lysosomal enzymes, vasoactive amine, and local tissue damage (Uriuhura, T. and Movat, H. Z., 1966, Exp. Mol. Pathol. 5: 539–558; Cochrane, C. G., 1968, Adv. Immunol. 9: 97–162). A modification of the direct Arthus reaction, the reversed passive Arthus reaction (RPAR), has been used as a model for identifying anti-inflammatory agents (Pflum, L. R. and Graeme, M. L., 1979, Agents and Actions 9: 184–189). In a RPAR, antibody is injected locally and antigen is present in the circulation.

When tested in a rat RPAR model, soluble CR1 s were able to block the local inflammatory reaction. The mechanism of the action of this soluble CR1 function in vivo may be mediated through the inhibition of complement pathway enzymes.

14.1.1. Materials and Methods

Female five week old Sprague Dawley rats (CD strain) weighing about 100–125 grams (Charles River Laboratories, Wilmington, Mass.) were anesthesized with an intraperitoneal injection of 0.1 to 0.3 ml Avertin solution. This solution was a 1:2 dilution of a stock solution made with 1 g tribromoethanol in 15 ml Amel ethanol. The fur on the backs of the animals was shaved. Next, the tail was warmed, first with warm water and then with a heat lamp. Using a 1 ml syringe, 0.35 ml of ovalbumin (Calbiochem Corp., San Diego, Calif.) at 5 mg/ml in 0.15M phosphate buffered saline (PBS) was injected intravenously into the tail vein, about 1–2 inches from the tip of the tail. Five minutes later, the rats were injected intradermally with 0.08 ml of 20 mg/ml rabbit Ig fraction of anti-ovalbumin antibody having an antibody titer of 4 mg/ml (Organon Teknika Corp., Cappel Division, West Chester, Pa.) or with 0.08 ml of 20 mg/ml rabbit IgG (Sigma Chemical Co., St. Louis, Mo.), or with PBS. Each injection was performed in duplicate and the areas around the injection were circled with a marker pen. The rats were then monitored at 1, 4, and 18 hours. After 24 hours, the rats were killed by submerging them in dry ice for 3 minutes. Skin samples were dissected from the injected sites. One of the duplicate samples was fixed in 10% formalin for paraffin embedding and the other frozen for cryostat sections. Tissue sections were prepared and stained with hematoxylin and eosin.

14.1.2. Results

Figure 30A:
Figure 30B:
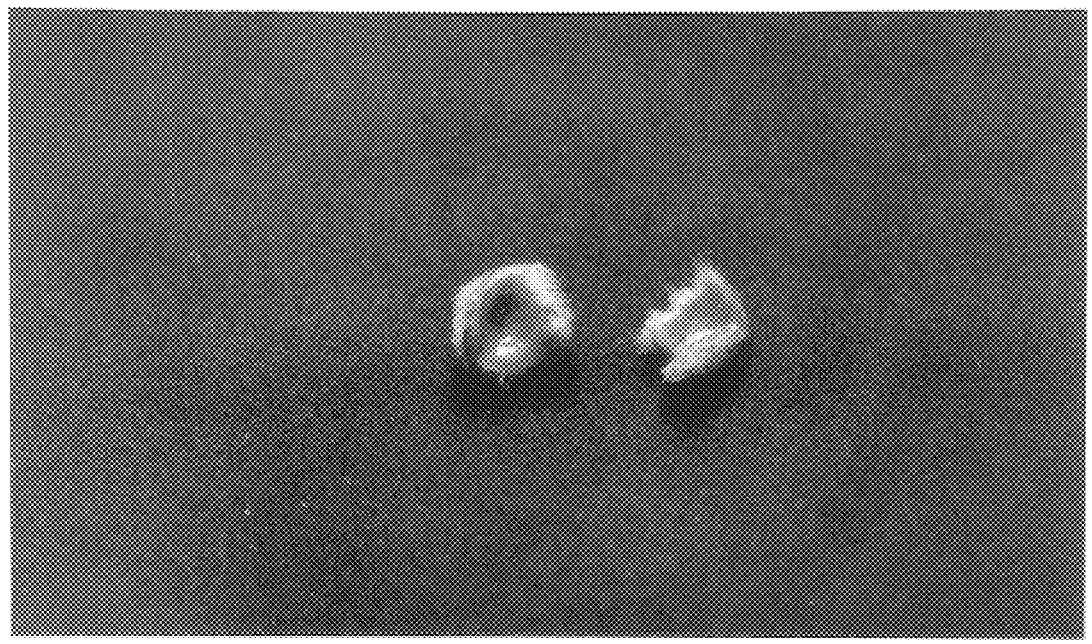

A weak RPAR reaction (e.g., edema and erythema) began to be visible after 3 to 5 hours following intradermal injection of anti-ovalbumin antibody. The intensity of the reaction gradually increased until the size of the reaction reached 3–5 mm in diameter after 24 hours (FIG. 30b). No reactions were observed in the rat skin where only non-immune rabbit IgG or PBS was injected.

Under microscopic examination of the tissue sections prepared from the site of the lesion, many acute inflammatory cells were visible in the dermis, particularly around the blood vessels (FIG. 31b). This is typically recognized as vasculitis and perivasculitis. The tissue indicated a typical inflammatory condition with extensive infiltration of PMN outside of the blood vessels, the presence of erythrocytes in the connective tissue, and the loosening of collagen fibers.

14.1.3. Effect of Intradermal Administration of Soluble CR1

A mixture of purified sCR1 was prepared by combining 40 μl of 0.75 mg/ml sCR1 with an equal volume of anti-ovalbumin or normal rabbit IgG or PBS. Either the sCR1:anti-ovalbumin mixture or the sCR1:rabbit IgG mixture, or the sCR1:PBS mixture was injected intradermally into intravenously ovalbumin primed rats. Barely visible lesions developed in the injection sites that received sCR1 plus anti-ovalbumin antibody (FIG. 30a). As expected, no lesions developed in the injection sites that received sCR1:rabbit IgG or sCR1:PBS. When sections of tissue surrounding the sCR1:anti-ovalbumin injection sites were examined microscopically, clusters of PMN and mononuclear cells could be found surrounding the venules, but there was no extensive infiltration of PMN or extravasation of erythrocytes (FIG. 31a). These data indicate that soluble CR1 administration caused an inhibition of damage to the endothelial cells and an inhibition of the inflammatory reaction.

In order to determine the minimum effective dosage of sCR1 that is required to block a RPAR in the above ovalbumin rat model, ten-fold serial dilutions (neat, 1/10, 1/100, 1/1,000 and 1/10,000) of the 0.75 mg/ml sCR1 stock were tested. Each sCR1 dilution was mixed with an equal volume of neat or one-half dilution of anti-ovalbumin antibody. Each site was injected with a total of 80 μl. The ability of sCR1 to inhibit RPAR was dose dependent, with effective reduction of edema observed at 300 ng per site (Table X).

TABLE X

EFFECT OF DOSAGE ON THE INHIBITION OF RPAR BY sCR1

| sCR1 (μg/site) | Extent of Remaining RPAR |
|---|---|
| 30 | +/− |
| 3 | +/− |
| 0.3 | +/− |
| 0.03 | ++ |
| 0.003 | ++++ |
| 0 | ++++ |

14.2. Pharmacokinetics of In Vivo Administered sCR1

The biological half-life of sCR1 in vivo was determined as follows. Rats of similar age (6 weeks) and body weight (110–125 g) were injected intravenously with 250 μg of sCR1 in 0.35 ml. At 2 minutes, 5 minutes, 10 minutes, 60 minutes, and 24 hours post-injection, the rats were sacrificed and blood was obtained from vena cava puncture. 1–2 ml of sera from each rat was obtained by centrifugation at 1800 rpm for 10 minutes, and the amount of sCR1 in each sample was determined by CR1 ELISA. Two-fold dilutions of 1 μg/ml of purified sCR1 spiked into control rat serum or detergent lysates of hemoglobin-free red blood cell ghosts ($1.6 \times 10^8$ ghosts/ml) were used as CR1 standards. The results are shown in Table XI.

TABLE XI

PHARMACOKINETIC DATA ON SERUM CONCENTRATIONS OF INJECTED sCR1 WITH TIME

| Time After Intravenous Injection | sCR1 Concentration (μg/ml) |
|---|---|
| Control | 0.01 |
| 2 min | 0.17 |
| 5 min | 0.80 |
| 10 min | 1.01 |
| 60 min | 0.38 |
| 24 hrs | 0.49 |

These data indicate that sCR1 can be detected 24 hours following intravenous injection. At 24 hours, the level of sCR1 in the serum was 50% of the peak level that was observed 10 minutes post-injection.

14.3. sCR1 Reduces Infarct Size in Rats with Reperfused Infarcted Myocardium As described herein, sCR1 which was able to inhibit the activity of the complement pathway C3/C5 convertase in vitro was also able to reduce the extent of reperfusion injury in an in vivo rat myocardial infarct model.

Myocardial infarction can be induced in a rat by coronary ligation. If established within the first few hours after myocardial infarction, reperfusion has been shown to reduce the infarct size, to improve the left ventricular function, and to reduce mortality (Braunwald, E. and Kloner, R. A., 1985, J. Clin. Invest. 76: 1713–1719). However, reperfusion to a myocardium that is severely ischemic but not irreversibly injured, can itself produce and extend injury. The mechanisms responsible for the reperfusion-induced injury may include injury mediated by oxygen free radicals and cellular calcium overload. Leukocytes acting either alone or-in concert with microvascular endothelial cells may contribute to this injury. Complement activation may be involved in this process (Rossen, R. D., et al., 1985, Cir. Res. 57: 119–130; Crawford, M. H., et al., 1988, Circulation 78: 1449–1458).

14.3.1. Methods

14.3.1.1. Induction of Rat Myocardial Infarct

Rats (n=14) weighing between 200 and 250 grams were anesthetized by inhalation of methoxyflurane, and had a right jugular vein cut-down and cannulation. Half (n=7) received 2 ml (1 mg) of sCR1 through the cannula, and half received 2 ml of saline placebo prepared and administered similarly. The animals had the jugular cannula removed, the jugular vein tied, and the site closed. A left thoracotomy was then performed in the fifth to sixth intercostal space, while intermittent positive pressure ventilation with 95% oxygen and 5% carbon dioxide was administered. A pericardiotomy was then performed, and the left coronary artery occluded by suture ligation within 2–3 mm left of the proximal aorta. The effect of this coronary ligation was to produce a large region at risk for anterior transmural infarction. The chest was transiently closed, while the rats remained under anesthesia. 35 minutes after occlusion, the chest was reopened and the ligature released. This time span was chosen so that a significant proportion of the risk region was potentially salvable. The thoracotomy was then permanently closed, and the animals allowed to awaken from anesthesia, usually within 5 to 10 minutes post-operatively. 100,000 units of benzathine penicillin G and 0.25 mg/kg morphine sulfate were administered intramuscularly. The animals were maintained on water and standard rat chow for one week and then sacrificed following heparinization and methoxyflurane anesthesia by excision of the heart.

14.3.1.2. Morphologic Analysis of Experimental Infarcts: Preparation of Hearts for Study Following excision of the heart, the aortas were rapidly cannulated and the coronary arteries perfused first with Krebs Henseleit solution to clear the hearts of blood and clots, and then with 30 mM KCl for diastolic cardiac arrest. The hearts were fixed by intracoronary perfusion and immersion in 10% buffered formalin. To adequately control filling pressure, the hearts were vented through the mitral value with plastic tubing. After fixation, the hearts were sliced transversely parallel to the atrioventricular groove in 2 mm sections from base to apex and histologic sections prepared.

14.3.2. Results

Survival was the same in both groups, viz., 6/7 rats survived 7 days and were analyzed. On gross inspection of the histologic slides, 5 of 6 placebo-treated rats had large transmural myocardial infarctions (estimated to be at least 15% of the total left ventricular mass). Only 1/6 surviving sCR1-treated animals had this finding of a large transmural infarction. The other sCR1-treated animals had small patchy infarcts comprising much less of the left ventricular mass (less than 15%). In fact, most of these were detectable only by microscopy, whereas the infarcts from placebo-treated rats were apparent by gross inspection.

14.3.3. Conclusions

The results indicate that sCR1 treatment is effective in reducing reperfusion injury in vivo and in ameliorating the effects of myocardial infarction. To the extent that reperfusion injury can be ameliorated, the absolute amount of salvaged myocardium can be increased and the time window for which reperfusion is clinically useful can be extended. Treatment with sCR1 should be a useful concomitant therapy with thrombolytics or balloon coronary angioplasty during acute infarction.

15. Deposit of Microorganisms

*E. coli* strain DK1/P3 carrying plasmid piABCD (designated pCR1-piABCD), encoding the full-length CR1 protein, was deposited with the Agricultural Research Culture Collection (NRRL), Peoria, Ill., on Mar. 31, 1988 and was assigned accession number B-18355. A supplemental deposit of *E. coli* strain DK1/P3 carrying plasmid pCR1-piABCD was deposited under the Budapest Treaty with the Agricultural Research Patent Culture Collection (NRRL), Peoria, Ill., on Jul. 17, 1997 and assigned the NRRL accession number B-18355N.

Chinese hamster ovary cell line DUX B11 carrying plasmid pBSCR1c/pTCSgpt clone 35.6, encoding a soluble CR1 molecule, was deposited with the American Type Culture Collection (ATCC), 10801 University Boulevard, Manassas, Va. 20110-2209 on Mar. 23, 1989 and was assigned accession number CRL 10052.

The present invention is not to be limited in scope by the microorganisms deposited since the deposited embodiments are intended as single illustration of one aspect of the invention and any microorganisms which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

It is also understood that all base pair sizes given for nucleotides are approximate and are used for the purpose of description.

Various references are cited herein, the disclosures of which are incorporated by reference in their entirety.

What is claimed is:

1. A CR1 protein composition comprising a purified, soluble CR1 protein having an amino acid sequence as depicted in FIGS. 1A to 1P and substantially lacking a transmembrane region, or a fragment of said soluble CR1 protein comprising at least two short consensus repeats, which soluble CR1 protein or fragment exhibits a complement regulatory activity of full-length CR1, and which purified, soluble CR1 protein or fragment is substantially pure, appearing as the dominant band when analyzed by SDS-PAGE.

2. A composition of claim 1, wherein said soluble CR1 protein or fragmnent is characterized by the ability to bind C3b.

3. A composition of claim 1, wherein said soluble CR1 protein or fragment is characterized by the ability to bind C4b.

4. A composition of claim 1, wherein said soluble CR1 protein or fragment is characterized by the abilities to bind C3b and to bind C4b.

5. A composition of claim 1, wherein said soluble CR1 protein or fragment has factor I cofactor ability.

6. A composition of claim 1, wherein said soluble CR1 protein or fragment can inhibit C3 convertase activity.

7. A composition of claim 1, wherein said soluble CR1 protein or fragment can inhibit C5 convertase activity.

8. A composition of claim 1, wherein said soluble CR1 protein or fragment is glycosylated.

9. A composition of claim 1, wherein said soluble CR1 protein or fragment is unglycosylated.

10. A composition of claim 1, wherein said soluble CR1 protein or fragment lacks a signal sequence.

11. A composition of claim 1, wherein said soluble CR1 protein or fragment is expressed in a host cell transformed with a nucleic acid molecule encoding said CR1 protein or fragment and wherein said CR1 protein or fragment is secreted from said cell.

12. A composition of claim 1, wherein said CR1 protein or fragment has the ability in vitro to inhibit neutrophil oxidative burst, complement-mediated hemolysis, or C3a and C5a production.

13. A composition of claim 1, wherein said soluble CR1 protein or fragment is encoded by a nucleic acid vector selected from the group consisting of pBSCR1c, pBSCR1s, pBMCR1c, pBSCR1c/pTCSgpt, and pBSCR1s/pTCSgpt.

14. A composition of claim 1, wherein said soluble CR1 protein or fragment is encoded by a nucleic acid vector selected from the group consisting of pT-CR1c1, pT-CR1c2, pT-CR1c3, pT-CR1c4, and pT-CR1c5.

15. A composition of claim 1, wherein said soluble CR1 protein or fragment is a deletion mutant having long homologous repeats BCD.

16. A composition of claim 1, wherein said soluble CR1 protein or fragment exhibits a complement regulatory activity selected from the group consisting of:

(i) the ability to bind C3b;

(ii) the ability to bind C4b;

(iii) the abilities to bind C3b and to bind C4b;

(iv) factor I cofactor activity;

(v) the ability to inhibit classical C3 convertase activity;

(vi) the ability to inhibit alternative C3 convertase activity;

(vii) the ability to inhibit classical C5 convertase activity;

(viii) the ability to inhibit alternative C5 convertase activity;

(ix) the ability to inhibit neutrophil oxidative burst;

(x) the ability to inhibit complement-mediated hemolysis;

(xi) the ability to inhibit C3a production; and (xii) the ability to inhibit C5a production.

17. A composition of claim 1, wherein said soluble CR1 protein or fragment exhibits a complement regulatory activity selected from the group consisting of:

(i) the ability to prevent reperfusion injury;

(ii) the ability to inhibit Arthus reaction;

(iii) the ability to reduce myocardial infarct size;

(iv) the ability to reduce inflammation; and (v) the ability to inhibit neutrophil mediated tissue damage.

18. A therapeutic composition comprising a composition according to claim 1 or claim 5 in an amount effective to regulate complement activity.

19. A composition of claim 1, wherein said soluble CR1 protein or fragment comprises CR1 short consensus repeats 11, 12, 13 and 14.

20. A composition of claim 1, wherein said soluble CR1 protein or fragment comprises CR1 short consensus repeats 17, 18, 19, 20 and 21.

21. A composition of claim 1, wherein said soluble CR1 protein or fragment comprises CR1 short consensus repeats 12, 13 and 14.

22. A composition of claim 1, wherein said soluble CR1 protein or fragment comprises CR1 short consensus repeats 17 and 18.

23. A composition of claim 1, wherein said soluble CR1 protein or fragment comprises CR1 short consensus repeats 15 and 16.

24. A composition of claim 1, wherein said soluble CR1 protein or fragment comprises CR1 short consensus repeats 12, 13, 14, 15, 16 and 17.

25. A composition of claim 1, wherein said soluble CR1 protein or fragment comprises CR1 short consensus repeats 12, 13, 14, 15, 16, 17, 18, 19, 20, 21, 22 and 23.

26. A composition of claim 1, wherein said soluble CR1 protein or fragment comprises CR1 short consensus repeats 6, 7, 8, 9, 10, 11 and 12.

27. A composition of claim 1, wherein said soluble CR1 protein or fragment comprises CR1 short consensus repeats 3, 4, 5, 6 and 7.

28. A composition of claim 1, wherein said soluble CR1 protein or fragment comprises CR1 short consensus repeats 1 and 2.

29. A composition of claim 1, wherein said soluble CR1 protein or fragment comprises CR1 short consensus repeats 1, 2, 3 and 4.

30. A composition of claim 1, wherein said soluble CR1 protein or fragment comprises CR1 short consensus repeats 2, 3, 4 and 5.

31. A composition of claim 1 comprising at least one of the CR1 long homologous repeats.

32. The composition of claim 31, comprising CR1 long homologous repeat A.

33. The composition of claim 31, comprising CR1 long homologous repeats A, B and D.

34. The composition of claim 31, comprising CR1 long homologous repeats A, C and D.

35. The composition of claim 31, comprising CR1 long homologous repeats A and D.

36. The composition of claim 31, comprising CR1 long homologous repeats B and D.

37. The composition of claim 31, comprising CR1 long homologous repeats C and D.

38. The composition of claim 31, comprising CR1 long homologous repeats B, C and D.

39. A CR1 protein having an amino acid sequence as depicted in FIGS. 1A to 1P, or a fragment of said CR1 protein comprising at least two short consensus repeats, which CR1 protein or fragment is expressed as a cell-surface protein on the surface of a non-human cell and exhibits a complement regulatory activity of full-length human CR1 as expressed on erythrocytes.

40. A soluble CR1 protein composition, expressed by a Chinese hamster ovary cell DUX B11 transfected with plasmid pBSCR1c/pTCSgpt, as deposited with the ATCC and assigned accession number CRL 10052 which expressed soluble CR1 protein is substantially pure, appearing as the dominant band when analyzed by SDS-PAGE.

41. A recombinant polypeptide, the amino acid sequence of which comprises at least a fragment of the amino acid sequence depicted in FIG. 1, which polypeptide has a complement regulatory activity, and which polypeptide is encoded by a nucleic acid vector selected from the group consisting of piBCD, piABD, piACD, piAD, piBD and piCD.

42. A recombinant polypeptide, the amino acid sequence of which comprises at least a fragment of the amino acid sequence depicted in FIG. 1, which polypeptide has a complement regulatory activity, and which polypeptide is a deletion mutant lacking long homologous repeat A.

* * * * *